US012559459B2

(12) United States Patent
Sugino et al.

(10) Patent No.: US 12,559,459 B2
(45) Date of Patent: Feb. 24, 2026

(54) AROMATIC HETEROCYCLIC DERIVATIVE, AND ORGANIC ELECTROLUMINESCENT ELEMENT, ILLUMINATION DEVICE, AND DISPLAY DEVICE USING AROMATIC HETEROCYCLIC DERIVATIVE

(71) Applicant: Merck Patent GmbH, Darmstadt (DE)

(72) Inventors: Motoaki Sugino, Akishima (JP); Eisaku Katoh, Hachioji (JP)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/550,590

(22) PCT Filed: Feb. 12, 2016

(86) PCT No.: PCT/JP2016/054126
§ 371 (c)(1),
(2) Date: Aug. 11, 2017

(87) PCT Pub. No.: WO2016/129672
PCT Pub. Date: Aug. 18, 2016

(65) Prior Publication Data

US 2018/0037546 A1 Feb. 8, 2018

(30) Foreign Application Priority Data

Feb. 13, 2015 (JP) ................................ 2015-026039

(51) Int. Cl.
*H01L 51/00* (2006.01)
*C07D 209/82* (2006.01)
(Continued)

(52) U.S. Cl.
CPC ......... *C07D 209/82* (2013.01); *C07D 405/14* (2013.01); *C07D 409/14* (2013.01)

(58) Field of Classification Search
CPC .. C07D 209/82; C07D 405/14; C07D 409/14; H01L 51/50; H01L 51/5012;
(Continued)

(56) References Cited

U.S. PATENT DOCUMENTS 6,278,237 B1 * 8/2001 Campos .................. H01L 27/32 313/483
2011/0272687 A1 * 11/2011 Katakura ............ C07D 405/14 257/40
(Continued)

FOREIGN PATENT DOCUMENTS

CN 102770427 A 11/2012
CN 103764650 A 4/2014
(Continued)

OTHER PUBLICATIONS

International Search Report corresponding to Application No. PCT/JP2016/054126; Mailing date of May 10, 2016.
(Continued)

*Primary Examiner* — Alexander C Kollias
(74) *Attorney, Agent, or Firm* — CANTOR COLBURN LLP

(57) ABSTRACT

The present invention addresses the problem of providing a novel aromatic heterocyclic derivative, providing an organic EL element that uses the derivative and has high luminous efficiency, long luminescence life, and few changes over time when used under high temperatures, and providing a display device and an illumination device that are equipped with the organic El element. This aromatic heterocyclic derivative is characterized by having a specific structure which includes a carbazole ring.

12 Claims, 2 Drawing Sheets

(51) Int. Cl.
*C07D 405/14* (2006.01)
*C07D 409/14* (2006.01)

(58) Field of Classification Search
CPC ............ H01L 51/0072; H01L 51/0073; H01L 51/0074; H01L 51/0067; C09K 11/06; C09K 2211/1029; C09K 2211/1088; C09K 2211/1092; C09K 2211/1044; C09K 2211/1059; H10K 85/6572; H10K 85/6574; H10K 85/6576
See application file for complete search history.

(56) References Cited

U.S. PATENT DOCUMENTS

| | | | | |
|---|---|---|---|---|
| 2012/0223276 | A1 | 9/2012 | Parham et al. | |
| 2013/0062597 | A1* | 3/2013 | Yoshida | H01L 51/0073 257/40 |
| 2014/0158992 | A1 | 6/2014 | Xia et al. | |
| 2015/0171342 | A1* | 6/2015 | Jung | C07D 409/14 546/276.7 |
| 2015/0336937 | A1* | 11/2015 | Lee | C07D 405/14 257/40 |
| 2016/0111657 | A1* | 4/2016 | Lee | H01L 51/0073 257/40 |
| 2016/0181548 | A1 | 6/2016 | Parham et al. | |
| 2016/0226001 | A1 | 8/2016 | Parham et al. | |
| 2017/0186965 | A1* | 6/2017 | Parham | H10K 85/622 |
| 2017/0207399 | A1* | 7/2017 | Parham | H05B 33/20 |

FOREIGN PATENT DOCUMENTS

| | | | |
|---|---|---|---|
| CN | 103923065 | A | 7/2014 |
| EP | 2980094 | A1 | 2/2016 |
| JP | 2009021336 | A | 1/2009 |
| JP | 2009021336 | A2 † | 1/2009 |
| JP | 2010114180 | A | 5/2010 |
| JP | 2011008991 | A | 1/2011 |
| JP | 2013510803 | A | 3/2013 |
| JP | 2014094935 | A1 | 5/2014 |
| JP | 2014116454 | A2 † | 6/2014 |
| JP | 2013131518 | A | 7/2014 |
| JP | 2014209618 | A | 11/2014 |
| JP | 2016149520 | A | 8/2016 |
| JP | 2016149521 | A | 8/2016 |
| JP | 2016149522 | A | 8/2016 |
| JP | 2016149523 | A | 8/2016 |
| KR | 20120104246 | A | 9/2012 |
| KR | 1020140068847 | A | 6/2014 |
| KR | 20140099082 | A | 8/2014 |
| KR | 1020140099082 | A | 8/2014 |
| WO | 2007069569 | A1 | 6/2007 |
| WO | 11057706 | A2 † | 5/2011 |
| WO | 2011057706 | A2 | 5/2011 |
| WO | 2012099038 | A1 | 7/2012 |
| WO | 2013035275 | A1 | 3/2013 |
| WO | 2013137001 | A1 | 9/2013 |
| WO | 2014013721 | A1 | 1/2014 |
| WO | 2014090368 | A1 | 6/2014 |
| WO | 2014181640 | A1 | 11/2014 |
| WO | 2015014434 | A1 | 2/2015 |
| WO | 2015014435 | A1 | 2/2015 |

OTHER PUBLICATIONS

JP Notification of Reasons of Rejection corresponding to Application No. JP2015-026039; Mailing date of Mar. 31, 2015.
JP Notification of Reasons of Rejection corresponding to Application No. JP2015-164429; Mailing date of Aug. 23, 2016.
JP Notification of Reasons of Rejection corresponding to Application No. JP2015-164429; Mailing date of Jun. 6, 2017.
JP Notification of Reasons of Rejection corresponding to Application No. JP2015-164436; Mailing date of Aug. 23, 2016.
JP Notification of Reasons of Rejection corresponding to Application No. JP2015-164436; Mailing date of Jun. 6, 2017.
JP Notification of Reasons of Rejection corresponding to Application No. JP2015-164438; Mailing date of Aug. 23, 2016.
JP Notification of Reasons of Rejection corresponding to Application No. JP2015-164438; Mailing date of Jun. 6, 2017.
JP Notification of Reasons of Rejection corresponding to Application No. JP2015-164443; Mailing date of Aug. 23, 2016.
JP Notification of Reasons of Rejection corresponding to Application No. JP2015-164443; Mailing date of Jun. 6, 2017.
Korean Intellectual Property Office Notice of Preliminary Rejection corresponding to Application No. 10-2017-7022113; Mailing date of Jul. 16, 2018.
Extended European Search Report corresponding to Application No. 16749315.4-1462 PCT/JP2016054126; Mailing date of Oct. 20, 2017.
Korean (KIPO) Notice of Final Rejection corresponding to Application No. 10-2017-7022113; Mailing date of Jan. 31, 2019.
International Preliminary Report on Patentability corresponding to Application No. PCT/JP2016/054126; Issue date of Aug. 15, 2017.
Korean Intellectual Property Office Second Notice of Final Rejection corresponding to Application No. 10-2017-7022113; Dated Apr. 29, 2019.
SIPO First Office Action corresponding to Application No. 201680009902.9; Dated Sep. 20, 2019.
Summary translation of Korean IP Trial and Appeal Board decision for corresponding KR application No. 10-2017-7022113, dated Oct. 22, 2020.
KIPO Notice of Final Rejection for corresponding KR Application No. 10-2019-7021634; Issued on Nov. 26, 2021.
EPO Third Party Observations against EP3257850A; Application No. 16749315.4; dated Dec. 15, 2022.

* cited by examiner
† cited by third party

AROMATIC HETEROCYCLIC DERIVATIVE, AND ORGANIC ELECTROLUMINESCENT ELEMENT, ILLUMINATION DEVICE, AND DISPLAY DEVICE USING AROMATIC HETEROCYCLIC DERIVATIVE

This is the U.S. national stage of application No. PCT/JP2016/054126, filed Feb. 12, 2016. Priority under 35 U.S.C. § 119(a) and 35 U.S.C. § 365(b) is claimed from Japanese Application No. 2015-026039, filed Feb. 13, 2015, the disclosures of which are also incorporated herein by reference.

TECHNICAL FIELD

The present invention relates to an aromatic heterocyclic derivative, an organic electroluminescent element using the same, a lighting device, and a display device. More specifically, the present invention relates to an aromatic heterocyclic derivative, an organic electroluminescent element which uses the same and having high emission efficiency, a long emission lifetime, and a small deterioration with time when used even under a high-temperature condition, a lighting device and a display device provided with this organic electroluminescent element.

BACKGROUND

An organic electroluminescent element (hereafter, it may be called as “an organic EL element”) is a thin-film type total solid element having a constitution of an organic film layer (a single layer or a plurality of layers) containing an organic luminescent substance interposed between an anode and a cathode. When an electric filed is applied to an organic EL element, a hole is injected from an anode and an electron is injected from a cathode into an organic film layer. The hole and the electron are recombined in a light emitting layer (a layer containing an organic luminescent substance) to produce an exciton. An organic electroluminescent element is a luminescent element which uses light emission (fluorescence or phosphorescence) from this exciton. This is a technology expected to become a flat display or a lighting device of the next generation.

It was reported the following from the Princeton University. In principle, an organic EL element utilizing phosphorescence emission from the excited triplet will realize an emission efficiency of 4 times larger compared with an emission efficiency of an organic EL element utilizing fluorescence emission. Since then, there have been investigated all over the world the materials exhibiting phosphorescence emission at room temperature, the layer constitution and the electrode of the luminescent element.

As described above, a phosphorescence emission mode has a very high potential. However, in an organic EL element utilizing phosphorescence emission, the method of controlling the position of the emission center, in particular, the method of recombination inside of the light emitting layer to stably carrying out emission is a technological problem to be solved for improving efficiency and lifetime of the element. This is a large difference from an organic EL element utilizing fluorescence emission.

In recent years, it has been well known a multi-laminated layer type element which is provided with a hole transport layer located in the anode side of the light emitting layer, or an electron transport layer located in the cathode side of the light emitting later. Further, as a light emitting layer, it has been often used a mixed layer containing a phosphorescence emitting compound as a light emitting dopant and a host compound.

On the other hand, from the viewpoint of materials, it is expected to create a novel material for achieving an improved property of the element. In particular, it was reported an organic EL element material which uses a host compound for a phosphorescence emitting compound. This host compound contains a multi-condensed ring compound bonded with a 6-membered nitrogen containing heterocyclic ring through an arylene linking group (refer to Patent documents 1 to 3, for example).

When the compounds described in the Patent documents 1 to 3 are used for organic EL element materials, a lifetime and an emission efficiency of the element were improved to some extent. However, the improvement was not sufficient. Further improvement was required. Further, it was found that the organic EL elements using these compounds had a defect of inferior thermal stability.

PRIOR ART DOCUMENTS

Patent Documents

Patent document 1: WO 2013/035275

Patent document 2: WO 2007/069569

Patent document 3: US 2014/0158992

SUMMARY OF THE INVENTION

Problems to be Solved by the Invention

The present invention has been made in view of the above-described problems and situation. An object of the present invention is to provide a novel aromatic heterocyclic derivative. Another object of the present invention is to provide an organic electroluminescent element which uses the same and having high emission efficiency, a long emission lifetime, and a small deterioration with time when used even under a high-temperature condition. Another object of the present invention is to provide a display device and a lighting device provided with this organic electroluminescent element.

Means to Solve the Problems

The present inventors have investigated the cause of the above-described problems in order to solve the problems. It was found that an aromatic heterocyclic derivative having a specific structure containing a carbazole ring is efficient to solve the above-described problems. Thus, the present invention has been achieved.

That is, the above-described problems of the present invention are solved by the following embodiments.

1. An organic electroluminescent element comprising at least an organic layer interposed between an anode and a cathode, the organic layer containing at least a light emitting layer, wherein the organic layer contains an aromatic heterocyclic derivative having a structure represented by one of Formulas (1), (2), (3), and (4).

Formula (1)

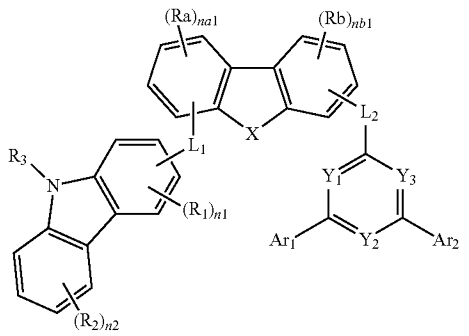

Formula (2)

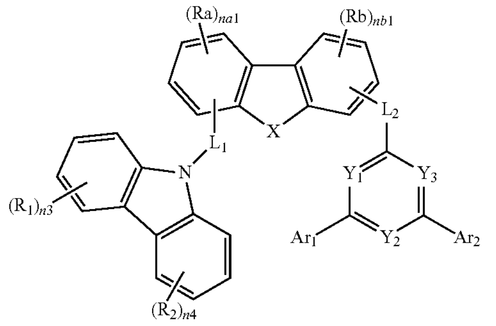

Formula (3)

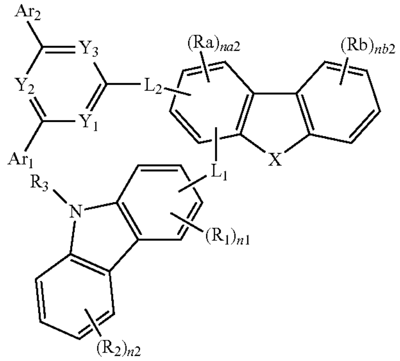

Formula (4)

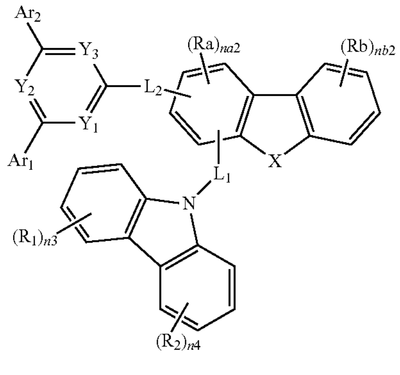

In Formulas (1), (2), (3), and (4), $Y_1$, $Y_2$ and $Y_3$ each independently represent CR' or a nitrogen atom, and at least one of $Y_1$, $Y_2$ and $Y_3$ represents a nitrogen atom.

R', $Ar_1$ and $Ar_2$ each represent:

a hydrogen atom;

a substituted or unsubstituted alkyl group having 1 to 12 carbon atoms, or a substituted or unsubstituted aryl group having 6 to 30 ring forming carbon atoms.

Not all of R', $Ar_1$ and $Ar_2$ represent hydrogen atoms at the same time.

X represents an oxygen atom or a sulfur atom.

Ra and Rb each independently represent a substituent.

$L_1$ represents:

a single bond;

a substituted or unsubstituted alkylene group having 1 to 12 carbon atoms;

a substituted or unsubstituted arylene group having 6 to 30 ring forming carbon atoms; or a divalent linking group composed of combination of these groups.

$L_2$ represents:

a single bond;

a substituted or unsubstituted alkylene group having 1 to 12 carbon atoms;

a substituted or unsubstituted arylene group having 6 to 30 ring forming carbon atoms;

a substituted or unsubstituted heteroarylene group having 5 to 30 ring forming atoms; or a divalent linking group composed of combination of these groups.

$R_1$ and $R_2$ each independently represent:

a substituted or unsubstituted alkyl group having 1 to 12 carbon atoms; a cyano group; a halogen atom; or an unsubstituted or substituted aryl group having 6 to 30 ring forming carbon atoms, provided that the substituted aryl group has a substituent represented by Formulas (A-1) or (A-2).

$R_3$ represents:

a substituted or unsubstituted alkyl group having 1 to 12 carbon atoms;

a substituted or unsubstituted aryl group having 6 to 30 ring forming carbon atoms; or a substituted or unsubstituted heteroaryl group having 5 to 30 ring forming atoms.

n1, na1, and nb1 each independently represent an integer of 0 to 3, na2 represents an integer of 0 to 2, and n2, n3, n4, and nb2 each independently represent an integer of 0 to 4.

When n1 to n4, na1, nb1, na2, and nb2 each represent an integer of 2 or more, a plurality of $R_1$, $R_2$, Ra, and Rb may be the same or different, and adjacent Ra and Rb may be bonded together to form a ring structure.

Formula (A-1)

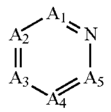

Formula (A-2)

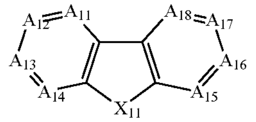

In Formulas (A-1) and (A-2), $A_1$ to $A_5$ and $A_{11}$ to $A_{18}$ each independently represent CRc or a nitrogen atom, and Rc represents a hydrogen atom, a substituent, or a bond.

One of $A_1$ to $A_5$ and one of $A_{11}$ to $A_{18}$ represent CRc, and Rc represents a bond which is directly bonded to an aryl group having 6 to 30 ring forming carbon atoms and represented by $R_1$ and $R_2$.

Other Rc may be the same or different, and adjacent Rc may be bonded together to form a ring structure.

$X_{11}$ represents an oxygen atom or a sulfur atom.

2. The organic electroluminescent element described in the embodiment 1, wherein in Formulas (1), (2), (3) and (4), $L_1$ represents a single bond, a phenylene group, a biphenylene group, or an alkylene group having 2 carbon atoms or less.

3. The organic electroluminescent element described in the embodiments 1 or 2, wherein in Formulas (1), (2), (3) and (4), $L_2$ represents a single bond, a phenylene group, a heteroarylene group, or an alkylene group having 2 carbon atoms or less.

4. The organic electroluminescent element described in any one of the embodiments 1 to 3, wherein in Formulas (1), (2), (3) and (4), $L_1$ is bonded to a position 2 or a position 4 in a condensed ring containing X represented by Formula (1) of the aromatic heterocyclic derivative Formula (I)

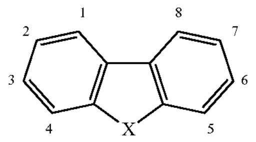

5. The organic electroluminescent element described in any one of the embodiments 1 to 4, wherein in Formulas (1) and (2). $L_2$ is bonded to a position 5 or a position 7 in a condensed ring containing X represented by Formula (I) of the aromatic heterocyclic derivative.

Formula (I)

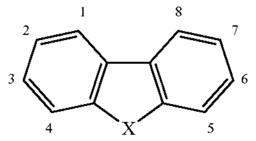

6. The organic electroluminescent element described in any one of the embodiments 1 to 4.

wherein in Formulas (3) and (4), $L_2$ is bonded to a position 2 or a position 4 in a condensed ring containing X represented by Formula (I) of the aromatic heterocyclic derivative.

Formula (I)

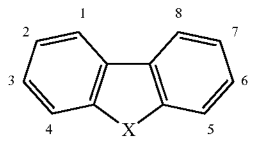

7. The organic electroluminescent element described in any one of the embodiments 1 to 6, wherein in Formulas (1), (2), (3) and (4), all of $Y_1$ to $Y_3$ represent a nitrogen atom.

8. The organic electroluminescent element described in any one of the embodiments 1 to 7, wherein in Formulas (1), (2), (3) and (4), $Ar_1$ and $Ar_2$ represent a substituted or unsubstituted aryl group having 6 to 30 ring forming carbon atoms.

9. The organic electroluminescent element described in any one of the embodiments 1 to 8.

wherein the organic layer containing an aromatic heterocyclic derivative is a light emitting layer.

10. The organic electroluminescent element described in any one of the embodiments 1 to 9, wherein the light emitting layer contains the aromatic heterocyclic derivative as a host compound.

11. The organic electroluminescent element described in any one of the embodiments 1 to 10, wherein the light emitting layer contains a phosphorescence emitting compound.

12. The organic electroluminescent element described in any one of the embodiments 1 to 11, wherein the light emitting layer further contains another host compound having a different structure from the aforesaid aromatic heterocyclic derivative.

13. A display device provided with the organic electroluminescent element described in any one of the embodiments 1 to 12.

14. A lighting device provided with the organic electroluminescent element described in any one of the embodiments 1 to 12.

15. The aromatic heterocyclic derivative having a structure represented by Formulas (1), (2), (3), and (4) contained in the organic electroluminescent element described in the embodiment 1.

Effects of the Invention

By the above-described embodiments of the present invention, it is possible to provide a novel aromatic heterocyclic derivative. Further, it is possible to provide an organic electroluminescent element which uses the same and having high emission efficiency, a long emission lifetime, and a small deterioration with time when used even under a high-temperature condition. Moreover, it is possible to provide a display device and a lighting device provided with this organic electroluminescent element.

A formation mechanism or an action mechanism of the effects of the present invention is not clearly identified, but it is supposed as follows.

A driving voltage of an organic EL element is preferably small. This may be achieved by making the highest occupied molecular orbital energy level (HOMO level) of the compound used for the element to be high, and by making the lowest unoccupied molecular orbital energy level (LUMO level) to be low. By this, an injection property of the charge in to the light emitting layer will be increased and a driving voltage may be lowered.

However, when the HOMO level is made to be high and the LUMO level is made to be low, the excited singlet ($S_1$ energy) becomes small, and the excited triplet ($T_1$ energy) also becomes small. In particular, when a host compound is used for a phosphorescence emitting dopant, this decrease of the $T_1$ energy becomes a problem.

As a means to solve this problem, one of the ways may be to make the difference (ΔEst) between the $S_1$ energy and the $T_1$ energy to be small.

By making ΔEst to be small, the $T_1$ energy level can be kept high. It may be obtained the same energy as the decreased $S_1$ energy by making the HOMO level to be high and the LUMO level to be low. It can be understood by the following scheme describing the relationship of ΔEst, the $S_1$ energy, and the $T_1$ energy.

$$T_1=S_1-\Delta Est$$

ΔEst may be made to be small by decreasing an interaction of parallel spins in the molecule. Namely, it may be achieved by making apart the center distance between the HOMO localized portion and the LUMO localized portion. In the compound of the present invention, the center of HOMO is made to be localized on the carbazole ring, and the center of LUMO is made to be localized on the 6-membered nitrogen containing heteroaromatic ring. Further, a preferably, each center portion is made to be at the terminal of the molecule. However, the 6-membered nitrogen containing heteroaromatic ring without a substituent is unstable when the ring has a large number of nitrogen atoms. Therefore, it is required to introduce a minimum number of appropriate substituents.

When a flexible group such as an alkylene group is introduced in a portion where the carbazole ring and the 6-membered nitrogen containing heterocyclic ring are bonded, the rigidity of the whole molecule is decreased. As a result, it will be induced a problem that the molecule tends to cause a morphological change in the film. Therefore, in the aromatic heterocyclic derivative of the present invention, it was introduced a condensed ring structure (containing X) between the carbazole ring and the 6-membered nitrogen containing heterocyclic ring. This condensed ring structure does not affect the localized portions of HOMO and LUMO, and improves the rigidity of the whole molecule. By this embodiment, the above-described problem was resolved. Further, by the introduction of the condensed ring structure (containing X), it was supposed the following: Tg (glass transition temperature) was increased, aggregation and crystallization were prevented, decrease of efficiency and lifetime was prevented, and stability under high-temperature condition was improved.

By the design that the localized centers of HOMO and LUMO are located at the terminal of the molecule, the hopping transfer of electrons becomes easier Consequently, the temporal change of carrier transferring efficiency was restrained and the lifetime of the element was improved.

In addition, when the size of the molecule is unnecessarily large, a sublimation property of the molecule will be lowered, and vapor deposition will become difficult. This will lead to decrease in productivity. Therefore, preferably, the molecule has a molecular weight suitable for vapor deposition.

Further, when a substituent is introduced to the condensed ring structure (containing X), it is possible to apply a synthetic method of high regioselectivity. As a result, the compound may be synthesized with high yield and high purity. It may be produced the compound with an appropriate cost.

Through suitable selection of the substituent on the carbazole ring, the compound of the present invention will have an improved thermal stability. It enables to achieve an element having an improved thermal stability under heating condition over a long period of time.

EMBODIMENTS TO CARRY OUT THE INVENTION

Figure 1:
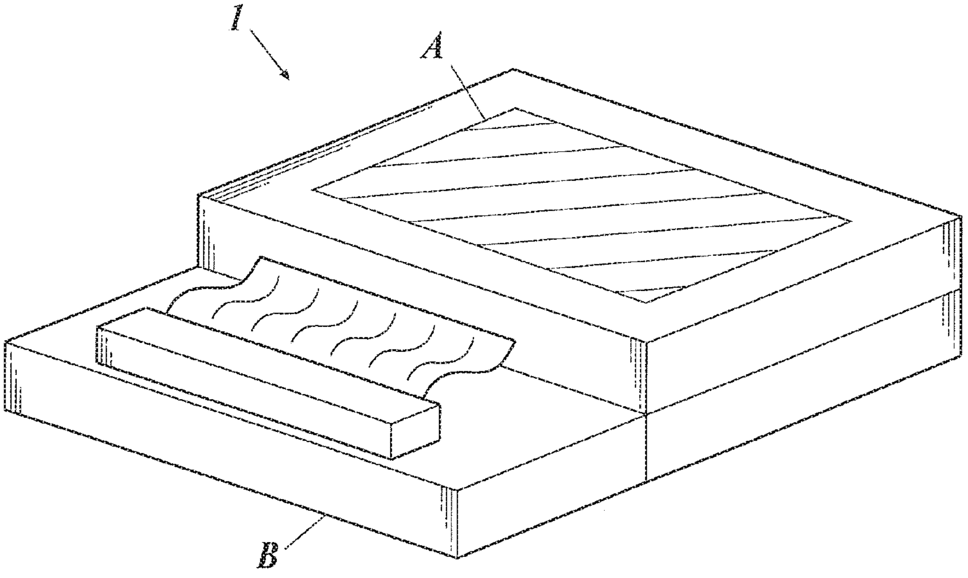
FIG. 1 is a schematic perspective drawing illustrating an example of a constitution of a display device of the present invention.

An organic electroluminescent element of the present invention contains at least an organic layer interposed between an anode and a cathode, the organic layer containing a light emitting layer. It is characterized in that at least one of the organic layers contains an aromatic heterocyclic derivative having a structure represented by Formulas (1), (2), (3), and (4).

These features are technical features commonly owned by the invention according to the above-described embodiments 1 to 15.

From the viewpoint of obtaining an effect of the present invention, a preferable embodiment of the present invention is that, in Formulas (1), (2), (3) and (4), $L_1$ represents a single bond, a phenylene group, a biphenylene group, or an alkylene group having 2 carbon atoms or less. This will result in obtaining an effect of improved thermal stability due to the increase of Tg (glass transition temperature). Further, it is preferable that, in Formulas (1), (2), (3) and (4), $L_2$ represents a single bond, a phenylene group, a heteroarylene group, or an alkylene group having 2 carbon atoms or less. This will also result in obtaining an effect of improved thermal stability due to the increase of Tg.

In the present invention, it is preferable that, in Formulas (1), (2), (3) and (4), $L_1$ is bonded to a position 2 or a position 4 in a condensed ring containing X represented by Formula (I) of the aromatic heterocyclic derivative. By this, it is possible to apply a synthetic method of high regioselectivity. As a result, the compound may be synthesized with high yield and high purity.

It is also preferable that, in Formulas (1) and (2), $L_2$ is bonded to a position 5 or a position 7 in a condensed ring containing X represented by Formula (I) of the aromatic heterocyclic derivative. By this, it is possible to apply a synthetic method of high regioselectivity. As a result, the compound may be synthesized with high yield and high purity.

In the present invention, it is also preferable that, in Formulas (3) and (4), $L_2$ is bonded to a position 2 or a position 4 in a condensed ring containing X represented by Formula (I) of the aromatic heterocyclic derivative. By this, it is possible to apply a synthetic method of high regioselectivity. As a result, the compound may be synthesized with high yield and high purity.

From the viewpoint of obtaining an effect of the present invention, a preferable embodiment of the present invention is that, in Formulas (1), (2), (3) and (4), all of $Y_1$ to $Y_3$ represent a nitrogen atom. Another preferable embodiment is that, in Formulas (1), (2), (3) and (4), $Ar_1$ and $Ar_2$ represent a substituted or unsubstituted aryl group having 6 to 30 ring forming carbon atoms. By this, it will be obtained an effect of improved stability in an excited state of the compound.

Further, in the present invention, it is preferable that the organic layer containing an aromatic heterocyclic derivative is a light emitting layer. By this, it will be obtained effects of high efficiency and long lifetime.

Further it is preferable that the light emitting layer contains the aromatic heterocyclic derivative as a host compound. From the viewpoint of high efficiency and long lifetime, it is preferable that the light emitting layer contains a phosphorescence emitting compound.

It is preferable that the light emitting layer further contains another host compound having a different structure from the aromatic heterocyclic derivative. By this, it will be obtained effects of improved recombination probability caused by adjustment of a carrier balance.

An organic electroluminescent element of the present invention is suitably used for a lighting device and a display device.

Further, it is preferable that an organic electroluminescent element of the present invention contains a compound having a structure represented by Formulas (1), (2), (3), and (4).

The present invention and the constitution elements thereof, as well as configurations and embodiments, will be detailed in the following. In the present description, when two figures are used to indicate a range of value before and after "to", these figures are included in the range as a lowest limit value and an upper limit value.

An organic electroluminescent element of the present invention is characterized in that at least one of the organic layers contains an aromatic heterocyclic derivative represented by Formulas (1), (2), (3), and (4).

The embodiments to carry out the present invention will be described in detail in the following. However, the present invention is not limited to these.

<<Aromatic Heterocyclic Derivative Represented by Formulas (1), (2), (3), and (4)>>

In Formulas (1), (2), (3), and (4), $Y_1$, $Y_2$ and $Y_3$ each independently represent CR' or a nitrogen atom, and at least one of $Y_1$, $Y_2$ and $Y_3$ represents a nitrogen atom.

More preferably, two or three of $Y_1$, $Y_2$ and $Y_3$ represent a nitrogen atom. Still more preferably, all of $Y_1$, $Y_2$ and $Y_3$ represent a nitrogen atom.

R', $Ar_1$ and $Ar_2$ each independently represent: a hydrogen atom; a substituted or unsubstituted alkyl group having 1 to 12 carbon atoms; or a substituted or unsubstituted aryl group having 6 to 30 ring forming carbon atoms. Here, not all of R', $A_r$, and $Ar_2$ represent hydrogen atoms at the same time.

An alkyl group having 1 to 12 carbon atoms and represented by R', $Ar_1$ and $Ar_2$ may be a straight chain or a branched structure as long as it does not inhibit the function of the compound of the present invention. The alkyl group may be a cyclic structure such as a cycloalkyl group.

Examples of an alkyl group having 1 to 12 carbon atoms include: a methyl group, an ethyl group, a propyl group, a butyl group, a pentyl group, a hexyl group, a heptyl group, an octyl group, a nonyl group, a decyl group, an undecyl group, a dodecyl group, an isopropyl group, a neopentyl group, a cyclopropyl group, a cyclobutyl group, a cyclopentyl group, a cyclohexyl group, and a cyclooctyl group.

An aryl group (it may be called as an aromatic hydrocarbon ring group) represented by R', $Ar_1$, and $Ar_2$, and having 6 to 30 ring forming carbon atoms may be a non-condensed ring or a condensed ring. Examples thereof include: a phenyl group, a naphthyl group, an anthryl group, a phenanthryl group, a pyrenyl group, a chrysenyl group, a biphenyl group, a terphenyl group, a quarterphenyl group, a fluoranthenyl group, a triphenylenyl group, a fluorenyl group, an azulenyl group, an acenaphthenyl group, an indenyl group, and an indenofluorenyl group.

In order to keep the excited triplet energy level ($T_1$ energy level) of the compound in the present invention to be a suitable value, preferable aryl groups are: a phenyl group, a naphthyl group, a phenanthryl group, a biphenyl group, a terphenyl group, a quarterphenyl group, a triphenylenyl group, and a fluorenyl group.

The above-described alkyl group or aryl group may further have a substituent as long as it does not inhibit the function of the compound of the present invention. Specific examples of a substituent are the same substituents represented by Ra and Rb that will be described later.

Preferably, R' is a hydrogen atom or an alkyl group. More preferably, R' is a hydrogen atom.

Preferably, $Ar_1$ and $Ar_2$ are an alkyl group or an aryl group. More preferably, Art and $Ar_2$ are an alkyl group having 4 or less carbon atoms or an aryl group.

Ra and Rb each independently represent a substituent.

As a substituent represented by Ra and Rb, it is not limited in particular as long as it does not inhibit the function of the compound of the present invention. The substituent may be actively used for finely adjusting to obtain an effect of the present invention.

Examples of a substituent include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group, an allyl group); an alkynyl group (for example, an ethynyl group and a propargyl group); an aromatic hydrocarbon group (also called an aromatic hydrocarbon ring, an aromatic carbon ring group or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyl group); an aromatic heterocyclic group (for example, a pyridyl group, a pyrazyl group, a pyrimidinyl group, a triazyl a group, a furyl group, a pyrrolyl group, an imidazolyl group, a benzimidazolyl group, a pyrazolyl group, a pyrazinyl group, a triazolyl group (for example, 1,2,4-triazol-1-yl group, and 1,2,3-triazol-1-yl group), an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, an azacarbazolyl group (indicating a ring structure in which one of the carbon atoms constituting the carbazole ring of the carbazolyl group is replaced with nitrogen atoms), a quinoxalinyl group, a pyridazinyl group, a triazinyl group, a quinazolinyl group, and a phthalazinyl group); a heterocyclic group (for example, a pyrrolidyl group, an imidazolidyl group, a morpholyl group, and an oxazolidyl group); an alkoxy group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxy-carbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethyl carbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethyhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethymexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-pyridylaminoureido group); a sulfinyl group (for example, a methylsulfinyl group, an ethylsufinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group); an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a halogen atom (for example, a fluorine atom, a chlorine atom and a bromine atom); a fluorinated hydrocarbon group (for example, a fluoromethyl group, trifluoromethyl group, a pentafluoroethyl group and a pentafluorophenyl group); a cyano group; a nitro group; a hydroxyl group; a mercapto group; a silyl group (for example, a trimethylsilyl group, a triisopropylsilyl group, a triphenylsilyl group, and a phenyldiethylsilyl group) and a phosphono group.

Moreover, these substituents may be further substituted by the above-mentioned substituent. Further, a plurality of these substituents may be bonded with each other to form a ring.

When there are a plurality of Ra or Rb, Ra and Rb may be the same or different, and adjacent Ra and Rb may be bonded together to form a ring structure.

Ra and Rb are preferably an alkyl group, an aryl group, or a heteroaryl group.

$L_1$ represents: a single bond; a substituted or unsubstituted alkylene group having 1 to 12 carbon atoms; a substituted or unsubstituted arylene group having 6 to 30 ring forming carbon atoms; or a divalent linking group composed of combination of these groups.

$L_2$ represents: a single bond; a substituted or unsubstituted alkylene group having 1 to 12 carbon atoms; a substituted or unsubstituted arylene group having 6 to 30 ring forming carbon atoms; a substituted or unsubstituted heteroarylene group having 5 to 30 ring forming atoms; or a divalent linking group composed of combination of these groups.

An alkylene group having 1 to 12 carbon atoms and represented by $L_1$ and $L_2$ may be a straight chain or a branched structure as long as it does not inhibit the function of the compound of the present invention. The alkylene group may be a cyclic structure such as a cycloalkylene group.

Examples of an alkylene group having 1 to 12 carbon atoms are a divalent group derived from an alkyl group having 1 to 12 carbon atoms and represented by $Ar_1$ and $Ar_2$ by removing one hydrogen atom.

An arylene group having 6 to 30 ring forming carbon atoms and represented by $L_1$ and $L_2$ may be a non-condensed ring or a condensed ring. Examples of an arylene group having 6 to 30 ring forming carbon atoms are a divalent group derived from an aryl group having 6 to 30 ring forming carbon atoms and represented by $Ar_1$ and $Ar_2$ by removing one hydrogen atom.

In order to keep the $T_1$ energy level of the compound in the present invention to be a suitable value, examples of a preferable arylene group are: an o-phenylene group, an m-phenylene group, a p-phenylene group, a naphthalenediyl group, a phenanthrenediyl group, a biphenylene group, a terphenylene group, a quaterphenylene group, a triphenylenediyl group, and a fluorenediyl group.

A heteroarylene group having 5 to 30 ring forming atoms and represented by $L_2$ may be a non-condensed ring or a condensed ring. It is preferable that the ring contains any one of B, N, O, S, Si, P and Se as a ring forming hetero atom. It is more preferable that the ring contains any one of N, O, S, and Si. Preferable rings are: a non-condensed 5-membered ring, a non-condensed 6-membered ring, and a condensed ring composed of 5-membered ring and 6-membered ring.

Examples of a heteroarylene group having 5 to 30 ring forming atoms are derived from: a pyridine ring, a pyrazine ring, a pyrimidine ring, a piperidine ring, a triazine ring, a pyrrole ring, an imidazole ring, a pyrazole ring, a triazole ring, an indole ring, an isoindole ring, a benzimidazole ring, a furan ring, a benzofuran ring, an isobenzofuran ring, a dibenzofuran ring, a thiophene ring, a benzothiophene ring, a dibenzothiophene ring, a silole ring, a benzosilole ring, a dibenzosilole ring, a quinoline ring, an isoquinoline ring, a quinoxaline ring, a phenanthridine ring, a phenanthroline ring, an acridine ring, a phenazine ring, a phenoxazine ring, a phenothiazine ring, a phenoxathin ring, a pyridine ring, a pyrazine ring, a pyrimidine ring, a pyridazine ring, a triazine ring, an acridine ring, an oxazole ring, an oxadiazole ring, a benzoxazole ring, a thiazole ring, a thiadiazole ring, a benzothiazole ring, a benzodifuran ring, a thienothiophene ring, a benzodithiophene ring, a cyclazine ring, a quindoline ring, a tepenidine ring, a quinindoline ring, a triphenodithiadine ring, a triphenodioxazine ring, a phenanthradine ring, an anthrazine ring, a perimidine ring, a naphthofuran ring, a naphthothiophene ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring, a naphthothiophene ring, a carbazole ring, a carboline ring, a diazacarbazole ring (it indicates a ring structure in which arbitral two or more carbon atoms constituting the carbazole ring is replaced with nitrogen atoms), an azadibenzofuran ring (it indicates a ring structure in which arbitral one or more carbon atoms constituting the dibenzofuran ring is replaced with nitrogen atoms), azadibenzothiophene ring (it indicates a ring structure in which arbitral one or more carbon atoms constituting the dibenzothiophene ring is replaced with nitrogen atoms), an indolocarbazole ring, and an indenoindole ring.

A divalent group is derived from the above-described ring by removing two hydrogen atoms from the ring.

More preferable heteroarylene groups are a divalent group derived from the following by removing two hydrogen atoms in the ring: a pyridine ring, a pyrazine ring, a pyrimidine ring, a piperidine ring, a triazine ring, a dibenzofuran ring, a dibenzothiophene ring, a carbazole ring, a carboline ring, a diazacarbazole ring.

The above-described alkylene group, arylene group and heteroarylene group may further have a substituent as long as it does not inhibit the function of the compound of the present invention. As a substituent, it may be the same substituent represented by R', $Ar_1$ and $Ar_2$ as described above.

More preferably, $L_1$ and $L_2$ represent a single bond, a phenylene group, a heteroarylene group, or an alkylene group having 2 carbon atoms or less.

$R_1$ and $R_2$ each independently represent: a substituted or unsubstituted alkyl group having 1 to 12 carbon atoms; a cyano group; a halogen atom; or an unsubstituted or substituted aryl group having 6 to 30 ring forming carbon atoms, provided that the substituted aryl group has a substituent represented by Formulas (A-1) and (A-2).

An alkyl group having 1 to 12 carbon atoms and represented by $R_1$ and $R_2$ may be a straight chain or a branched structure as long as it does not inhibit the function of the compound of the present invention. The alkyl group may be a cyclic structure such as a cycloalkyl group.

As an alkyl group having 1 to 12 carbon atoms, it may be the same alkyl group having 1 to 12 carbon atoms and represented by R', $A_{r}$, and $Ar_2$ as described above.

As a halogen atom represented by $R_1$ and $R_2$, it may be cited: a fluorine atom, a chlorine atom, a bromine atom, and an iodine atom.

An aryl group having 6 to 30 ring forming carbon atoms and represented by $R_1$ and $R_2$ may be a non-condensed or condensed ring. As an aryl group having 6 to 30 ring forming carbon atoms, it may be cited the same aryl group having 6 to 30 ring forming carbon atoms and represented by R', $Ar_1$ and $Ar_2$ as described above.

Preferably, $R_1$ and $R_2$ have no substituent, or when they have a substituent, the substituent is preferably an alkyl group having 4 carbon atoms or less, or an aryl group.

An aryl group represented by $R_1$ and $R_2$ may have a substituent represented by Formulas (A-1) and (A-2).

Formula (A-1)

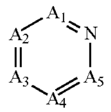

Formula (A-2)

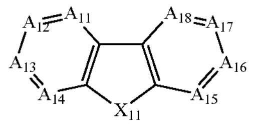

In Formula (A-1), $A_1$ to $A_5$ each independently represent CRc or a nitrogen atom. Provided that one of $A_1$ to $A_5$ represents CRc, and Rc represents a single bond which is directly bonded to an aryl group having 6 to 30 ring forming carbon atoms and represented by $R_1$ and $R_2$.

Preferably, 3 to 5 of $A_1$ to $A_5$ represent CRc. More preferably, a structure represented by Formula (A-1) is a pyridyl ring, a pyrimidine ring, or a triazine ring.

In Formula (A-2), $A_{11}$ to $A_{18}$ each independently represent CRc or a nitrogen atom. Provided that one of $A_1$ to $A_5$ represents CRc, and Rc represents a single bond which is directly bonded to an aryl group represented by $R_1$ and $R_2$.

Preferably, 6 to 8 of $A_1$ to $A_{18}$ represent CRc. More preferably, 7 to 8 of $A_{11}$ to $A_{18}$ represent CRc. Still more preferably all of $A_{11}$ to $A_{18}$ represent CRc.

Rc represents a hydrogen atom, or a substituent other than a bond. The substituent represented by Rc is not limited in particular as long as it does not inhibit the function of the compound of the present invention. The substituent may be actively used for finely adjusting to obtain an effect of the present invention.

As a substituent represented by Rc, it may be the same substituent represented by Ra and Rb in Formulas (1), (2), (3) and (4) as described above.

A plurality of Rc may be the same or different, and adjacent Rc may be bonded together to form a ring structure.

Preferably, Rc represents an alkyl group, an aryl group, or a heteroaryl group.

In Formulas (1), (2), (3) and (4). $R_3$ represents: a substituted or unsubstituted alkyl group having 1 to 12 carbon atoms; a substituted or unsubstituted aryl group having 6 to 30 ring forming carbon atoms; or a substituted or unsubstituted heteroaryl group having 5 to 30 ring forming atoms.

As an alkyl group having 1 to 12 carbon atoms, it may be the same alkyl group having 1 to 12 carbon atoms and represented by R', Art, and $Ar_2$ as described above.

As an aryl group having 6 to 30 ring forming carbon atoms, it may be the same aryl group having 6 to 30 ring forming carbon atoms and represented by R', $Ar_1$, and $Ar_2$ as described above.

In order to keep the $T_1$ energy level of the compound in the present invention to be a suitable value, examples of a more preferable aryl group are: a phenyl group, a naphthyl group, a phenanthryl group, a biphenyl group, a terphenyl group, a quaterphenyl group, a triphenylenyl group, and a fluorenyl group.

A heteroaryl group (aromatic heterocyclic group) having 5 to 30 ring forming atoms may be a non-condensed ring or a condensed ring. It is preferable that the ring contains any one of B, N, O, S, Si, P and Se as a ring forming hetero atom. It is more preferable that the ring contains any one of N, O, S, and Si. Preferable rings are: a non-condensed 5-membered ring, a non-condensed 6-membered ring, and a condensed ring composed of 5-membered ring and 6-membered ring.

Examples of a heteroaryl group having 5 to 30 ring forming atoms are derived from: a pyridine ring, a pyrazine ring, a pyrimidine ring, a piperidine ring, a triazine ring, a pyrrole ring, an imidazole ring, a pyrazole ring, a triazole ring, an indole ring, an isoindole ring, a benzimidazole ring, a furan ring, a benzofuran ring, an isobenzofuran ring, a dibenzofuran ring, a thiophene ring, a benzothiophene ring a dibenzothiophene ring, a silole ring, a benzosilole ring, a dibenzosilole ring, a quinoline ring, an isoquinoline ring, a quinoxaline ring, a phenanthridine ring, a phenanthroline ring, an acridine ring, a phenazine ring, a phenoxazine ring, a phenothiazine ring, a phenoxathin ring, a pyridine ring, a pyrazine ring, a pyrimidine ring, a pyridazine ring, a triazine ring, an acridine ring, an oxazole ring, an oxadiazole ring, a benzoxazole ring, a thiazole ring, a thiadiazole ring, a benzothiazole ring, a benzodifuran ring, a thienothiophene ring, a benzodithiophene ring, a cyclazine ring, a quindoline ring, a tepenidine ring, a quinindoline ring, a triphenodithiadine ring, a triphenodioxazine ring, a phenanthradine ring, an anthrazine ring, a perimidine ring, a naphthofuran ring, a naphthothiophene ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring, a naphthothiophene ring, a carbazole ring, a carboline ring, a diazacarbazole ring (it indicates a ring structure in which arbitral two or more carbon atoms constituting the carbazole ring is replaced with nitrogen atoms), an azadibenzofuran ring (it indicates a ring structure in which arbitral one or more carbon atoms constituting the dibenzofuran ring is replaced with nitrogen atoms), azadibenzothiophene ring (it indicates a ring structure in which arbitral one or more carbon atoms constituting the dibenzothiophene ring is replaced with nitrogen atoms), an indolocarbazole ring, and an indenoindole ring.

A group is derived from the above-described ring by removing one hydrogen atom from the ring.

More preferable heteroaryl groups are a group derived from the following by removing one hydrogen atoms in the ring: a pyridine ring, a pyrazine ring, a pyrimidine ring, a piperidine ring, a triazine ring, a dibenzofuran ring, a dibenzothiophene ring, a carbazole ring, a carboline ring, a diazacarbazole ring.

The above-described alkyl group, aryl group, and heteroaryl group may have a substituent as long as it does not inhibit the function of the compound of the present invention. As a substituent, it may be the same substituent represented by R'. $Ar_1$ and $Ar_2$ as described above.

In Formulas (1), (2), (3), and (4), n1, na1, and nb1 each independently represent an integer of 0 to 3, na2 represents an integer of 0 to 2, and n2, n3, n4, and nb2 each independently represent an integer of 0 to 4.

More preferably, n1 to n4 represent an integer of 1, and na1, nb1, na2 and nb2 represent an integer of 1.

It will be described a preferable bonding position of the condensed ring containing X to which is bonded $L_1$ or $L_2$ in Formulas (1), (2), (3), and (4). The bonding position of the condensed ring containing X is indicated as a number in Formula (I).

Formula (I)

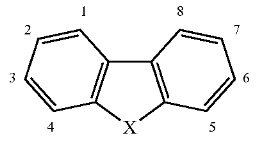

In Formula (1), $L_1$ is preferably bonded to positions 2, 3 or 4 in a condensed ring containing X More preferably. $L_1$ is bonded to positions 2 or 4. $L_2$ is preferably bonded to positions 5, 6 or 7. More preferably, $L_2$ is bonded to positions 5 or 7.

In Formula (2), $L_1$ is preferably bonded to positions 2, 3 or 4 in a condensed ring containing X More preferably, $L_1$ is bonded to positions 2 or 4. $L_2$ is preferably bonded to positions 5, 6 or 7. More preferably, $L_2$ is bonded to positions 5 or 7.

In Formula (3), $L_1$ is preferably bonded to positions 2, 3 or 4 in a condensed ring containing X More preferably. $L_1$ is bonded to positions 2 or 4. $L_2$ is preferably bonded to positions 2, 3 or 4. More preferably, $L_2$ is bonded to positions 2 or 4.

In Formula (4), $L_1$ is preferably bonded to positions 2, 3 or 4 in a condensed ring containing X. More preferably, $L_1$ is bonded to positions 2 or 4. $L_2$ is preferably bonded to positions 2, 3 or 4. More preferably, $L_2$ is bonded to positions It will be described a preferable bonding position of a carbazole ring to which is bonded L of Formulas (1) or (3). The bonding position of the carbazole ring is indicated as a number in Formula (II).

Formula (II)

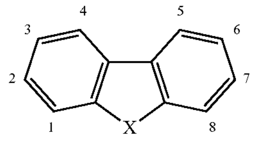

In Formula (1), $L_1$ is preferably bonded to positions 2 or 3 in a carbazole ring. More preferably, $L_1$ is bonded to position 3.

In Formula (3), $L_1$ is preferably bonded to positions 2 or 3 in a carbazole ring. More preferably, $L_1$ is bonded to position 3.

In Formulas (1), (2), (3), and (4), favorability of the bonding position of $L_1$ and $L_2$ contains the view of exhibiting a function of a compound of the present invention. In addition, it contains the synthetic views of stably obtaining the product with 1a cost such as: a synthetic step number, reaction easiness, purification easiness, and raw material cost.

An aromatic heterocyclic derivative represented by Formulas (1), (2), (3), and (4) is preferably represented by the following Formulas (1-1) to (1-4), (2-1) to (2-4), (3-1), (3-2), (4-1), and (4-2).

-continued
Formula (1-1)
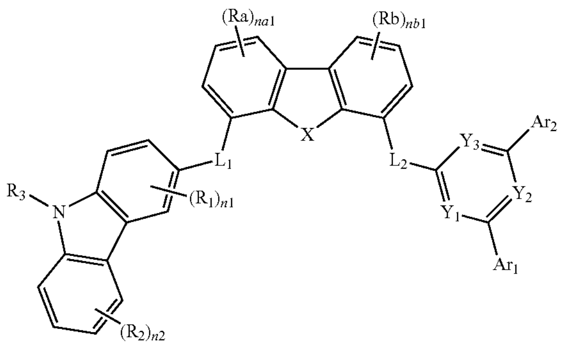
Formula (1-2)
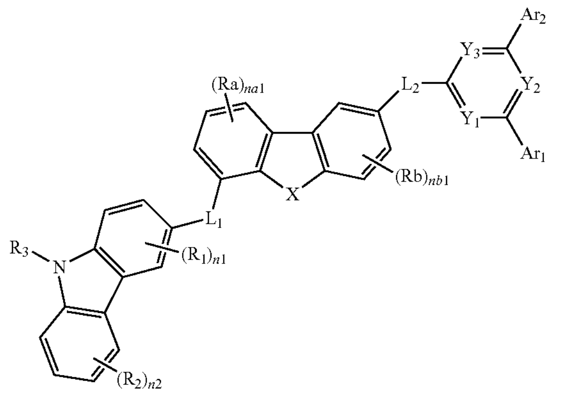
Formula (1-3)
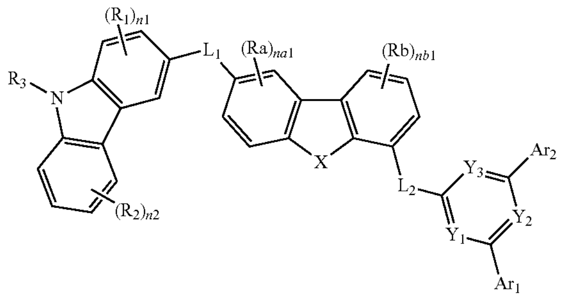
Formula (1-4)
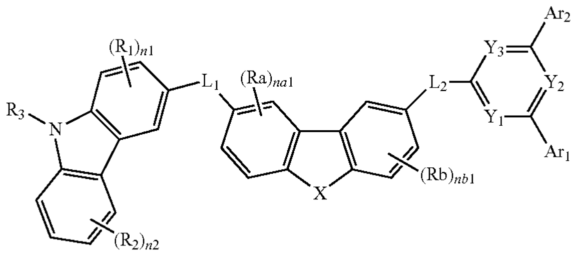
Formula (2-1)
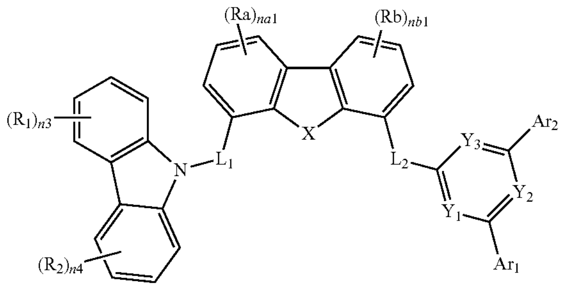
Formula (2-2)
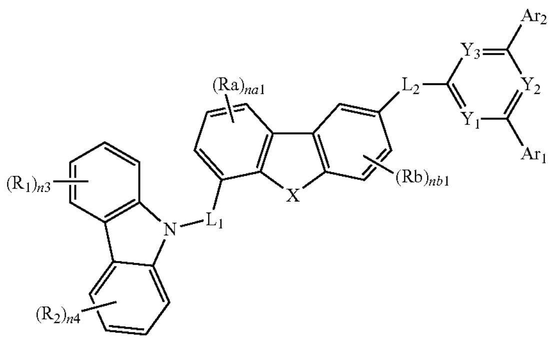
Formula (2-3)
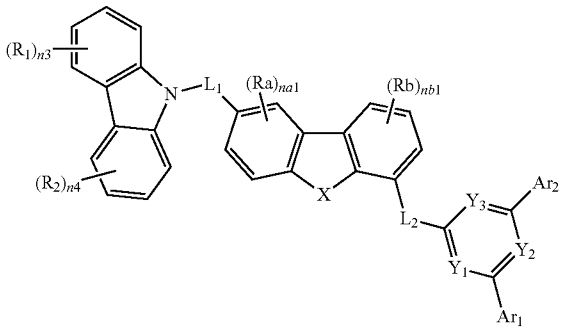
Formula (2-4)
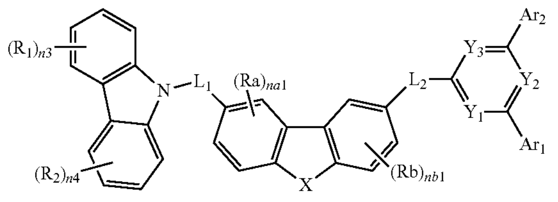

-continued

Formula (3-1)

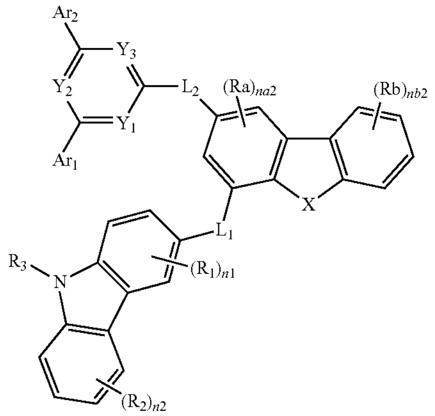

Formula (3-2)

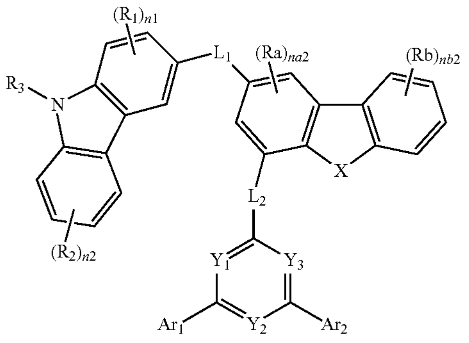

Formula (4-1)

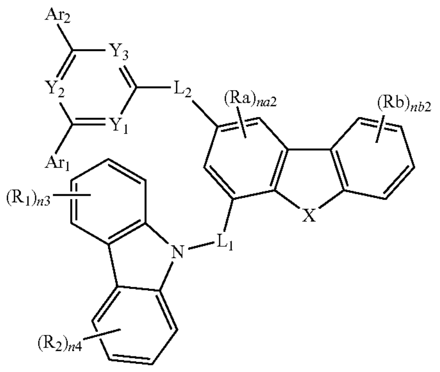

Formula (4-2)

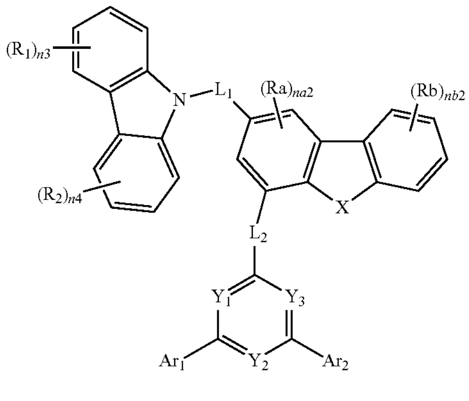

$Y_1$, $Y_2$, $Y_3$, $Ar_1$, $Ar_2$, X, Ra, Rb, $L_1$, $L_2$, $R_1$, $R_2$, $R_3$, n1 to n4, na1, nb1, na2 and nb2 in Formulas (1-1) to (1-4), (2-1) to (2-4), (3-1), (3-2), (4-1), and (4-2) are synonymous with $Y_1$, $Y_2$, $Y_3$, $Ar_1$, $Ar_2$, X, Ra, Rb, $L_1$, $L_2$, $R_1$, $R_2$, $R_3$, n1 to n4, na1, nb1, na2 and nb2 in Formulas (1), (2), (3), and (4).

Specific examples of a compound having a structure represented by Formulas (1), (2), (3), and (4) are listed in the following. However, the present invention is not limited to them. Formulas (1), (2), (3), and (4) are further described using Formula (A1) to Formula (P3).

$Y_1$, $Y_2$, $Y_3$, $Ar_1$, $Ar_2$, X, Ra, Rb, $L_1$, $L_2$, $R_1$, $R_2$, and $R_3$ in Formula (A1) to Formula (P3) are synonymous with $Y_1$, $Y_2$, $Y_3$, $Ar_1$, $Ar_2$, X. Ra, Rb, $L_1$, $L_2$, $R_1$, $R_2$, and $R_3$ in Formulas (1), (2), (3), and (4).

In Tables, a sign "-" in the columns $L_1$ and $L_2$ indicates a single bond, and a sign "-" in the columns Ra. Rb, $R_1$, and $R_2$ indicates that there is no substituent. The figure in the parentheses in Tables indicates the bonding position of the substituent. A sign "-" in the columns $Ar_1$ and $Ar_2$ indicates that $Ar_1$ and $Ar_2$ are a hydrogen atom.

Formula (A1)

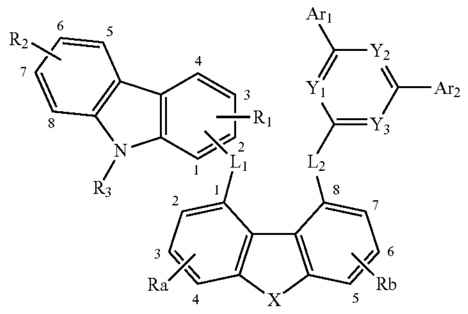

Formula (A2)

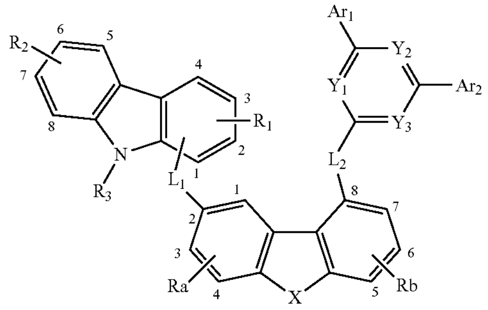

Formula (A3)

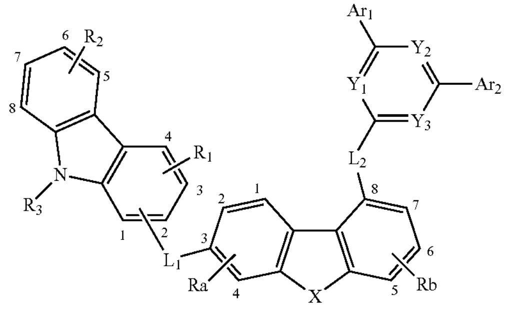

-continued
Formula (A4)
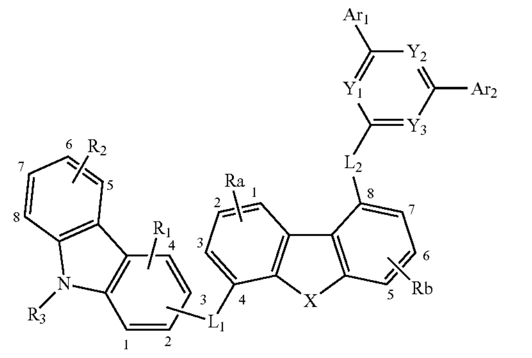
Formula (B1)
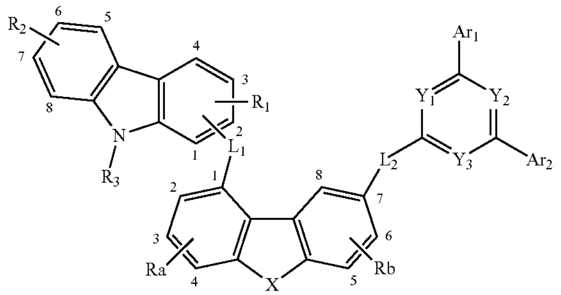
Formula (B2)
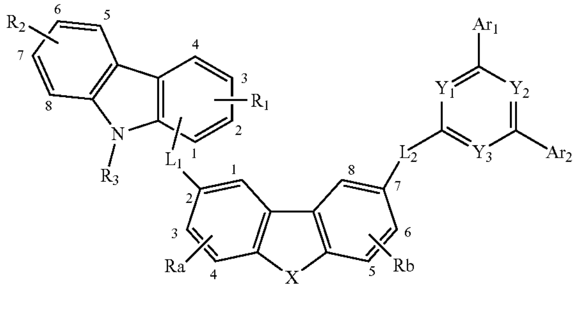
Formula (B3)
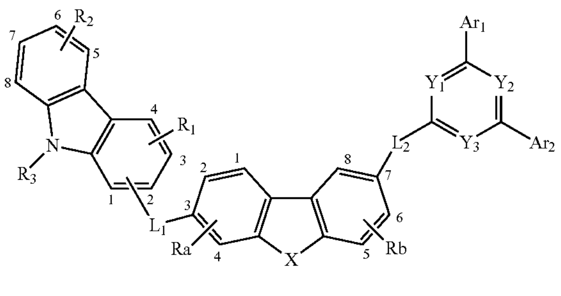
-continued
Formula (B4)
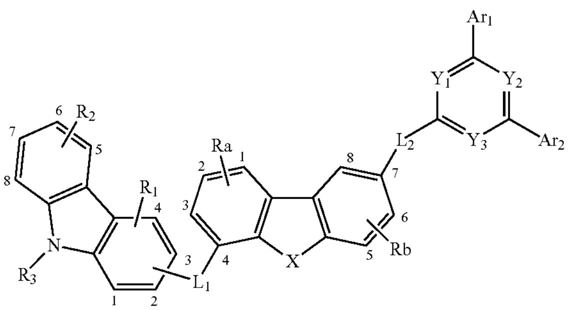
Formula (C1)
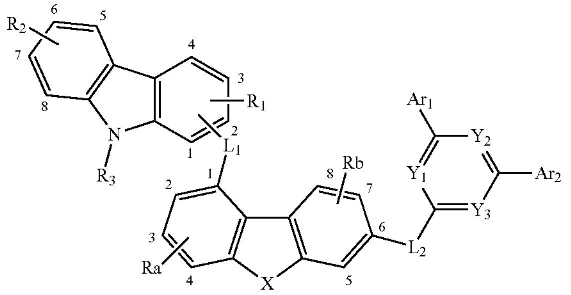
Formula (C2)
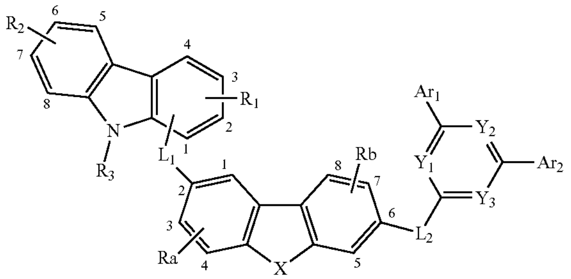
Formula (C3)
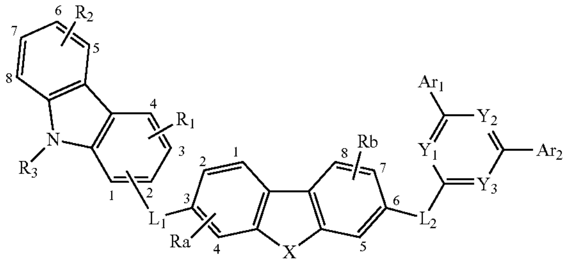
Formula (C4)
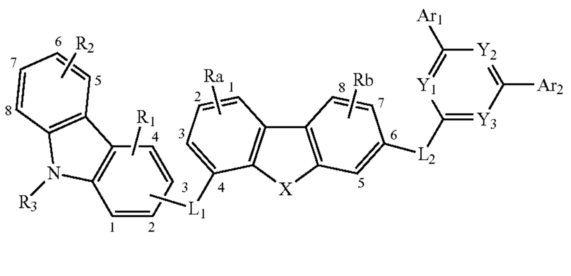

-continued
Formula (D1)
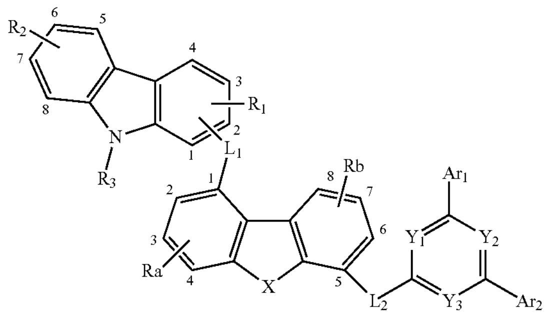
Formula (D2)
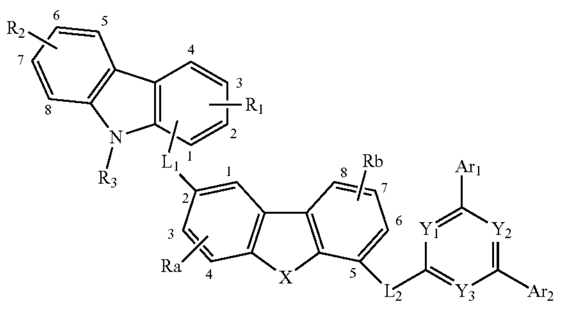
Formula (D3)
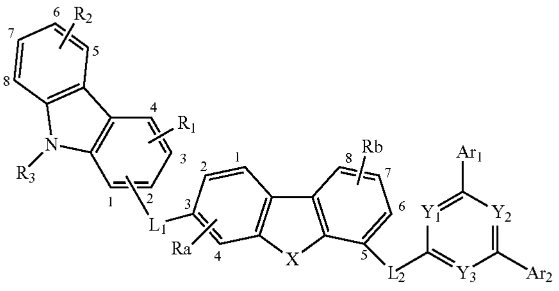
Formula (D4)
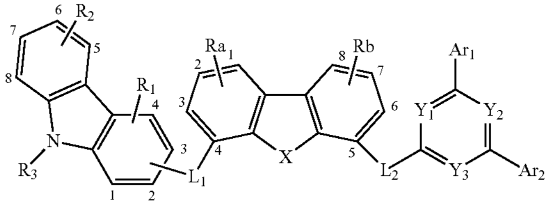
Formula (E1)
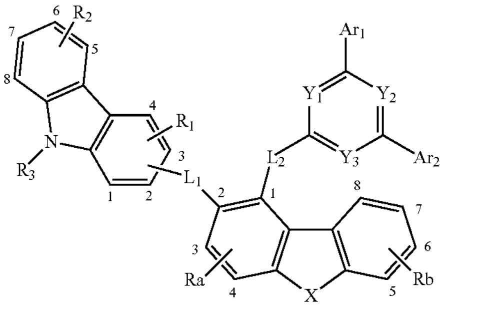
-continued
Formula (E2)
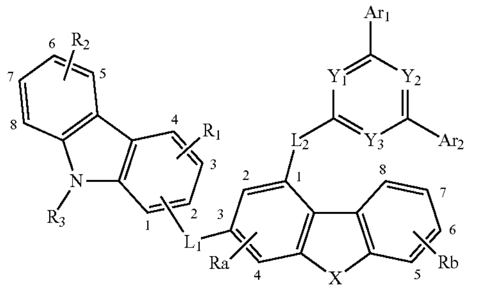
Formula (E3)
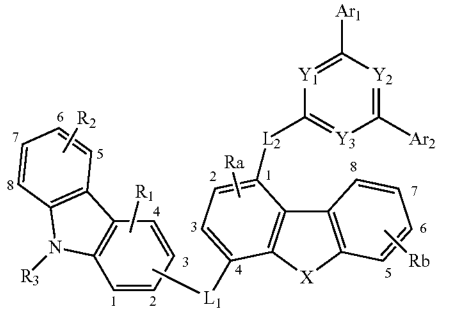
Formula (F1)
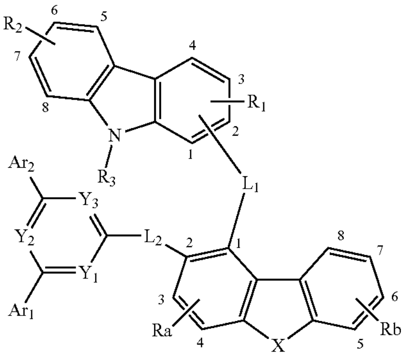
Formula (F2)
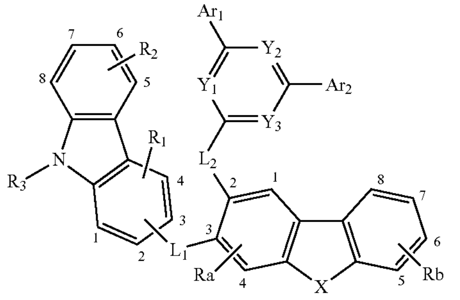

-continued
Formula (F3)
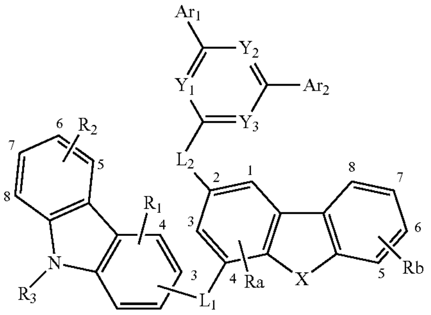
Formula (G1)
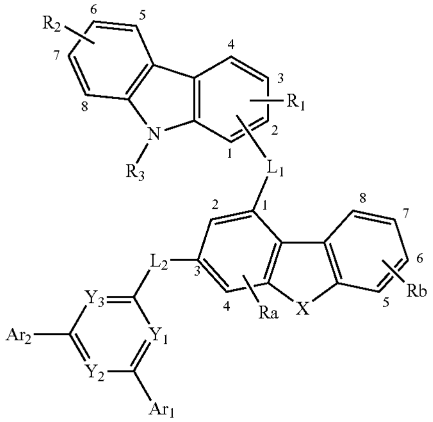
Formula (G2)
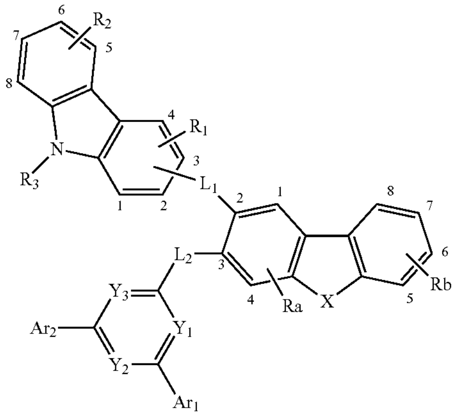
-continued
Formula (G3)
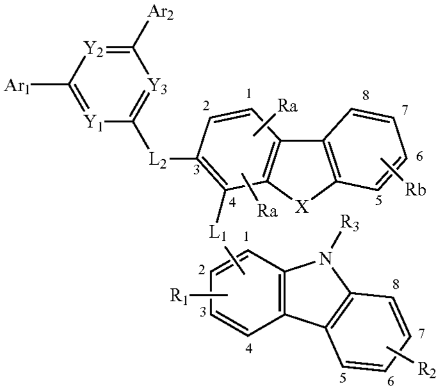
Formula (H1)
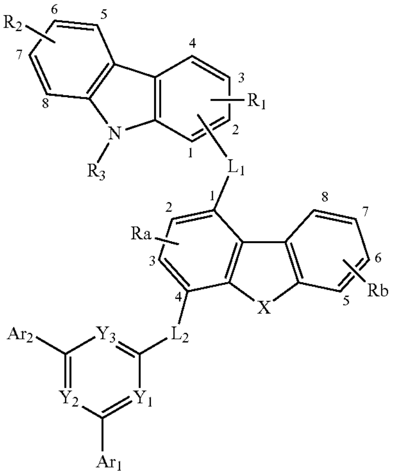
Formula (H2)
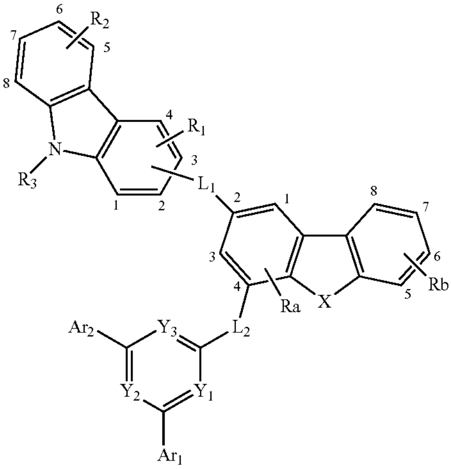

-continued
Formula (H3)
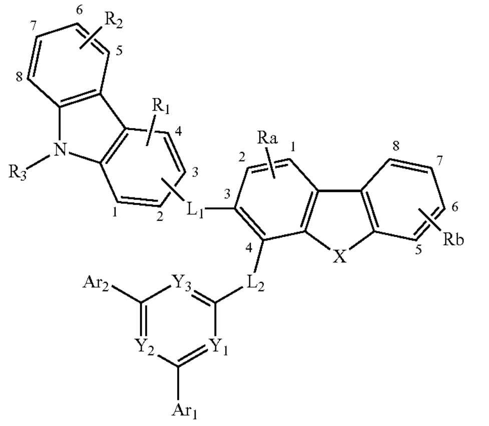
Formula (I1)
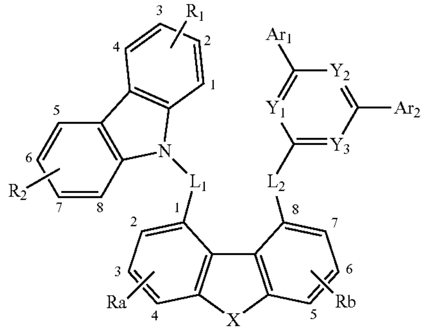
Formula (I2)
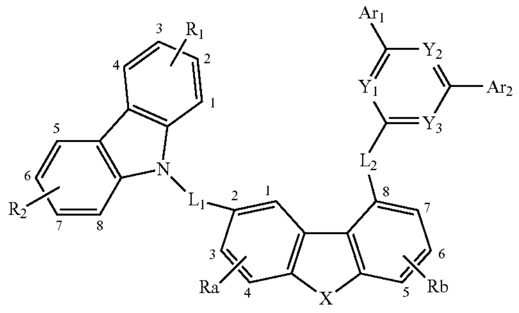
Formula (I3)
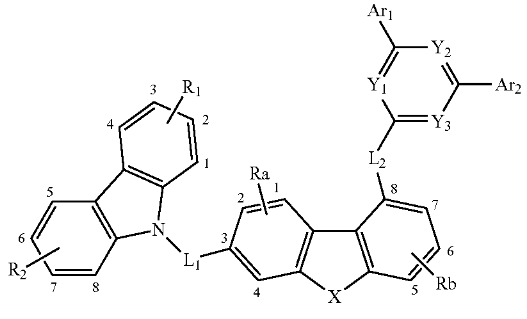
-continued
Formula (I4)
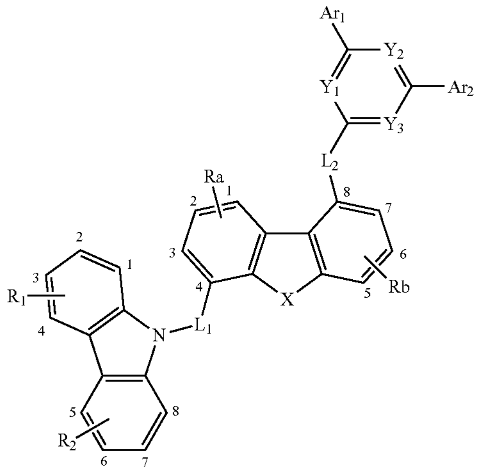
Formula (J1)
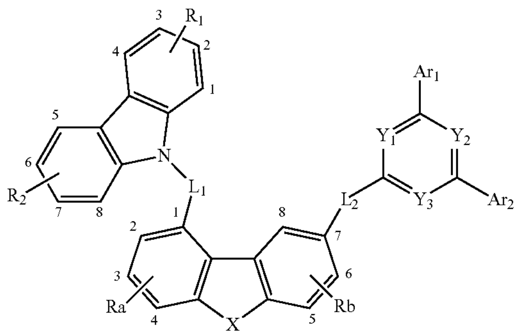
Formula (J2)
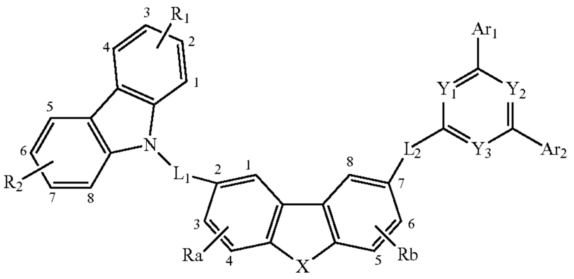
Formula (J3)
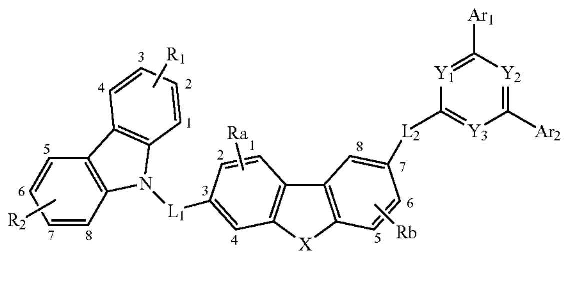

-continued
Formula (J4)
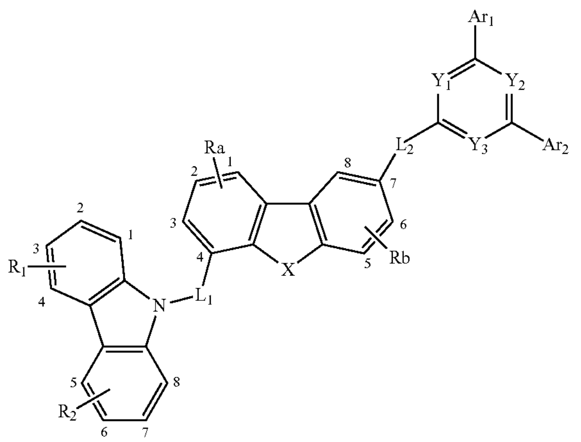
Formula (K1)
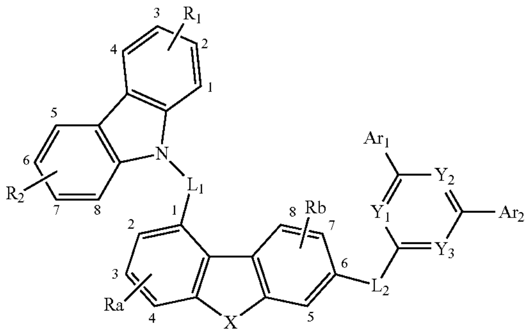
Formula (K2)
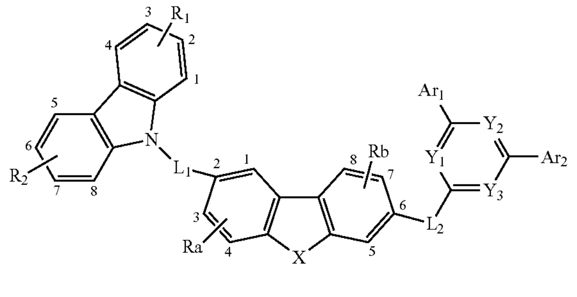
Formula (K3)
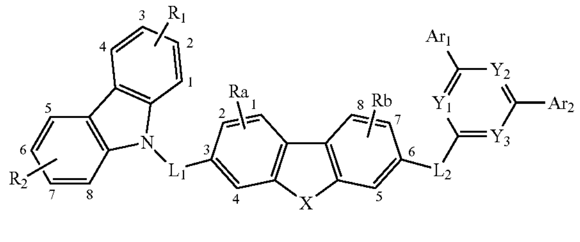
-continued
Formula (K4)
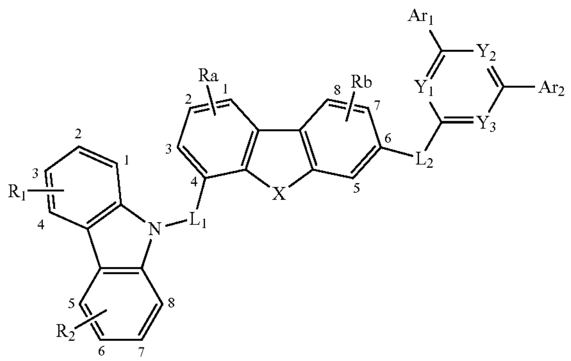
Formula (L1)
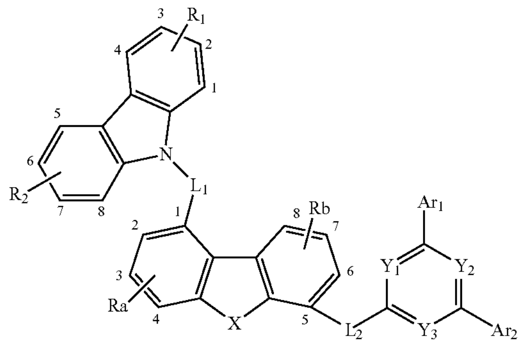
Formula (L2)
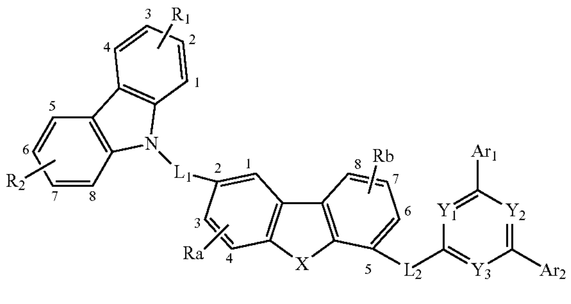
Formula (L3)
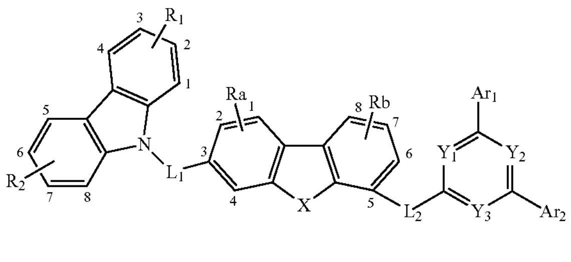

-continued
Formula (L4)
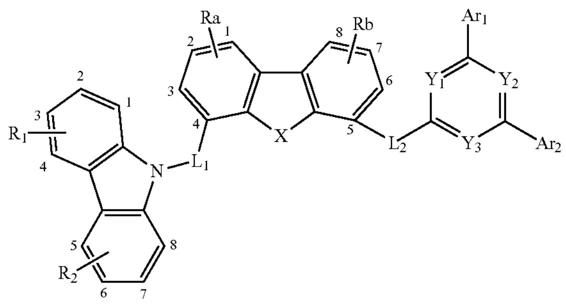
Formula (M1)
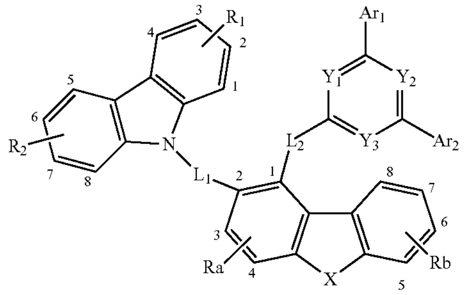
Formula (M2)
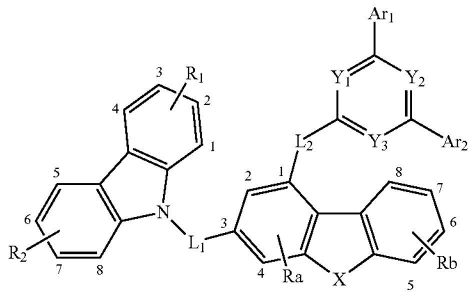
Formula (M3)
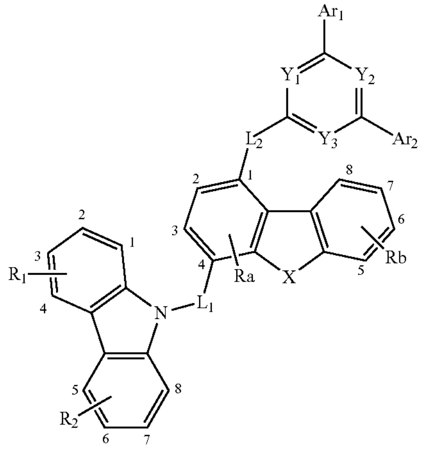
-continued
Formula (N1)
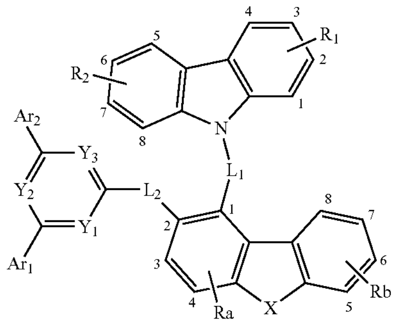
Formula (N2)
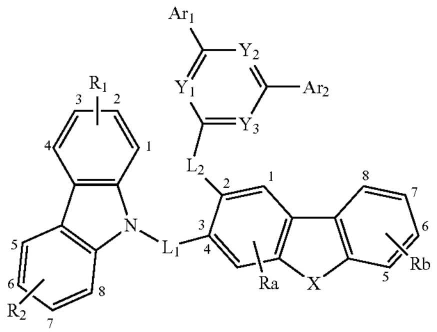
Formula (N3)
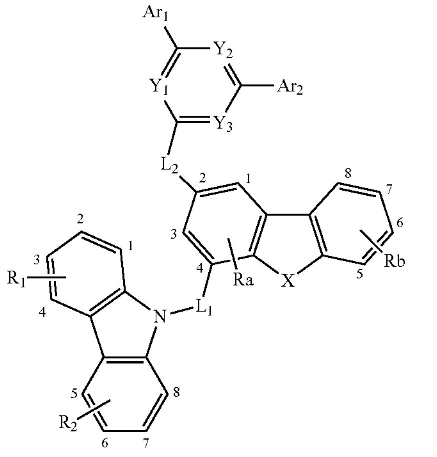
Formula (O1)
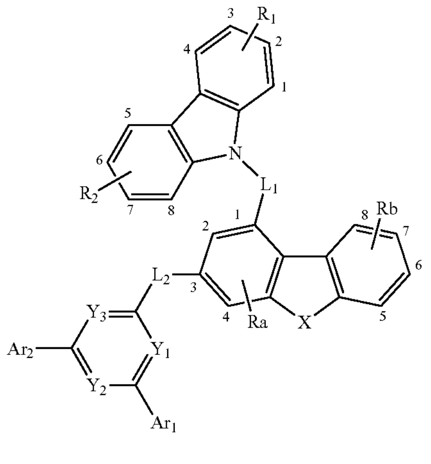

-continued
Formula (O2)
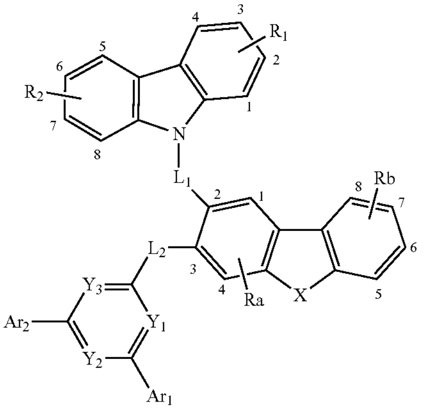
Formula (O3)
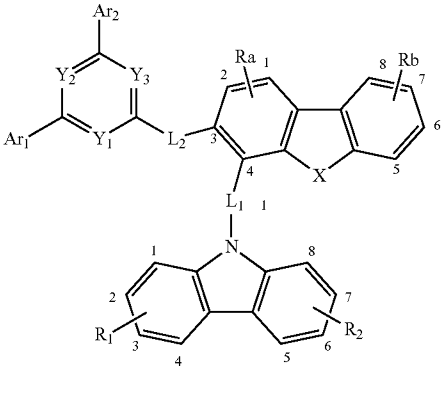
-continued
Formula (P1)
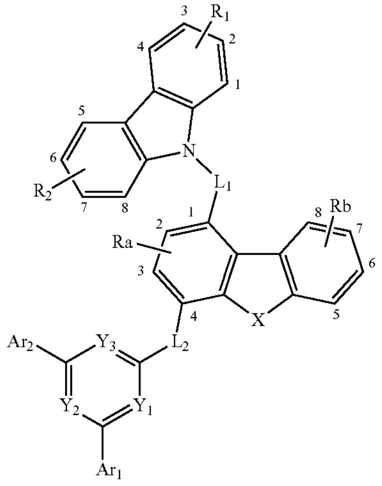
Formula (P2)
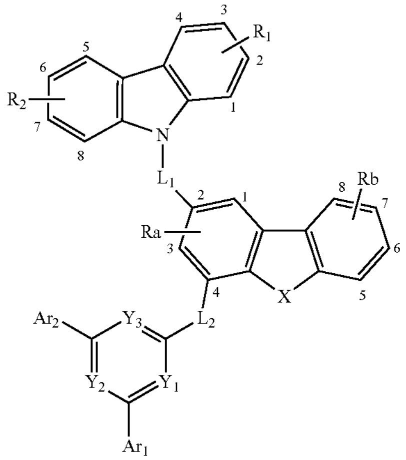
Formula (P3)
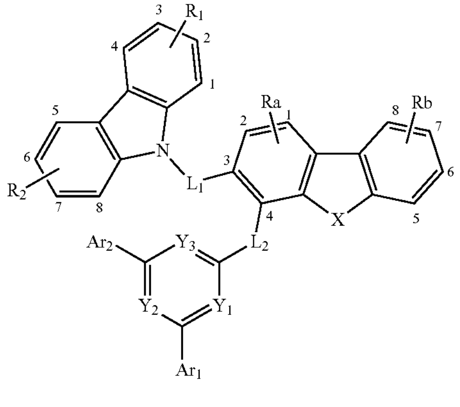

Formura (A1)
| Compound No. | X | $L_1$ | $L_2$ | $Y_1$ | $Y_2$ | $Y_3$ | $Ar_1$ |
|---|---|---|---|---|---|---|---|
| 1 | O | — | 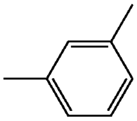 | N | N | N | —Ph |
| 2 | O | — | — | N | N | N | —Ph |
| 3 | S | — | — | N | N | CH | —Ph |
| 4 | S | 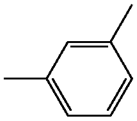 | — | N | C—Ph | N | —Ph |
| 5 | O | — | — | N | N | N | —Ph |
| 6 | S | 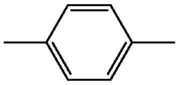 | — | N | N | N | 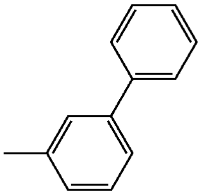 |
| 7 | O | 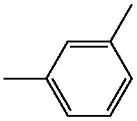 | 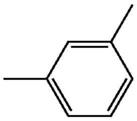 | N | CH | N | —Ph |
| 8 | O | — | 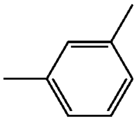 | CH | CH | N | —Ph |
| Compound No. | $Ar_2$ | $R_1$ | $R_2$ | Bonding position of $L_1$ | $R_3$ | Ra | Rb |
|---|---|---|---|---|---|---|---|
| 1 | —Ph | — | — | 3 | —Ph | — | — |
| 2 | —Ph | — | — | 3 | —Ph | — | — |
| 3 | —Ph | — | — | 3 | —Ph | — | — |
| 4 | — | — | — | 3 | 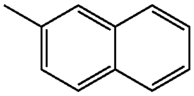 | — | — |
| 5 | —Ph | — | —Et (6) | 3 | —Ph | — | — |
| 6 | 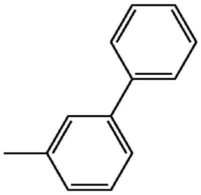 | — | —Ph (6) | 3 | —Ph | — | — |
| 7 | —Ph | — | — | 3 | —Me | — | — |
| 8 | —Ph | — | — | 2 | —Ph | — | — |

| Formula (A2) | | | | | | | | | | | | | | |
|---|---|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
| 9 | O | — | 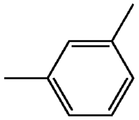 | N | N | N | —Ph | —Ph | — | — | 3 | —Ph | — | — |
| 10 | O | — | — | N | N | N | —Ph | —Ph | — | — | 3 | —Ph | — | — |
| 11 | O | — | — | N | N | CH | —Ph | —Ph | — | — | 3 | —Ph | — | — |
| 12 | O | 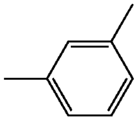 | — | N | C—Ph | N | —Ph | | — | — | 3 | —Ph | — | — |
| 13 | O | — | — | N | N | N | —Ph | —Ph | — | — | 3 | —Ph | — | — |
| 14 | O | 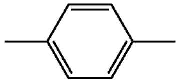 | — | N | N | N | 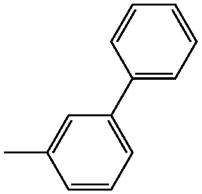 | 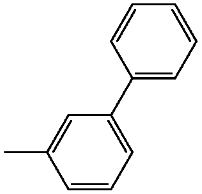 | — | —Ph (6) | 3 | —Ph | — | — |
| 15 | O | 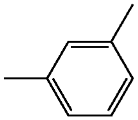 | 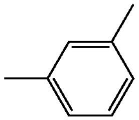 | N | N | N | —Ph | —Ph | — | — | 3 | —Ph | — | — |

-continued
| Formula (A2) | | | | | | | | | | | | | |
|---|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
| 16 | S | — | 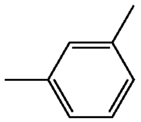 | N | N | N | —Ph | —Ph | — | — | 2 | —iPr | — | — |
| 17 | O | — | — | N | N | N | —tBu | —tBu | — | — | 3 | —Ph | — | — |
| 18 | S | — | — | N | N | N | 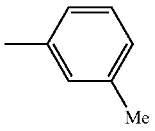 | 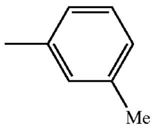 | — | — | 3 | —Ph | — | — |
| 19 | S | $—CH_2—$ | — | N | N | N | —Ph | —Ph | — | — | 3 | —Ph | — | — |
| 20 | O | 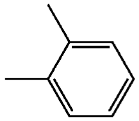 | — | N | N | N | —Ph | —Ph | — | — | 3 | —Ph | — | — |

Formula (A3)
| Compound No. | X | $L_1$ | $L_2$ | $Y_1$ | $Y_2$ | $Y_3$ | $Ar_1$ |
|---|---|---|---|---|---|---|---|
| 21 | O | — | 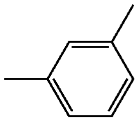 | N | N | N | —Ph |
| 22 | O | — | — | N | N | N | —Ph |
| 23 | S | — | — | N | N | CH | —Ph |
| 24 | S | 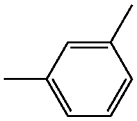 | — | N | C—Ph | N | —Ph |
| 25 | O | — | — | N | N | N | —Ph |
| 26 | S | 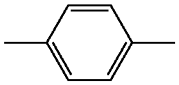 | — | N | N | N | 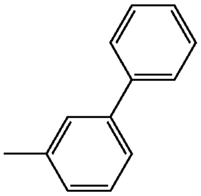 |
| 27 | O | 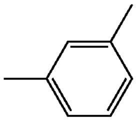 | 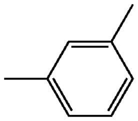 | N | CH | N | —Ph |
| 28 | O | — | 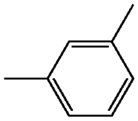 | CH | CH | N | —Ph |
| Compound No. | $Ar_2$ | $R_1$ | $R_2$ | Bonding position of $L_1$ | $R_3$ | Ra | Rb |
|---|---|---|---|---|---|---|---|
| 21 | —Ph | — | — | 3 | —Ph | — | — |
| 22 | —Ph | — | — | 3 | —Ph | — | — |
| 23 | —Ph | — | — | 3 | —Ph | — | — |
| 24 | — | — | — | 3 | —Ph | — | — |
| 25 | —Ph | — | 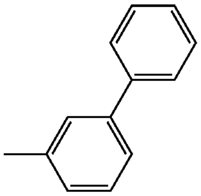 | 3 | —Ph | — | — |
(6)

-continued
Formula (A3)
| | | | | | | | |
|---|---|---|---|---|---|---|---|
| 26 | 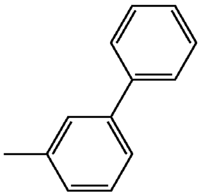 | — | —Ph (6) | 3 | —Ph | — | — |
| 27 | —Ph | — | — | 3 | —Ph | — | — |
| 28 | —Ph | — | — | 2 | —Ph | — | — |
Formula (A4)
| Compound No. | X | $L_1$ | $L_2$ | $Y_1$ | $Y_2$ | $Y_3$ | $Ar_1$ |
|---|---|---|---|---|---|---|---|
| 29 | O | — | 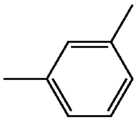 | N | N | N | —Ph |
| 30 | O | — | — | N | N | N | —Ph |
| 31 | O | — | — | N | N | CH | —Ph |
| 32 | O | 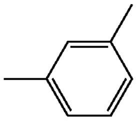 | — | N | C—Ph | N | —Ph |
| 33 | O | — | — | N | N | N | —Ph |
| 34 | O | 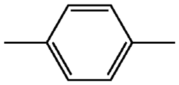 | — | N | N | N | 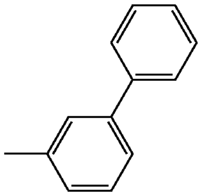 |
| 35 | O | 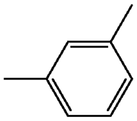 | 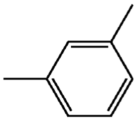 | N | N | N | —Ph |
| 36 | S | — | 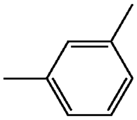 | N | N | N | —Ph |
| 37 | O | — | — | N | N | N | —tBu |
| 38 | S | — | — | N | N | N | 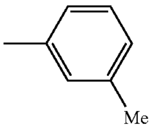 |

-continued
| | | | | | | | |
|---|---|---|---|---|---|---|---|
| Formula (A4) | | | | | | | |
| 39 | S | —$CH_2$— | — | N | N | N | —Ph |
| 40 | O | 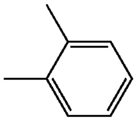 | — | N | N | N | —Ph |
| Compound No. | $Ar_2$ | $R_1$ | $R_2$ | Bonding position of $L_1$ | $R_3$ | Ra | Rb |
|---|---|---|---|---|---|---|---|
| 29 | —Ph | — | — | 3 | —Ph | — | — |
| 30 | —Ph | — | —Ph (6) | 3 | —Ph | — | — |
| 31 | —Ph | — | — | 3 | —Ph | — | — |
| 32 | — | — | — | 3 | —Ph | — | — |
| 33 | —Ph | — | — | 3 | —Ph | — | — |
| 34 | 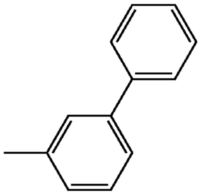 | — | —Ph (6) | 3 | —Ph | — | — |
| 35 | —Ph | — | — | 3 | —Ph | — | — |
| 36 | —Ph | — | — | 2 | —Ph | — | — |
| 37 | —tBu | — | — | 3 | —Ph | — | — |
| 38 | 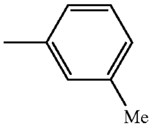 | — | — | 3 | —Ph | — | —Me (7) |
| 39 | —Ph | — | — | 3 | 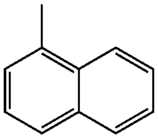 | — | — |
| 40 | —Ph | — | — | 3 | —Ph | — | — |

Formula (B1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 41 | O | — | 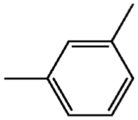 | N | N | N | —Ph | —Ph | — | — | 3 | —Ph | — | — |
| 42 | O | — | — | N | N | N | —Ph | —Ph | — | — | 3 | —Ph | — | — |
| 43 | S | — | — | N | N | CH | —Ph | —Ph | — | — | 3 | —Ph | — | — |
| 44 | S | | — | N | C—Ph | N | —Ph | — | — | — | 3 | —Ph | — | — |
| 45 | O | — | — | N | N | N | —Ph | —Ph | — | — | 3 | —Ph | —Ph (4) | — |
| 46 | S | 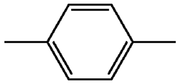 | — | N | N | N | 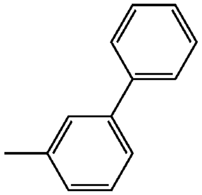 | 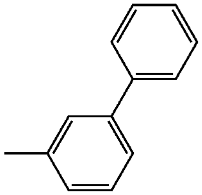 | — | —Ph (6) | 3 | —Ph | — | — |
| 47 | O | 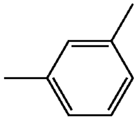 | 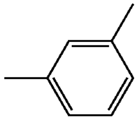 | N | CH | N | —Ph | —Ph | — | — | 3 | —Ph | — | — |
| 48 | S | — | 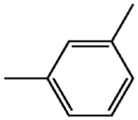 | CH | CH | N | —Ph | —Ph | — | — | 3 | —Ph | — | — |

Formula (B2)
| Compound No. | X | $L_1$ | $L_2$ | $Y_1$ | $Y_2$ | $Y_3$ | $Ar_1$ |
|---|---|---|---|---|---|---|---|
| 49 | O | — | 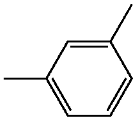 | N | N | N | —Ph |
| 50 | O | 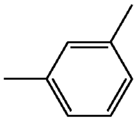 | — | N | N | N | —Ph |
| 51 | O | 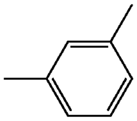 | 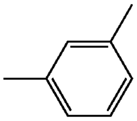 | N | N | N | —Ph |
| 52 | O | 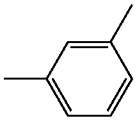 | — | N | N | C—Ph | —Ph |
| 53 | S | 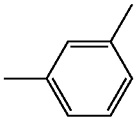 | 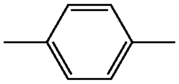 | N | N | N | —Ph |
| 54 | S | — | — | N | N | N | —Ph |
| 55 | O | 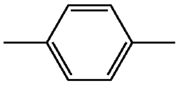 | 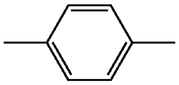 | N | N | N | —Ph |
| 56 | O | 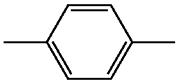 | — | N | N | N | —Ph |
| 57 | O | — | 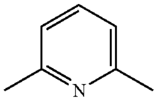 | N | CH | N | —Ph |
| 58 | O | 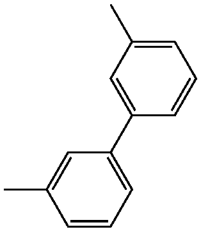 | — | N | N | CH | —Ph |
| 59 | O | 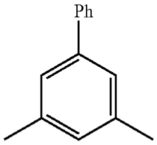 | — | N | N | N | —Ph |
| 60 | O | — | — | N | N | N | —Ph |

-continued
| Formula (B2) | | | | | | | |
|---|---|---|---|---|---|---|---|
| 61 | O | 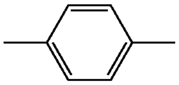 | — | N | N | N | 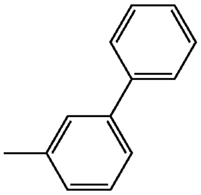 |
| 62 | O | 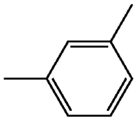 | 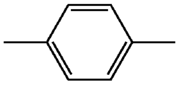 | N | N | N | —Ph |
| 63 | O | — | — | CH | N | N | — |
| 64 | O | — | — | N | C—Ph | N | — |
| 65 | O | — | — | N | N | N | —Ph |
| 66 | O | 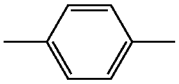 | — | N | N | N | —Ph |
| 67 | O | — | — | N | N | N | —Ph |
| 68 | O | — | — | N | CH | N | —Ph |
| 69 | S | — | 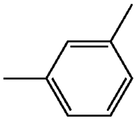 | N | N | N | —Ph |
| 70 | O | — | — | N | N | N | —tBu |
| 71 | S | — | — | N | N | N | —Ph |
| 72 | S | —$CH_2$— | — | N | N | N | 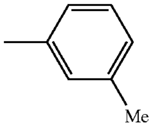 |
| 73 | O | 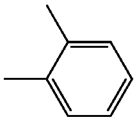 | — | N | N | N | —Ph |
| 74 | O | — | — | N | N | N | 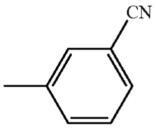 |
| 75 | S | 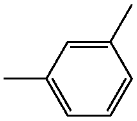 | —$(CH_2)_2$— | N | N | N | —Ph |
| 76 | O | — | — | N | N | N | —Ph |
| 77 | O | — | — | N | N | N | 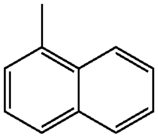 |
| 78 | S | — | — | N | N | N | —iPr |

-continued
Formula (B2)
| | | | | | | | |
|---|---|---|---|---|---|---|---|
| 79 | O | 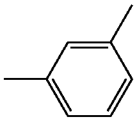 | — | N | N | N | —Ph |
| 80 | O | — | — | N | N | N | —Ph |
| 81 | O | — | — | N | N | N | —Ph |
| 82 | S | — | — | N | N | N | —Ph |
| 83 | O | — | — | N | N | N | —Ph |
| 84 | O | — | — | N | N | N | —Ph |
| 85 | S | — | — | N | N | N | —Ph |
| Compound No. | $Ar_2$ | $R_1$ | $R_2$ | Bonding position of $L_1$ | $R_3$ | Ra | Rb |
|---|---|---|---|---|---|---|---|
| 49 | —Ph | — | — | 3 | —Ph | — | — |
| 50 | —Ph | — | — | 3 | —Ph | — | — |
| 51 | —Ph | — | — | 3 | —Ph | — | — |
| 52 | — | — | — | 3 | — | — | — |
| 53 | —Ph | — | —Ph (6) | 3 | —Ph | — | — |
| 54 | —Ph | — | — | 3 | —Ph | — | — |
| 55 | —Ph | — | — | 3 | —Ph | — | — |
| 56 | —Ph | — | — | 3 | —Ph | — | — |
| 57 | —Ph | — | — | 3 | —Ph | — | — |
| 58 | —Ph | — | — | 3 | —Ph | — | — |
| 59 | —Ph | — | — | 3 | —Ph | — | — |
| 60 | —Ph | — | — | 3 | —Ph | — | — |
| 61 | 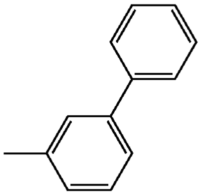 | — | —Ph (6) | 3 | —Ph | — | — |
| 62 | —Ph | — | — | 3 | —Ph | — | — |
| 63 | —Ph | — | — | 3 | —Ph | — | — |
| 64 | — | — | — | 3 | —Ph | — | — |
| 65 | —Ph | — | — | 3 | —Ph | —Ph (4) | — |
| 66 | —Ph | — | — | 3 | —Ph | — | —Ph (5) |
| 67 | 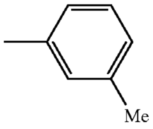 | — | — | 3 | —Ph | — | — |
| 68 | —Ph | — | — | 3 | —Ph | — | — |
| 69 | —Ph | — | — | 2 | —Ph | — | — |
| 70 | —tBu | — | — | 3 | —Ph | — | — |
| 71 | 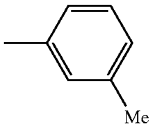 | — | — | 3 | —Ph | — | — |
| 72 | —Ph | — | — | 3 | —Ph | — | — |
| 73 | —Ph | — | — | 3 | —Ph | — | — |
| 74 | 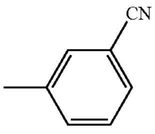 | — | — | 3 | —Ph | — | — |
| 75 | —Ph | — | — | 3 | —Ph | — | — |

-continued
| Formula (B2) | | | | | | | |
|---|---|---|---|---|---|---|---|
| 76 | —Ph | — | —F (6) | 3 | —Ph | — | — |
| 77 | 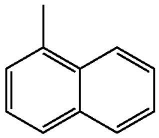 | — | — | 3 | —Ph | — | — |
| 78 | —iPr | — | — | 3 | —Ph | — | — |
| 79 | —Ph | — | — | 3 | —Ph | — | — |
| 80 | —Ph | — | — | 3 | —Ph | — | —Ph (5) |
| 81 | —Ph | — | — | 3 | 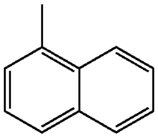 | — | — |
| 82 | —Ph | — | — | 3 | 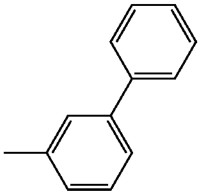 | — | — |
| 83 | —Ph | — | — | 3 | 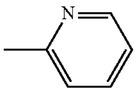 | — | — |
| 84 | —Ph | — | — | 3 | 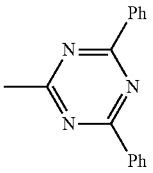 | — | — |
| 85 | —Ph | — | — | 1 | —Ph | — | — |

| Formula (B3) | | | | | | | | | | | | | | |
|---|---|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
| 86 | O | — | 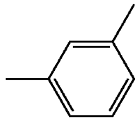 | N | N | N | —Ph | —Ph | — | — | 3 | —Ph | — | — |
| 87 | O | — | — | N | N | N | —Ph | —Ph | — | —iPr (6) | 3 | —Ph | — | — |
| 88 | O | — | — | N | N | CH | —Ph | —Ph | — | — | 3 | —Ph | — | — |
| 89 | O | 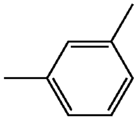 | — | N | C—Ph | N | —Ph | — | — | — | 3 | —Ph | — | — |
| 90 | O | — | — | N | N | N | —Ph | —Ph | — | — | 3 | —Ph | — | — |
| 91 | O | 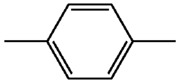 | — | N | N | N | 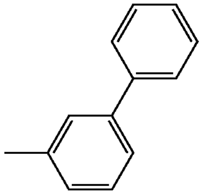 | 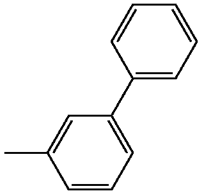 | — | —Ph (6) | 3 | —Ph | — | — |
| 92 | O | 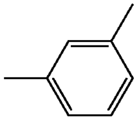 | 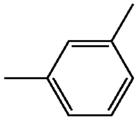 | N | N | N | —Ph | —Ph | — | — | 3 | —Ph | — | — |
| 93 | S | — | 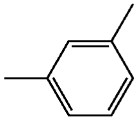 | N | N | N | —Ph | —Ph | — | — | 2 | —Ph | — | — |

-continued
| Formula (B3) | | | | | | | | | | | | | | |
|---|---|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
| 94 | O | — | — | N | N | N | —tBu | —tBu | — | — | 3 | —Ph | — | — |
| 95 | S | — | — | N | N | N | 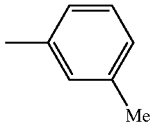 | 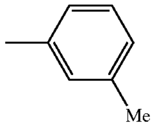 | — | — | 3 | —Ph | — | — |
| 96 | S | —$CH_2$— | — | N | N | N | —Ph | —Ph | — | — | 3 | —Ph | — | — |
| 97 | O | 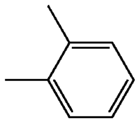 | — | N | N | N | —Ph | —Ph | — | — | 3 | —Ph | — | — |

| Formula (B4) | | | | | | | |
|---|---|---|---|---|---|---|---|
| Compound No. | X | $L_1$ | $L_2$ | $Y_1$ | $Y_2$ | $Y_3$ | $Ar_1$ |
| 98 | O | — | 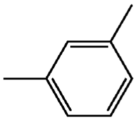 | N | N | N | —Ph |
| 99 | O | 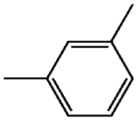 | — | N | N | N | —Ph |
| 100 | O | 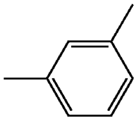 | 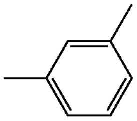 | N | N | N | —Ph |
| 101 | O | 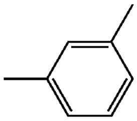 | — | N | N | N | —Ph |
| 102 | S | 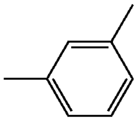 | 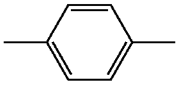 | N | N | N | —Ph |
| 103 | S | — | — | N | N | N | —Ph |
| 104 | O | 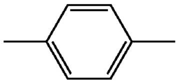 | 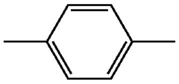 | N | N | N | —Ph |
| 105 | O | 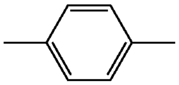 | — | N | N | N | —Ph |
| 106 | O | — | 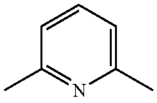 | N | CH | N | —Ph |
| 107 | O | 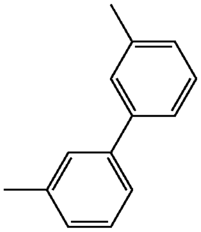 | — | N | N | CH | —Ph |
| 108 | O | 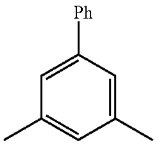 | — | N | N | N | —Ph |
| 109 | O | — | — | N | N | N | —Ph |

-continued
| Formula (B4) | | | | | | | |
|---|---|---|---|---|---|---|---|
| 110 | O | 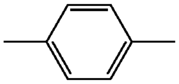 | — | N | N | N | 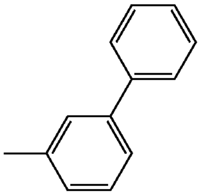 |
| 111 | O | 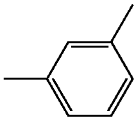 | 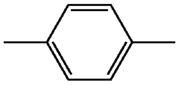 | N | N | N | —Ph |
| 112 | O | — | — | CH | N | N | — |
| 113 | O | — | — | N | C—Ph | N | — |
| 114 | O | — | — | N | N | N | —Ph |
| 115 | O | 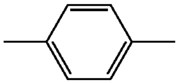 | — | N | N | N | —Ph |
| 116 | O | — | — | N | N | N | —Ph |
| 117 | O | — | — | N | CH | N | —Ph |
| 118 | S | — | 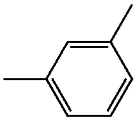 | N | N | N | —Ph |
| 119 | O | — | — | N | N | N | —tBu |
| 120 | S | — | — | N | N | N | —Ph |
| 121 | S | $—CH_2—$ | — | N | N | N | 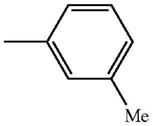 |
| 122 | O | 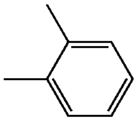 | — | N | N | N | —Ph |
| 123 | O | — | — | N | N | N | 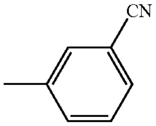 |
| 124 | S | 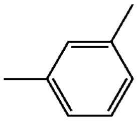 | $—(CH_2)_2—$ | N | N | N | —Ph |
| 125 | O | — | — | N | N | N | —Ph |
| 126 | O | — | — | N | N | N | 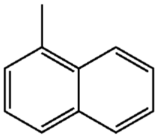 |
| 127 | S | — | — | N | N | N | —iPr |

-continued
Formula (B4)
| | | | | | | | |
|---|---|---|---|---|---|---|---|
| 128 | O | 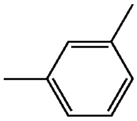 | — | N | N | N | —Ph |
| 129 | O | — | — | N | N | N | —Ph |
| 130 | O | — | — | N | N | N | —Ph |
| 131 | O | — | — | N | N | N | —Ph |
| 132 | S | — | — | N | N | N | —Ph |
| 133 | O | — | — | N | N | N | —Ph |
| 134 | O | — | — | N | N | N | —Ph |
| 135 | S | — | — | N | N | N | —Ph |
| Compound No. | $Ar_2$ | $R_1$ | $R_2$ | Bonding position of $L_1$ | $R_3$ | Ra | Rb |
|---|---|---|---|---|---|---|---|
| 98 | —Ph | — | — | 3 | —Ph | — | — |
| 99 | —Ph | — | — | 3 | —Ph | — | — |
| 100 | —Ph | — | — | 3 | —Ph | — | — |
| 101 | —Ph | — | — | 3 | —Ph | — | — |
| 102 | —Ph | — | —Ph (6) | 3 | —Ph | — | — |
| 103 | —Ph | — | — | 3 | —Ph | — | — |
| 104 | —Ph | — | — | 3 | —Ph | — | — |
| 105 | —Ph | — | — | 3 | —Ph | — | — |
| 106 | —Ph | — | — | 3 | —Ph | — | — |
| 107 | —Ph | — | — | 3 | —Ph | — | — |
| 108 | —Ph | — | — | 3 | —Ph | — | — |
| 109 | —Ph | — | — | 3 | —Ph | — | — |
| 110 | 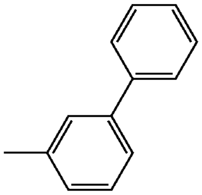 | — | —Ph (6) | 3 | —Ph | — | — |
| 111 | —Ph | — | — | 3 | —Ph | — | — |
| 112 | —Ph | — | — | 3 | —Ph | — | — |
| 113 | — | — | — | 3 | —Ph | — | — |
| 114 | —Ph | — | — | 3 | —Ph | —Ph (2) | — |
| 115 | —Ph | — | — | 3 | —Ph | — | —Ph (5) |
| 116 | 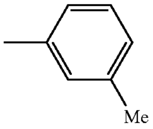 | — | — | 3 | —Ph | — | — |
| 117 | —Ph | — | — | 3 | —Ph | — | — |
| 118 | —Ph | — | — | 2 | —Ph | — | — |
| 119 | —tBu | — | — | 3 | —Ph | — | — |
| 120 | 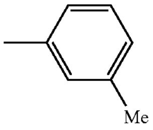 | — | — | 3 | —Ph | — | — |
| 121 | —Ph | — | — | 3 | —Ph | — | — |
| 122 | —Ph | — | — | 3 | —Ph | — | — |
| 123 | 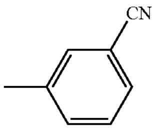 | — | — | 3 | —Ph | — | — |
| 124 | —Ph | — | — | 3 | —Ph | — | — |
| 125 | —Ph | — | —F (6) | 3 | —Ph | — | — |

-continued
| Formula (B4) | | | | | | | |
|---|---|---|---|---|---|---|---|
| 126 | 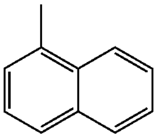 | — | — | 3 | —Ph | — | — |
| 127 | —iPr | — | — | 3 | —Ph | — | — |
| 128 | —Ph | — | — | 3 | —Ph | — | — |
| 129 | —Ph | — | — | 3 | —Ph | — | —Ph (5) |
| 130 | —Ph | — | — | 1 | —Ph | — | — |
| 131 | —Ph | — | — | 3 | 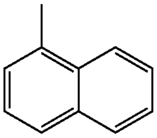 | — | — |
| 132 | —Ph | — | — | 3 | 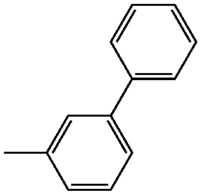 | — | — |
| 133 | —Ph | — | — | 3 | 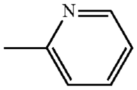 | — | — |
| 134 | —Ph | — | — | 3 | 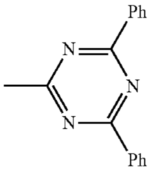 [SMILES: Cc1nc(-c2ccccc2)nc(-c2ccccc2)n1] | — | — |
| 135 | —Ph | — | — | 1 | —Ph | — | — |

Formula (C1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 136 | O | — | 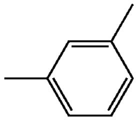 | N | N | N | —Ph | —Ph | — | — | 3 | —Ph | — | — |
| 137 | O | — | — | N | N | N | —Ph | —Ph | — | — | 3 | —Ph | — | —Ph (7) |
| 138 | S | — | — | N | N | CH | —Ph | —Ph | — | — | 3 | —Ph | — | — |
| 139 | S | 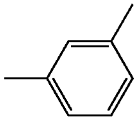 | — | N | C—Ph | N | —Ph | — | — | — | 3 | —Ph | — | — |
| 140 | O | — | — | N | N | N | —Ph | —Ph | — | — | 3 | —Ph | — | — |
| 141 | S | 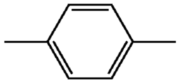 | — | N | N | N | 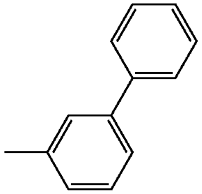 | 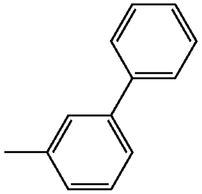 | — | —Ph (6) | 3 | —Ph | — | — |
| 142 | O | 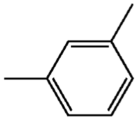 | 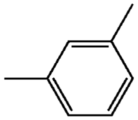 | N | CH | N | —Ph | —Ph | — | — | 3 | —Ph | — | — |
| 143 | S | — | 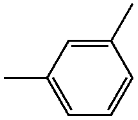 | CH | CH | N | —Ph | —Ph | — | — | 2 | —Ph | — | — |

Formula (C2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 144 | O | — | 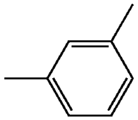 | N | N | N | —Ph | —Ph | — | — | 3 | —Ph | — | — |
| 145 | O | — | — | N | N | N | —Ph | —Ph | — | — | 3 | —Ph | — | — |
| 146 | S | — | — | N | N | CH | —Ph | —Ph | — | — | 3 | —Ph | — | — |
| 147 | S | 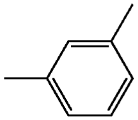 | — | N | C—Ph | N | —Ph | — | — | — | 3 | —Ph | — | — |
| 148 | O | — | — | N | N | N | —Ph | —Ph | — | — | 3 | —Me | — | — |
| 149 | S | 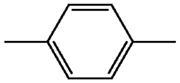 | — | N | N | N | 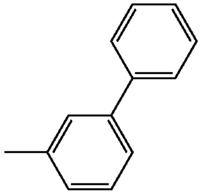 | 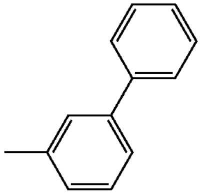 | — | —Ph (6) | 3 | —Ph | — | — |
| 150 | O | 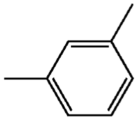 | 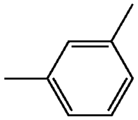 | N | CH | N | —Ph | —Ph | — | — | 3 | —Ph | — | — |
| 151 | S | — | 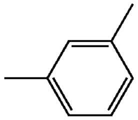 | CH | CH | N | —Ph | —Ph | — | — | 2 | —Ph | — | — |

Formula (C3)
| Compound No. | X | L1 | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 152 | O | — | 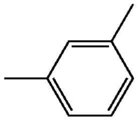 | N | N | N | —Ph | —Ph | — | — | 3 | —Ph | — | — |
| 153 | O | — | — | N | N | N | —Ph | —Ph | — | — | 3 | —Ph | — | — |
| 154 | S | — | — | N | N | CH | —Ph | —Ph | — | — | 3 | —Ph | — | — |
| 155 | S | 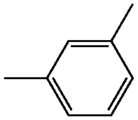 | — | N | C—Ph | N | —Ph | — | — | — | 3 | —Ph | — | — |
| 156 | O | — | — | N | N | N | —Ph | —Ph | — | — | 3 | 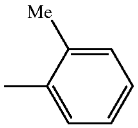 | — | — |
| 157 | S | 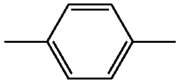 | — | N | N | N | 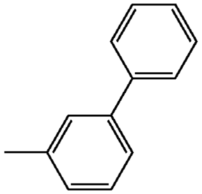 | 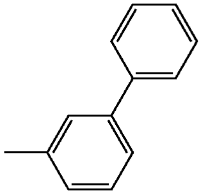 | — | —Ph (6) | 3 | —Ph | — | — |
| 158 | O | 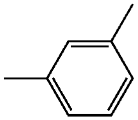 | 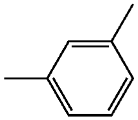 | N | CH | N | —Ph | —Ph | — | — | 3 | —Ph | — | — |
| 159 | S | — | 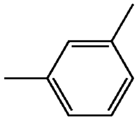 | CH | CH | N | —Ph | —Ph | — | — | 2 | —Ph | — | — |

Formula (C4)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 160 | O | — | 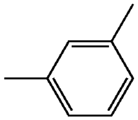 | N | N | N | —Ph | —Ph | — | — | 3 | —Ph | — | — |
| 161 | O | — | — | N | N | N | —Ph | —Ph | — | — | 3 | 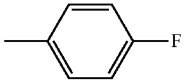 | — | — |
| 162 | S | — | — | N | N | CH | —Ph | —Ph | — | —Me (6) | 3 | —Ph | — | — |
| 163 | S | 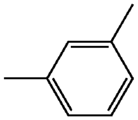 | — | N | C—Ph | N | —Ph | — | — | — | 3 | —Ph | — | — |
| 164 | O | — | — | N | N | N | —Ph | —Ph | — | — | 3 | —Ph | — | — |
| 165 | S | 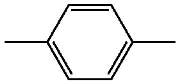 | — | N | N | N | 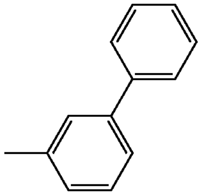 | 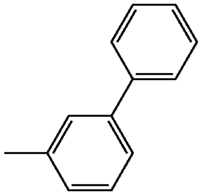 | — | —Ph (6) | 3 | —Ph | — | — |
| 166 | O | 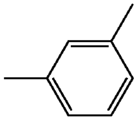 | 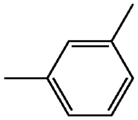 | N | CH | N | —Ph | —Ph | — | — | 3 | —Ph | — | — |
| 167 | S | — | 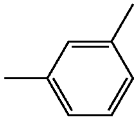 | CH | CH | N | —Ph | —Ph | — | — | 2 | —Ph | — | — |

Formula (D1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 168 | 0 | — | 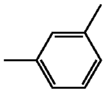 | N | N | N | —Ph | —Ph | — | — | 3 | —Ph | — | — |
| 169 | 0 | — | — | N | N | N | —Ph | —Ph | — | —Ph (6) | 3 | —Ph | — | — |
| 170 | S | — | — | N | N | CH | —Ph | —Ph | — | — | 3 | —Ph | — | — |
| 171 | S | 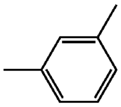 | — | N | C—Ph | N | —Ph | — | — | — | 3 | —Ph | — | — |
| 172 | 0 | — | — | N | N | N | —Ph | —Ph | — | — | 3 | —tBu | — | — |
| 173 | S | 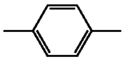 | — | N | N | N | 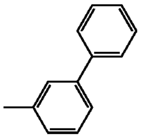 | 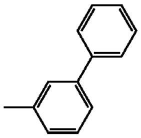 | — | —Ph (6) | 3 | —Ph | — | — |
| 174 | 0 | 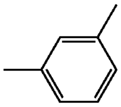 | 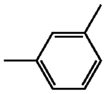 | N | CH | N | —Ph | —Ph | — | — | 3 | —Ph | — | — |
| 175 | S | — | 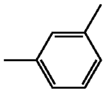 | CH | CH | N | —Ph | —Ph | — | — | 2 | —Ph | — | — |

Formula (D2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 176 | 0 | — | 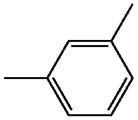 | N | N | N | —Ph | —Ph | — | — | 3 | —Ph | — | — |
| 177 | 0 | 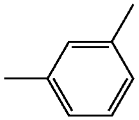 | — | N | N | N | —Ph | —Ph | — | — | 3 | —Ph | — | — |
| 178 | 0 | 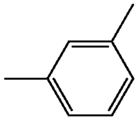 | 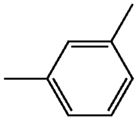 | N | N | N | —Ph | —Ph | — | — | 3 | —Ph | — | — |
| 179 | 0 | 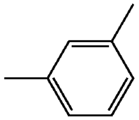 | — | N | N | N | —Ph | —Ph | — | — | 3 | —Ph | — | — |
| 180 | S | 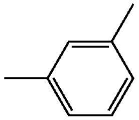 | 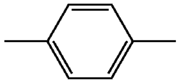 | N | N | N | —Ph | —Ph | — | —Ph (6) | 3 | —Ph | — | — |
| 181 | S | — | — | N | N | N | —Ph | —Ph | — | — | 3 | —Ph | — | — |
| 182 | 0 | 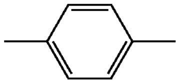 | 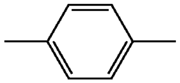 | N | N | N | —Ph | —Ph | — | — | 3 | —Ph | — | — |
| 183 | 0 | 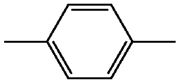 | — | N | N | N | —Ph | —Ph | — | — | 3 | —Ph | — | — |

Formula (D2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 184 | 0 | — | 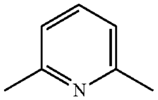 | N | CH | N | —Ph | —Ph | — | — | 3 | —Ph | — | — |
| 185 | 0 | 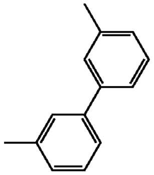 | — | N | N | CH | —Ph | —Ph | — | — | 3 | —Ph | — | — |
| 186 | 0 | 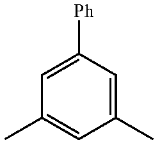 | — | N | N | N | —Ph | —Ph | — | — | 3 | —Ph | — | — |
| 187 | 0 | — | — | N | N | N | —Ph | —Ph | — | — | 3 | —Ph | — | — |
| 188 | 0 | 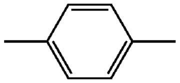 | — | N | N | N | 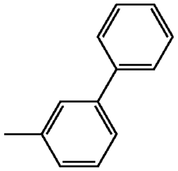 | 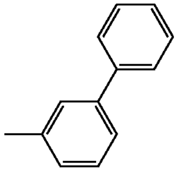 | — | —Ph (6) | 3 | —Ph | — | — |
| 189 | 0 | 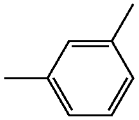 | 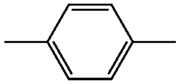 | N | N | N | —Ph | —Ph | — | — | 3 | —Ph | — | — |
| 190 | 0 | — | — | CH | N | N | — | —Ph | — | — | 3 | —Ph | — | — |
| 191 | 0 | — | — | N | C—Ph | N | — | — | — | — | 3 | —Ph | — | — |
| 192 | 0 | — | — | N | N | N | —Ph | —Ph | — | — | 3 | —Ph | —Ph (4) | — |

Formula (D2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 193 | 0 | 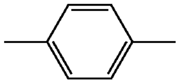 | — | N | N | N | —Ph | —Ph | — | — | 3 | —Ph | — | —Ph (7) |
| 194 | 0 | — | — | N | N | N | —Ph | 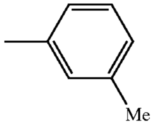 | — | — | 3 | —Ph | — | — |
| 195 | 0 | — | — | N | CH | N | —Ph | —Ph | — | — | 3 | —Ph | — | — |
| 196 | S | — | 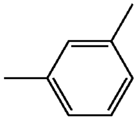 | N | N | N | —Ph | —Ph | — | — | 2 | —Ph | — | — |
| 197 | 0 | — | — | N | N | N | —tBu | —tBu | — | — | 3 | —Ph | — | — |
| 198 | S | — | — | N | N | N | —Ph | 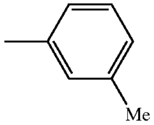 | — | — | 3 | —Ph | — | — |
| 199 | S | —$CH_2$— | — | N | N | N | 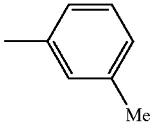 | —Ph | — | — | 3 | —Ph | — | — |
| 200 | 0 | 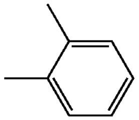 | — | N | N | N | —Ph | —Ph | — | — | 3 | —Ph | — | — |
| 201 | 0 | — | — | N | N | N | 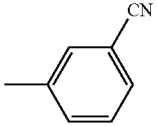 | 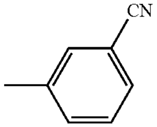 | — | — | 3 | —Ph | — | — |

Formula (D2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 202 | S | 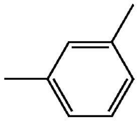 | $—(CH_2)_2—$ | N | N | N | —Ph | —Ph | — | — | 3 | —Ph | — | — |
| 203 | 0 | — | — | N | N | N | —Ph | —Ph | — | —F(6) | 3 | —Ph | — | — |
| 204 | 0 | — | — | N | N | N | 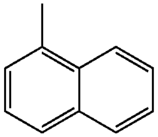 | 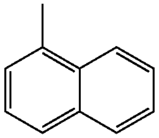 | — | — | 3 | —Ph | — | — |
| 205 | S | — | — | N | N | N | —iPr | —iPr | — | — | 3 | —Ph | — | — |
| 206 | 0 | 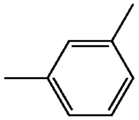 | — | N | N | N | —Ph | —Ph | — | — | 3 | —Ph | — | — |
| 207 | 0 | — | — | N | N | N | —Ph | —Ph | — | — | 3 | —Ph | — | —Ph (7) |

Formula (D2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 208 | 0 | — | — | N | N | N | —Ph | —Ph | — | — | 3 | 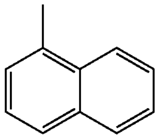 | — | — |
| 209 | S | — | — | N | N | N | —Ph | —Ph | — | — | 3 | 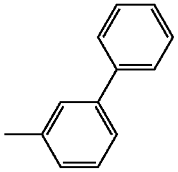 | — | — |
| 210 | 0 | — | — | N | N | N | —Ph | —Ph | — | — | 3 | 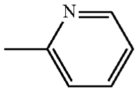 | — | — |
| 211 | 0 | — | — | N | N | N | —Ph | —Ph | — | — | 3 | 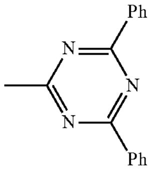 | — | — |
| 212 | S | — | — | N | N | N | —Ph | —Ph | — | — | 1 | —Ph | — | — |

Formula (D3)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 213 | 0 | — | 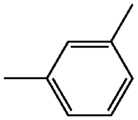 | N | N | N | —Ph | —Ph | — | — | 3 | —Ph | — | — |
| 214 | 0 | — | — | N | N | N | —Ph | —Ph | — | —Me (6) | 3 | —Ph | — | — |
| 216 | S | — | — | N | N | CH | —Ph | —Ph | — | — | 3 | —Ph | — | — |
| 216 | S | 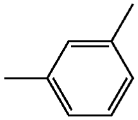 | — | N | C—Ph | N | —Ph | — | — | — | 3 | —Ph | — | — |
| 217 | 0 | — | — | N | N | N | —Ph | —Ph | — | — | 3 | 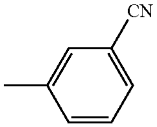 | — | — |
| 218 | S | 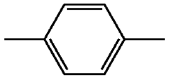 | — | N | N | N | 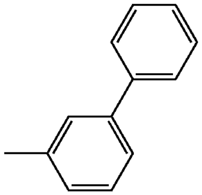 | 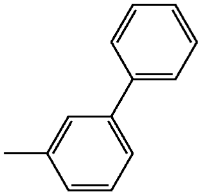 | — | —Ph (6) | 3 | —Ph | — | — |
| 219 | 0 | 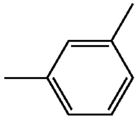 | 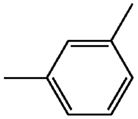 | N | CH | N | —Ph | —Ph | — | — | 3 | —Ph | — | — |
| 220 | S | — | 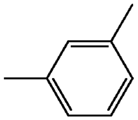 | CH | CH | N | —Ph | —Ph | — | — | 2 | —Ph | — | — |

Formula (D4)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 221 | 0 | — | 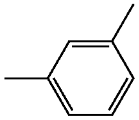 | N | N | N | —Ph | —Ph | — | — | 3 | —Ph | — | — |
| 222 | 0 | 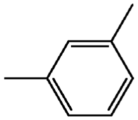 | — | N | N | N | —Ph | —Ph | — | — | 3 | —Ph | — | — |
| 223 | 0 | 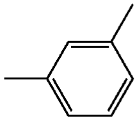 | 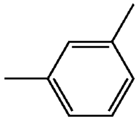 | N | N | N | —Ph | —Ph | — | — | 3 | —Ph | — | — |
| 224 | 0 | 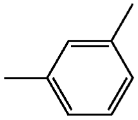 | — | N | N | N | —Ph | — | — | — | 3 | —Ph | — | — |
| 225 | S | 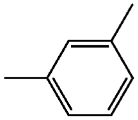 | 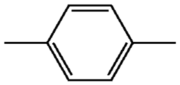 | N | N | N | —Ph | —Ph | — | —Ph (6) | 3 | —Ph | — | — |
| 226 | S | — | — | N | N | N | —Ph | —Ph | — | — | 3 | —Ph | — | — |
| 227 | 0 | 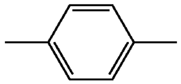 | 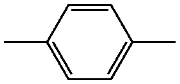 | N | N | N | —Ph | —Ph | — | — | 3 | —Ph | — | — |
| 228 | 0 | 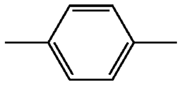 | — | N | N | N | —Ph | —Ph | — | — | 3 | —Ph | — | — |

Formula (D4)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 229 | 0 | — | 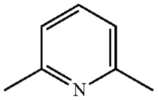 | N | N | N | —Ph | —Ph | — | — | 3 | —Ph | — | — |
| 230 | 0 | 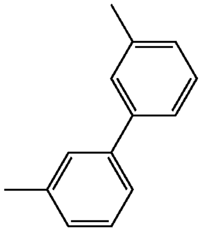 | — | N | N | CH | —Ph | —Ph | — | — | 3 | —Ph | — | — |
| 231 | 0 | 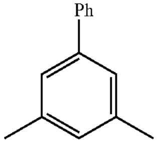 | — | N | N | N | —Ph | —Ph | — | — | 3 | —Ph | — | — |
| 232 | 0 | — | — | N | N | N | —Ph | —Ph | — | — | 3 | —Ph | — | — |
| 233 | 0 | 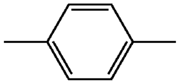 | — | N | N | N | 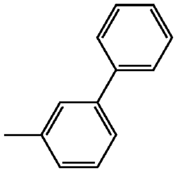 | 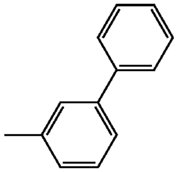 | — | —Ph (6) | 3 | —Ph | — | — |
| 234 | 0 | 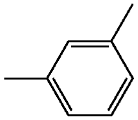 | 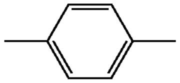 | N | N | N | —Ph | —Ph | — | — | 3 | —Ph | — | — |
| 235 | 0 | — | — | CH | N | N | — | —Ph | — | — | 3 | —Ph | — | — |
| 236 | 0 | — | — | N | C—Ph | N | — | — | — | — | 3 | —Ph | — | |
| 237 | 0 | — | — | N | N | N | —Ph | —Ph | — | — | 3 | —Ph | —Ph (2) | — |

Formula (D4)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 238 | 0 | 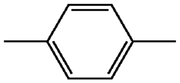 | — | N | N | N | —Ph | —Ph | — | — | 3 | —Ph | — | —Ph (7) |
| 239 | 0 | — | — | N | N | N | —Ph | 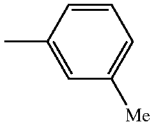 | — | — | 3 | —Ph | — | — |
| 240 | 0 | — | — | N | CH | N | —Ph | —Ph | — | — | 3 | —Ph | — | — |
| 241 | S | — | 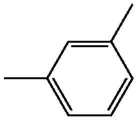 | N | N | N | —Ph | —Ph | — | — | 2 | —Ph | — | — |
| 242 | 0 | — | — | N | N | N | —tBu | —tBu | — | — | 3 | —Ph | — | — |
| 243 | S | — | — | N | N | N | —Ph | 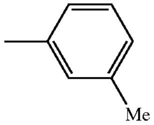 | — | — | 3 | —Ph | — | — |
| 244 | S | $—CH_2—$ | — | N | N | N | 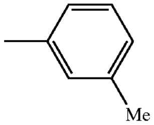 | —Ph | — | — | 3 | —Ph | — | — |
| 245 | 0 | 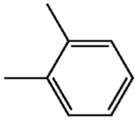 | — | N | N | N | —Ph | —Ph | — | — | 3 | —Ph | — | — |
| 246 | 0 | — | — | N | N | N | 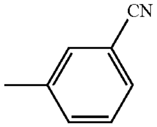 | 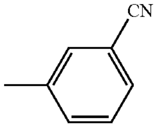 | — | — | 3 | —Ph | — | — |

Formula (D4)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 247 | S | 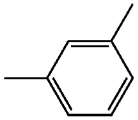 | $-(CH_2)_2-$ | N | N | N | —Ph | —Ph | — | — | 3 | —Ph | — | — |
| 248 | 0 | — | — | N | N | N | —Ph | —Ph | — | —F (6) | 3 | —Ph | — | — |
| 249 | 0 | — | — | N | N | N | 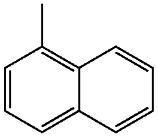 | 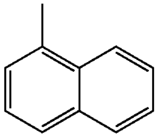 | — | — | 3 | —Ph | — | — |
| 250 | S | — | — | N | N | N | —iPr | —iPr | — | — | 3 | —Ph | — | — |
| 251 | 0 | 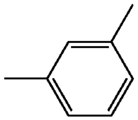 | — | N | N | N | —Ph | —Ph | — | — | 3 | —Ph | — | — |
| 252 | 0 | — | — | N | N | N | —Ph | —Ph | — | — | 3 | —Ph | — | —Ph (7) |

Formula (D4)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 253 | 0 | — | — | N | N | N | —Ph | —Ph | — | — | 3 | 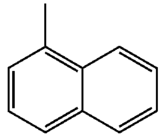 | — | — |
| 254 | S | — | — | N | N | N | —Ph | —Ph | — | — | 3 | 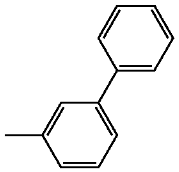 | — | — |
| 255 | 0 | — | — | N | N | N | —Ph | —Ph | — | — | 3 | 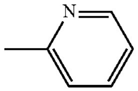 | — | — |
| 256 | 0 | — | — | N | N | N | —Ph | —Ph | — | — | 3 | 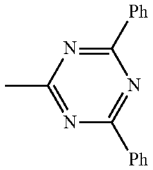 | — | — |
| 257 | S | — | — | N | N | N | —Ph | —Ph | — | — | 1 | —Ph | — | — |

Formula (E1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 258 | 0 | — | 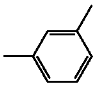 | N | N | N | —Ph | —Ph | — | — | 3 | —Ph | — | — |
| 259 | 0 | — | — | N | N | N | —Ph | —Ph | — | — | 3 | 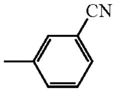 | — | — |
| 260 | S | — | — | N | N | CH | —Ph | —Ph | — | — | 3 | —Ph | — | — |
| 261 | S | 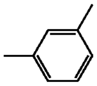 | — | N | C—Ph | N | —Ph | — | — | — | 3 | —Ph | — | — |
| 262 | 0 | — | — | N | N | N | —Ph | —Ph | — | — | 3 | —Ph | — | — |
| 263 | S | 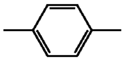 | — | N | N | N | 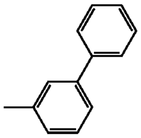 | 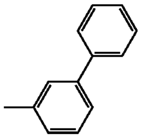 | — | —Ph (6) | 3 | —Ph | — | — |
| 264 | 0 | 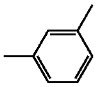 | 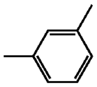 | N | CH | N | —Ph | —Ph | — | — | 3 | —Ph | — | — |
| 265 | S | — | 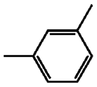 | CH | CH | N | —Ph | —Ph | — | — | 2 | —Ph | — | — |

Formula (E2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 266 | 0 | — | 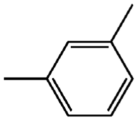 | N | N | N | —Ph | —Ph | — | — | 3 | —Ph | — | — |
| 267 | 0 | — | — | N | N | N | —Ph | —Ph | — | — | 3 | —Ph | — | — |
| 268 | S | — | — | N | N | CH | —Ph | —Ph | — | — | 3 | —Ph | — | — |
| 269 | S | 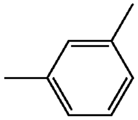 | — | N | C—Ph | N | —Ph | — | — | — | 3 | —Ph | — | — |
| 270 | 0 | — | — | N | N | N | —Et | —Et | — | — | 3 | —Ph | — | — |
| 271 | S | 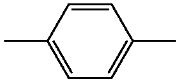 | — | N | N | N | 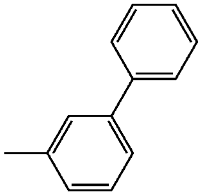 | 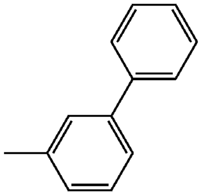 | — | —Ph (6) | 3 | —Ph | — | — |
| 272 | 0 | 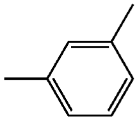 | 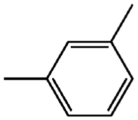 | N | CH | N | —Ph | —Ph | — | — | 3 | 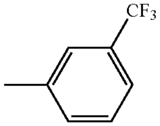 | — | — |
| 273 | S | — | 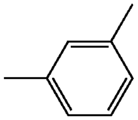 | CH | CH | N | —Ph | —Ph | — | — | 2 | —Ph | — | — |

Formula (E3)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 274 | 0 | — | 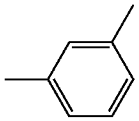 | N | N | N | —Ph | —Ph | — | — | 3 | —Ph | — | — |
| 275 | 0 | — | 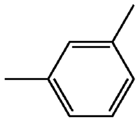 | N | N | N | —Ph | —Ph | — | — | 3 | —Ph | — | — |
| 276 | 0 | — | — | N | N | N | —Ph | —Ph | — | — | 3 | —Ph | — | — |
| 277 | S | 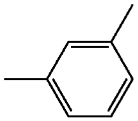 | — | N | N | CH | —Ph | —Ph | — | — | 3 | —Ph | — | — |

Formula (E3)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 278 | S | 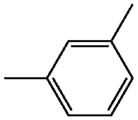 | — | N | C—Ph | N | —Ph | — | — | — | 3 | —Ph | — | — |
| 279 | 0 | 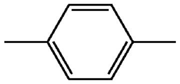 | — | N | N | N | 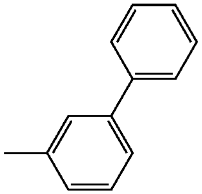 | 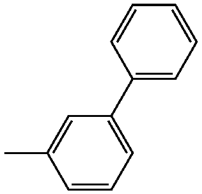 | — | — | 3 | —Ph | — | — |
| 280 | S | 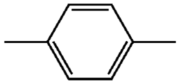 | 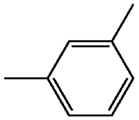 | N | N | N | 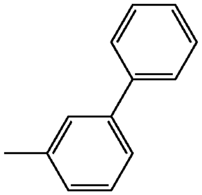 | 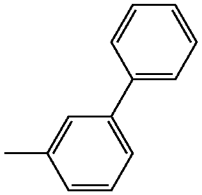 | — | —Ph (6) | 3 | —Ph | — | — |
| 281 | 0 | 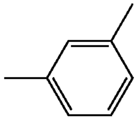 | 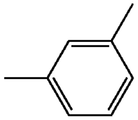 | N | CH | N | —Ph | —Ph | — | — | 3 | 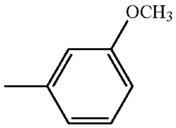 | — | — |
| 282 | S | — | 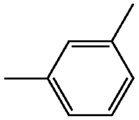 | CH | CH | N | —Ph | —Ph | — | — | 2 | —Ph | — | — |

Formula (F1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 283 | 0 | — | 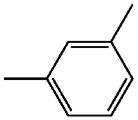 | N | N | N | —Ph | —Ph | — | — | 3 | —Ph | — | — |
| 284 | 0 | — | — | N | N | N | —Ph | —Ph | — | — | 3 | —Ph | — | — |
| 285 | S | 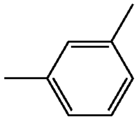 | — | N | N | CH | —Ph | —Ph | — | — | 3 | —Ph | — | — |
| 286 | S | 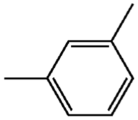 | — | N | C—Ph | N | —Ph | — | — | — | 3 | —Ph | — | — |
| 287 | 0 | 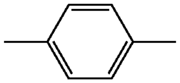 | — | N | N | N | 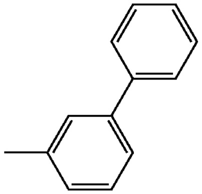 | 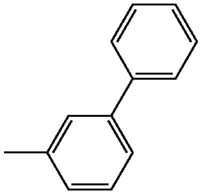 | — | — | 3 | —Ph | — | — |

Formula (F1)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 288 | S | 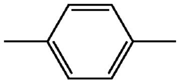 | 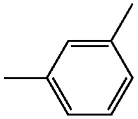 | N | N | N | 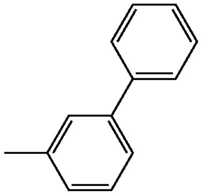 | 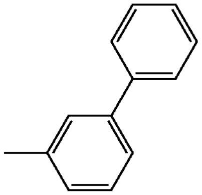 | — | —Ph (6) | 3 | —Ph | — | — |
| 289 | 0 | 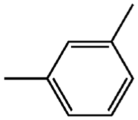 | 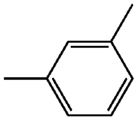 | N | CH | N | —Ph | —Ph | — | — | 3 | 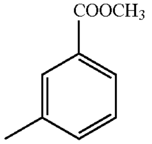 | — | — |
| 290 | S | — | 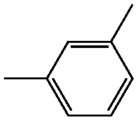 | CH | CH | N | —Ph | —Ph | — | — | 2 | —Ph | — | — |

Formula (F2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 291 | 0 | — | 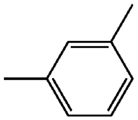 | N | N | N | —Ph | —Ph | — | — | 3 | —Ph | — | — |
| 292 | 0 | — | — | N | N | N | —Ph | —Ph | — | — | 3 | —Ph | — | — |
| 293 | S | 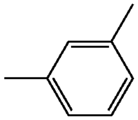 | — | N | N | CH | —Ph | —Ph | — | — | 3 | —Ph | — | — |
| 294 | S | 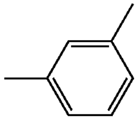 | — | N | C—Ph | N | —Ph | — | — | — | 3 | —Ph | — | — |
| 295 | 0 | 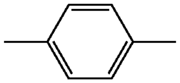 | — | N | N | N | 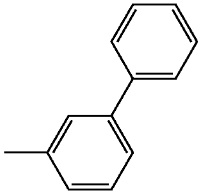 | 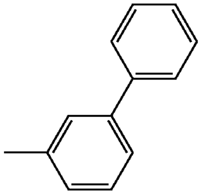 | — | — | 3 | —Ph | — | — |

Formula (F2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 296 | S | 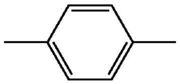 | 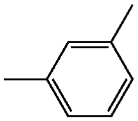 | N | N | N | 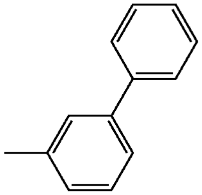 | 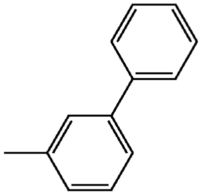 | — | —Ph (6) | 3 | —Ph | — | — |
| 297 | 0 | 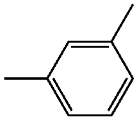 | 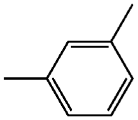 | N | CH | N | —Ph | —Ph | — | — | 3 | 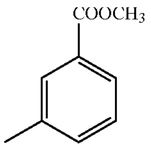 | — | — |
| 296 | S | — | 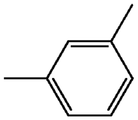 | CH | CH | N | —Ph | —Ph | — | — | 2 | —Ph | — | — |

Formula (F3)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 299 | 0 | — | 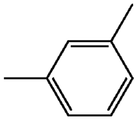 | N | N | N | —Ph | —Ph | — | — | 3 | —Ph | — | — |
| 300 | 0 | 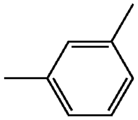 | — | N | N | N | —Ph | —Ph | — | — | 3 | —Ph | — | — |
| 301 | 0 | 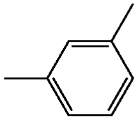 | 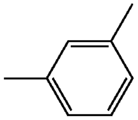 | N | N | N | —Ph | —Ph | — | — | 3 | —Ph | — | — |
| 302 | 0 | 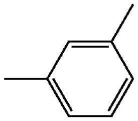 | — | N | N | C—Ph | —Ph | — | — | — | 3 | —Ph | — | — |
| 303 | S | 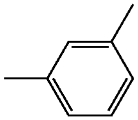 | 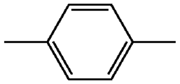 | N | N | N | —Ph | —Ph | — | —Ph (6) | 3 | —Ph | — | — |
| 304 | S | — | — | N | N | N | —Ph | —Ph | — | — | 3 | —Ph | — | — |
| 305 | 0 | 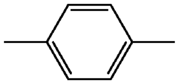 | 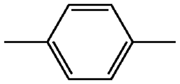 | N | N | N | —Ph | —Ph | — | — | 3 | —Ph | — | — |
| 306 | 0 | 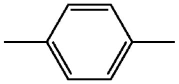 | — | N | N | N | —Ph | —Ph | — | — | 3 | —Ph | — | — |

Formula (F3)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 307 | 0 | — | 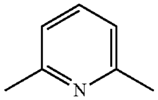 | N | N | N | —Ph | —Ph | — | — | 3 | —Ph | — | — |
| 308 | 0 | 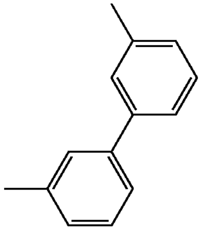 | — | N | N | CH | —Ph | —Ph | — | — | 3 | —Ph | — | — |
| 309 | 0 | 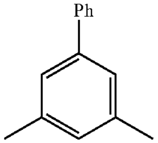 | — | N | N | N | —Ph | —Ph | — | — | 3 | —Ph | — | — |
| 310 | 0 | — | — | N | N | N | —Ph | —Ph | — | — | 3 | —Ph | — | — |
| 311 | 0 | 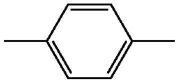 | — | N | N | N | 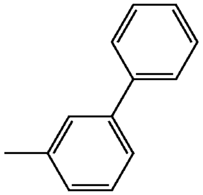 | 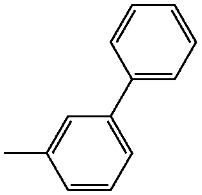 | — | —Ph (6) | 3 | —Ph | — | — |
| 312 | 0 | 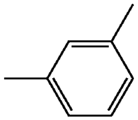 | 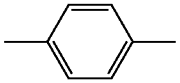 | N | N | N | —Ph | —Ph | — | — | 3 | —Ph | — | — |
| 313 | 0 | — | — | CH | N | N | — | —Ph | — | — | 3 | —Ph | — | — |
| 314 | 0 | — | — | N | C—Ph | N | — | — | — | — | 3 | —Ph | — | — |

Formula (F3)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 315 | 0 | — | — | N | N | N | —Ph | —Ph | — | — | 3 | —Ph | — | —Ph (7) |
| 316 | 0 | 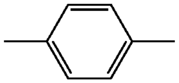 | — | N | N | N | —Ph | —Ph | — | — | 3 | —Ph | — | —Ph (5) |
| 317 | 0 | — | — | N | N | N | —Ph | 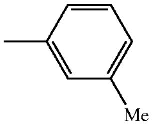 | — | — | 3 | —Ph | — | — |
| 318 | 0 | — | — | N | CH | N | —Ph | —Ph | — | — | 3 | —Ph | — | — |
| 319 | 0 | — | 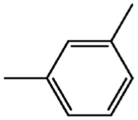 | N | N | N | —Ph | —Ph | — | — | 2 | —Ph | — | — |
| 320 | 0 | — | — | N | N | N | —tBu | —tBu | — | — | 3 | —Ph | — | — |
| 321 | S | — | — | N | N | N | —Ph | 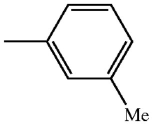 | — | — | 3 | —Ph | — | — |
| 322 | S | —$CH_2$— | — | N | N | N | 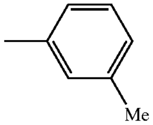 | —Ph | — | — | 3 | —Ph | — | — |
| 323 | 0 | 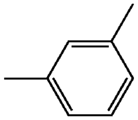 | — | N | N | N | —Ph | —Ph | — | — | 3 | —Ph | — | — |

Formula (F3)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 324 | 0 | — | — | N | N | N | 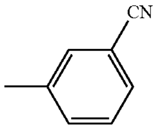 | 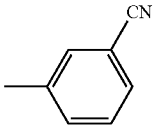 | — | — | 3 | —Ph | — | — |
| 325 | S | 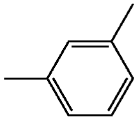 | $-(CH_2)_2-$ | N | N | N | —Ph | —Ph | — | — | 3 | —Ph | — | — |
| 326 | 0 | — | — | N | N | N | —Ph | —Ph | — | —F (6) | 3 | —Ph | — | — |
| 327 | 0 | — | — | N | N | N | 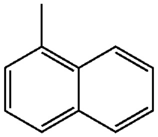 | 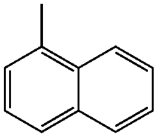 | — | — | 3 | —Ph | — | — |
| 328 | S | — | — | N | N | N | —iPr | —iPr | — | — | 3 | —Ph | — | — |
| 329 | 0 | 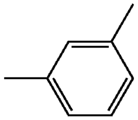 | — | N | N | N | —Ph | —Ph | — | — | 3 | —Ph | — | — |
| 330 | 0 | — | — | N | N | N | —Ph | —Ph | — | — | 3 | —Ph | — | —Ph (5) |
| 331 | 0 | — | — | N | N | N | —Ph | —Ph | — | — | 3 | 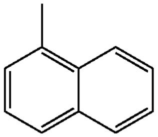 | — | — |

Formula (F3)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 332 | S | — | — | N | N | N | —Ph | —Ph | — | — | 3 | 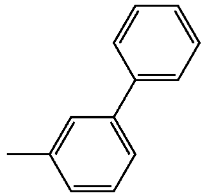 | — | — |
| 333 | 0 | — | — | N | N | N | —Ph | —Ph | — | — | 3 | 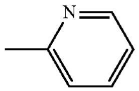 | — | — |
| 334 | 0 | — | — | N | N | N | —Ph | —Ph | — | — | 3 | 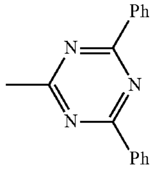 | — | — |
| 335 | S | — | — | N | N | N | —Ph | —Ph | — | — | 1 | —Ph | — | — |

Formula (G1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 336 | 0 | — | 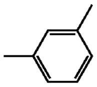 | N | N | N | —Ph | —Ph | — | — | 3 | —Ph | — | — |
| 337 | 0 | — | — | N | N | N | —Ph | —Ph | — | — | 3 | —Ph | — | — |
| 338 | S | 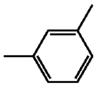 | — | N | N | CH | —Ph | —Ph | — | — | 3 | —Ph | — | — |
| 339 | S | 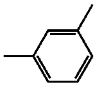 | — | N | C—Ph | N | —Ph | — | — | — | 3 | —Ph | — | — |
| 340 | 0 | 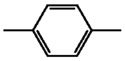 | — | N | N | N | 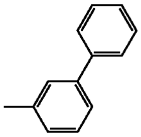 | 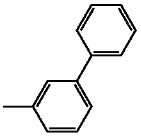 | — | — | 3 | —Ph | — | — |
| 341 | S | 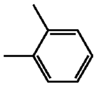 | 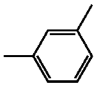 | N | N | N | 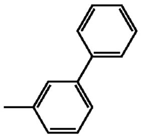 | 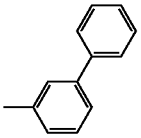 | — | —Ph (6) | 3 | —Ph | — | — |
| 342 | 0 | 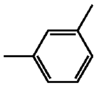 | 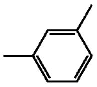 | N | CH | N | —Ph | —Ph | — | — | 3 | 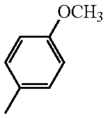 | — | — |
| 343 | S | — | 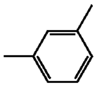 | CH | CH | N | —Ph | —Ph | — | — | 2 | —Ph | — | — |

Formula (G2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 344 | 0 | — | 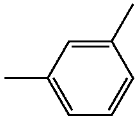 | N | N | N | —Ph | —Ph | — | — | 3 | —Ph | — | — |
| 345 | 0 | — | — | N | N | N | —Ph | —Ph | — | — | 3 | —Ph | — | — |
| 346 | S | 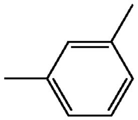 | — | N | N | CH | —Ph | —Ph | — | — | 3 | —Ph | — | — |
| 347 | S | 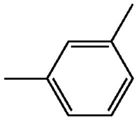 | — | N | C—Ph | N | —Ph | — | — | — | 3 | —Ph | — | — |
| 348 | 0 | 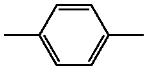 | — | N | N | N | 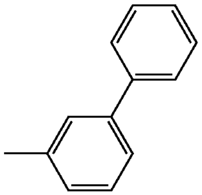 | 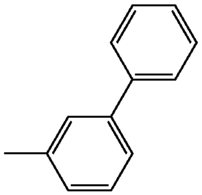 | — | — | 3 | —Ph | — | — |
| 349 | S | 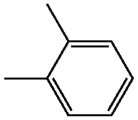 | 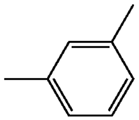 | N | N | N | 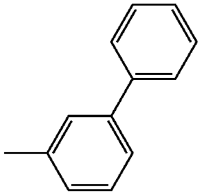 | 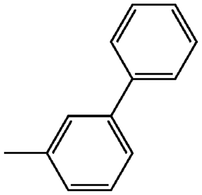 | — | —Ph (6) | 3 | —Ph | — | — |

Formula (G2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 350 | 0 | 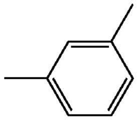 | 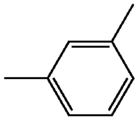 | N | CH | N | —Ph | —Ph | — | — | 3 | 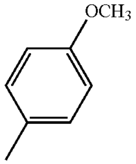 | — | — |
| 351 | S | — | 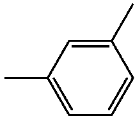 | CH | CH | N | —Ph | —Ph | — | — | 2 | —Ph | — | — |

Formula (G3)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 352 | 0 | — | 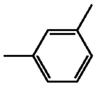 | N | N | N | —Ph | —Ph | — | — | 3 | —Ph | — | — |
| 353 | 0 | — | — | N | N | N | —Ph | —Ph | — | — | 3 | —Ph | — | — |
| 354 | S | 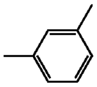 | — | N | N | CH | —Ph | —Ph | — | — | 3 | —Ph | — | — |
| 355 | S | 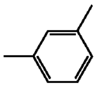 | — | N | C—Ph | N | —Ph | — | — | — | 3 | —Ph | — | — |
| 356 | 0 | 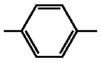 | — | N | N | N | 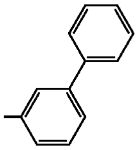 | 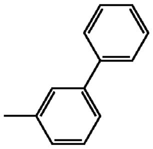 | — | — | 3 | —Ph | — | — |
| 357 | S | 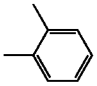 | 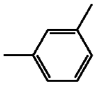 | N | N | N | 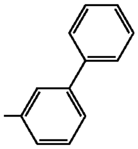 | 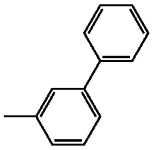 | — | —Ph (6) | 3 | —Ph | — | — |
| 358 | 0 | 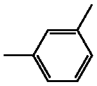 | 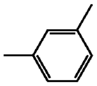 | N | CH | N | —Ph | —Ph | — | — | 3 | 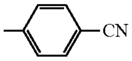 | — | — |
| 359 | S | — | 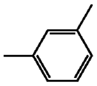 | CH | CH | N | —Ph | —Ph | — | — | 2 | —Ph | — | — |
Formula (H1)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 360 | 0 | — | 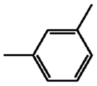 | N | N | N | —Ph | —Ph | — | — | 3 | —Ph | — | — |
| 361 | 0 | — | — | N | N | N | —Ph | —Ph | — | — | 3 | —Ph | — | — |
| 362 | S | — | — | N | N | CH | —Ph | —Ph | — | — | | —Ph | — | — |
| 363 | S | 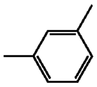 | — | N | C—Ph | N | —Ph | — | | — | 3 | —Ph | — | — |
| 364 | 0 | 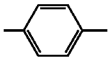 | — | N | N | N | 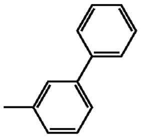 | 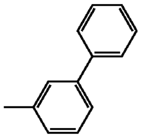 | — | — | 3 | —Ph | — | — |

Formula (H1)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 365 | S | 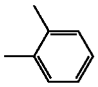 | 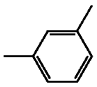 | N | N | N | 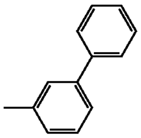 | 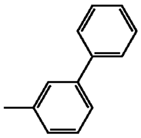 | — | —Ph (6) | 3 | —Ph | — | — |
| 366 | 0 | 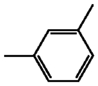 | 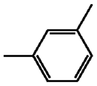 | N | CH | N | —Ph | —Ph | — | — | 3 | 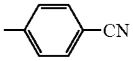 | — | — |
| 367 | S | — | 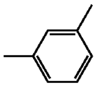 | CH | CH | N | —Ph | —Ph | — | — | 2 | —Ph | — | — |

Formula (H2)
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 368 | 0 | — | 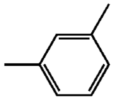 | N | N | N | —Ph | —Ph | — | — | 3 | —Ph | — | — |
| 369 | 0 | 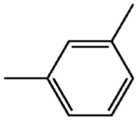 | — | N | N | N | —Ph | —Ph | — | — | 3 | —Ph | — | — |
| 370 | 0 | 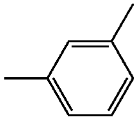 | 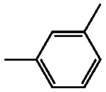 | N | N | N | —Ph | —Ph | — | — | 3 | —Ph | — | — |
| 371 | 0 | 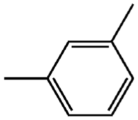 | — | N | N | C—Ph | —Ph | — | — | — | 3 | —Ph | — | — |
| 372 | S | 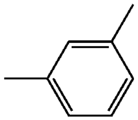 | 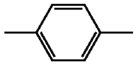 | N | N | N | —Ph | —Ph | — | —Ph (6) | 3 | —Ph | — | — |
| 373 | S | — | — | N | N | N | —Ph | —Ph | — | — | 3 | —Ph | — | — |
| 374 | 0 | 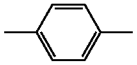 | 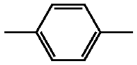 | N | N | N | —Ph | —Ph | — | — | 3 | —Ph | — | — |
| 375 | 0 | 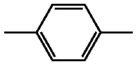 | — | N | N | N | —Ph | —Ph | — | — | 3 | —Ph | — | — |
| 376 | 0 | — | 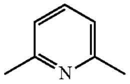 | N | CH | N | —Ph | —Ph | — | — | 3 | —Ph | — | — |

Formula (H2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 377 | 0 | 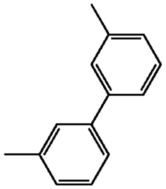 | — | N | N | CH | —Ph | —Ph | — | — | 3 | —Ph | — | — |
| 378 | 0 | 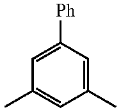 | — | N | N | N | —Ph | —Ph | — | — | 3 | —Ph | — | — |
| 379 | 0 | — | — | N | N | N | —Ph | —Ph | — | — | 3 | —Ph | — | — |
| 380 | 0 | 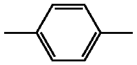 | — | N | N | N | 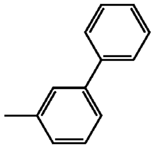 | 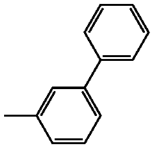 | — | —Ph (6) | 3 | —Ph | — | — |
| 381 | 0 | 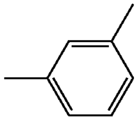 | 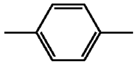 | N | N | N | —Ph | —Ph | — | — | 3 | —Ph | — | — |
| 382 | 0 | — | — | CH | N | N | — | —Ph | — | — | 3 | —Ph | — | — |
| 383 | 0 | — | — | N | C—Ph | N | — | — | — | — | 3 | —Ph | — | — |
| 384 | 0 | — | — | N | N | N | —Ph | —Ph | — | — | 3 | —Ph | — | —Ph (7) |
| 385 | 0 | 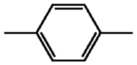 | — | N | N | N | —Ph | —Ph | — | — | 3 | —Ph | — | —Ph (5) |
| 386 | 0 | — | — | N | N | N | —Ph | 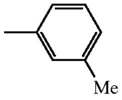 | — | — | 3 | —Ph | — | — |
| 387 | 0 | — | — | N | CH | N | —Ph | —Ph | — | — | 3 | —Ph | — | — |

Formula (H2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 388 | S | — | 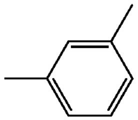 | N | N | N | —Ph | —Ph | — | — | 2 | —Ph | — | — |
| 389 | 0 | — | — | N | N | N | —tBu | —tBu | — | — | 3 | —Ph | — | — |
| 390 | S | — | — | N | N | N | —Ph | 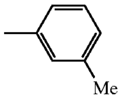 | — | — | 3 | —Ph | — | — |
| 391 | S | $—CH_2—$ | — | N | N | N | 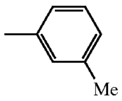 | —Ph | — | — | 3 | —Ph | — | — |
| 392 | 0 | 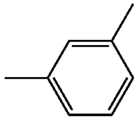 | — | N | N | N | —Ph | —Ph | — | — | 3 | —Ph | — | — |
| 393 | 0 | — | — | N | N | N | 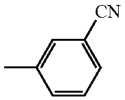 | 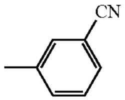 | — | — | 3 | —Ph | — | — |
| 394 | S | 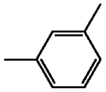 | $—(CH_2)_2—$ | N | N | N | —Ph | —Ph | — | — | 3 | —Ph | — | — |
| 395 | 0 | — | — | N | N | N | —Ph | —Ph | — | —F (6) | 3 | —Ph | — | — |
| 396 | 0 | — | — | N | N | N | 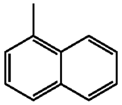 | 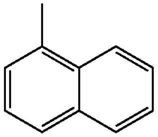 | — | — | 3 | —Ph | — | — |
| 397 | S | — | — | N | N | N | —iPr | —iPr | — | — | 3 | —Ph | — | — |

Formula (H2)-continued
| Compound No. | X | $L_1$ | $L_2$ | $Y_1$ | $Y_2$ | $Y_3$ | $Ar_1$ | $Ar_2$ | $R_1$ | $R_2$ | Bonding position of $L_1$ | $R_3$ | Ra | Rb |
|---|---|---|---|---|---|---|---|---|---|---|---|---|---|---|
| 398 | 0 | 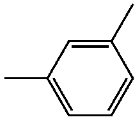 | — | N | N | N | —Ph | —Ph | — | — | 3 | —Ph | — | — |
| 399 | 0 | — | — | N | N | N | —Ph | —Ph | — | — | 3 | —Ph | — | —Ph (5) |
| 400 | 0 | — | — | N | N | N | —Ph | —Ph | — | — | 3 | 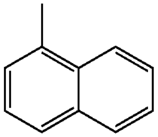 | — | — |
| 401 | S | — | — | N | N | N | —Ph | —Ph | — | — | 3 | 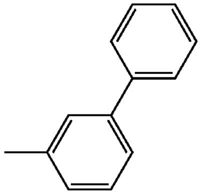 | — | — |
| 402 | 0 | — | — | N | N | N | —Ph | —Ph | — | — | 3 | 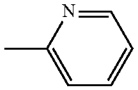 | — | — |
| 403 | 0 | — | — | N | N | N | —Ph | —Ph | — | — | 3 | 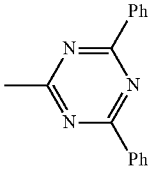 | — | — |
| 404 | S | — | — | N | N | N | —Ph | —Ph | — | — | 1 | —Ph | — | — |

Formula (H3)
| Compound No. | X | $L_1$ | $L_2$ | $Y_1$ | $Y_2$ | $Y_3$ | $Ar_1$ |
|---|---|---|---|---|---|---|---|
| 405 | O | — | 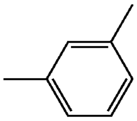 | N | N | N | —Ph |
| 406 | O | — | — | N | N | N | —Ph |
| 407 | S | 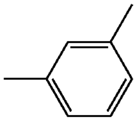 | — | N | N | CN | —Ph |
| 408 | S | 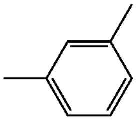 | — | N | C—Ph | N | —Ph |
| 409 | O | 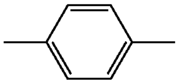 | — | N | N | N | 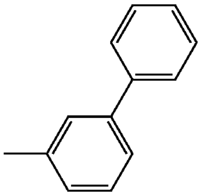 |
| 410 | S | 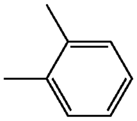 | 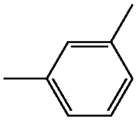 | N | N | N | 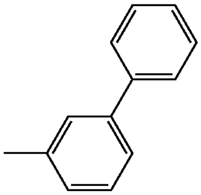 |
| 411 | O | 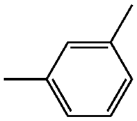 | 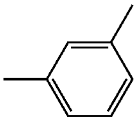 | N | CH | N | —Ph |
| 412 | S | — | 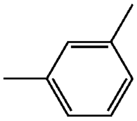 | CH | CH | N | —Ph |
| Compound No. | $Ar_2$ | $R_1$ | $R_2$ | Bonding position of $L_1$ | $R_3$ | Ra | Rb |
|---|---|---|---|---|---|---|---|
| 405 | —Ph | — | — | 3 | —Ph | — | — |
| 406 | —Ph | — | — | 3 | —Ph | — | — |
| 407 | —Ph | — | — | 2 | —Ph | — | — |
| 408 | — | — | — | 3 | —Ph | — | — |

-continued
| Formula (H3) | | | | | | | |
|---|---|---|---|---|---|---|---|
| 409 | 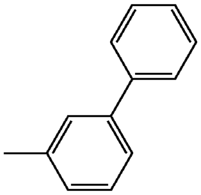 | — | — | 3 | —Ph | — | — |
| 410 | 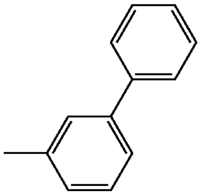 | — | —Ph (6) | 3 | —Ph | — | — |
| 411 | —Ph | — | — | 3 | 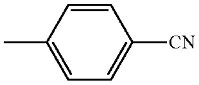 | — | — |
| 412 | —Ph | — | — | 2 | —Ph | — | — |
Formula (I1)
| Compound No. | X | $L_1$ | $L_2$ | $Y_1$ | $Y_2$ | $Y_3$ | $Ar_1$ |
|---|---|---|---|---|---|---|---|
| 413 | O | — | 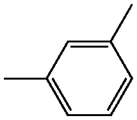 | N | N | N | —Ph |
| 414 | O | — | — | N | N | N | —Ph |
| 415 | S | — | — | N | N | CH | —Ph |
| 416 | S | 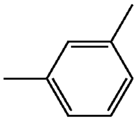 | — | N | C—Ph | N | —Ph |
| 417 | O | — | — | N | N | N | —Ph |
| 418 | S | 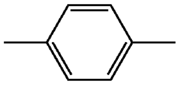 | — | N | N | N | 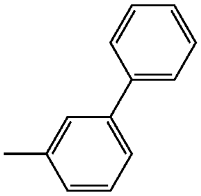 |
| 419 | O | 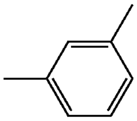 | 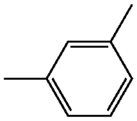 | N | CH | N | —Ph |

-continued
Formula (I1)
| | | | | | | | |
|---|---|---|---|---|---|---|---|
| 420 | S | — | 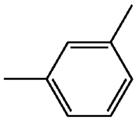 | CH | CH | N | —Ph |
| Compound No. | $Ar_2$ | $R_1$ | $R_2$ | Ra | Rb |
|---|---|---|---|---|---|
| 413 | —Ph | — | — | — | — |
| 414 | —Ph | — | — | — | — |
| 415 | —Ph | — | — | — | — |
| 416 | — | — | — | — | — |
| 417 | —Ph | — | — | — | —Ph (5) |
| 418 | 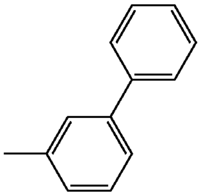 | —Ph (3) | — | — | — |
| 419 | —Ph | — | — | — | — |
| 420 | —Ph | — | — | —Ph (4) | — |
Formula (I2)
| Compound No. | X | $L_1$ | $L_2$ | $Y_1$ | $Y_2$ | $Y_3$ | $Ar_1$ |
|---|---|---|---|---|---|---|---|
| 421 | O | — | 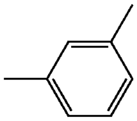 | N | N | N | —Ph |
| 422 | O | — | — | N | N | N | —Ph |
| 423 | S | — | — | N | N | CH | 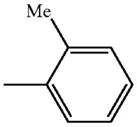 |
| 424 | S | 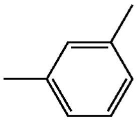 | — | N | C—Ph | N | —Ph |
| 425 | O | — | — | N | N | N | —Ph |
| 426 | S | 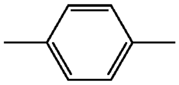 | — | N | N | N | 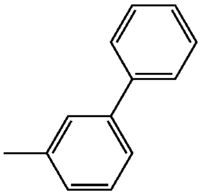 |

-continued
| Formula (I2) | | | | | | | |
|---|---|---|---|---|---|---|---|
| 427 | O | 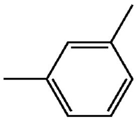 | 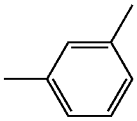 | N | CH | N | —Ph |
| 428 | O | — | 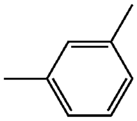 | CH | CH | N | —Ph |
| Compound No. | $Ar_2$ | $R_1$ | $R_2$ | Ra | Rb |
|---|---|---|---|---|---|
| 421 | —Ph | — | — | — | — |
| 422 | —Ph | — | — | — | 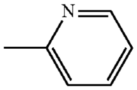 (5) |
| 423 | 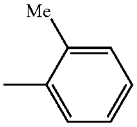 | — | — | — | — |
| 424 | — | — | — | — | — |
| 425 | —Ph | — | — | — | — |
| 426 | 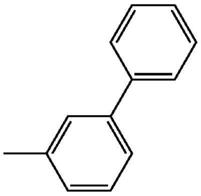 | —Ph (3) | — | — | — |
| 427 | —Ph | — | — | — | — |
| 428 | —Ph | — | — | — | — |
| Formula (I3) | | | | | | | |
|---|---|---|---|---|---|---|---|
| Compound No. | X | $L_1$ | $L_2$ | $Y_1$ | $Y_2$ | $Y_3$ | $Ar_1$ |
| 429 | O | — | 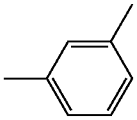 | N | N | N | —Ph |
| 430 | O | — | — | N | N | N | —Ph |
| 431 | S | — | — | N | N | CH | —Ph |
| 432 | S | 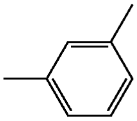 | — | N | C—Ph | N | —Ph |
| 433 | O | — | — | N | N | N | —Ph |

-continued
Formula (I3)
| | | | | | | | |
|---|---|---|---|---|---|---|---|
| 434 | S | 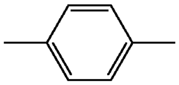 | — | N | N | N | 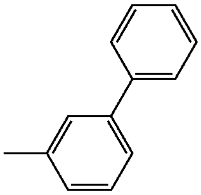 |
| 435 | O | 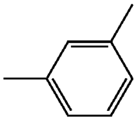 | 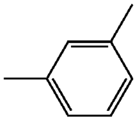 | N | CH | N | —Ph |
| 436 | O | — | 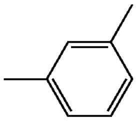 | CH | CH | N | —Ph |
| Compound No. | $Ar_2$ | $R_1$ | $R_2$ | Ra | Rb |
|---|---|---|---|---|---|
| 429 | —Ph | — | — | — | — |
| 430 | —Ph | — | — | — | — |
| 431 | —Ph | — | — | — | — |
| 432 | — | — | — | — | — |
| 433 | —Ph | — | — | — | 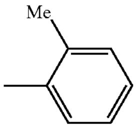 (5) |
| 434 | 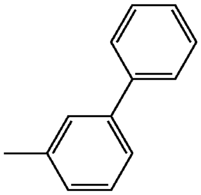 | —Ph (3) | — | — | — |
| 435 | —Ph | — | — | — | — |
| 436 | —Ph | — | — | — | — |
Formula (I4)
| Compound No. | X | $L_1$ | $L_2$ | $Y_1$ | $Y_2$ | $Y_3$ | $Ar_1$ |
|---|---|---|---|---|---|---|---|
| 437 | O | — | 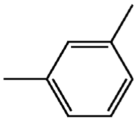 | N | N | N | —Ph |
| 438 | O | — | — | N | N | N | —Ph |
| 439 | S | — | — | N | N | CH | —Ph |

-continued
Formula (I4)
| | | | | | | | |
|---|---|---|---|---|---|---|---|
| 440 | S | 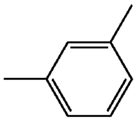 | — | N | C—Ph | N | —Ph |
| 441 | O | — | — | N | N | N | —Ph |
| 442 | S | 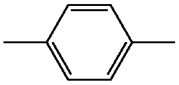 | — | N | N | N | 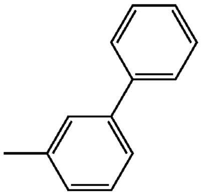 |
| 443 | O | 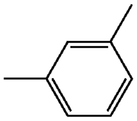 | 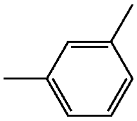 | N | CH | N | —Ph |
| 444 | O | — | 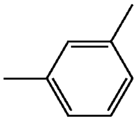 | CH | CH | N | —Ph |
| Compound No. | $Ar_2$ | $R_1$ | $R_2$ | Ra | Rb |
|---|---|---|---|---|---|
| 437 | —Ph | — | — | — | — |
| 438 | —Ph | — | — | — | — |
| 439 | —Ph | — | — | — | — |
| 440 | — | — | — | — | — |
| 441 | —Ph | — | — | — | 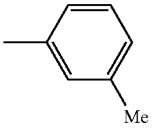 (5) |
| 442 | 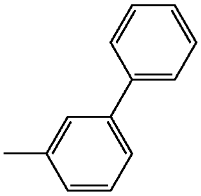 | —Ph (3) | — | — | — |
| 443 | —Ph | — | — | — | — |
| 444 | —Ph | — | — | — | — |
Formula (J1)
| Compound No. | X | $L_1$ | $L_2$ | $Y_1$ | $Y_2$ | $Y_3$ | $Ar_1$ |
|---|---|---|---|---|---|---|---|
| 445 | O | — | 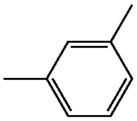 | N | N | N | —Ph |

-continued
Formula (J1)
| | | | | | | | |
|---|---|---|---|---|---|---|---|
| 446 | O | — | — | N | N | N | —Ph |
| 447 | S | — | — | N | N | CH | —Ph |
| 448 | S | 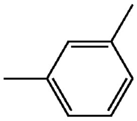 | N | C—Ph | N | —Ph | — |
| 449 | O | — | — | N | N | N | —Ph |
| 450 | S | 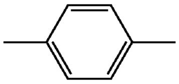 | — | N | N | N | 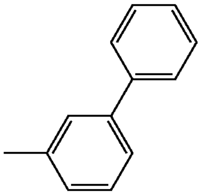 |
| 451 | O | 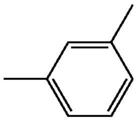 | 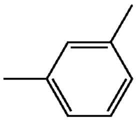 | N | CH | N | —Ph |
| 452 | O | — | 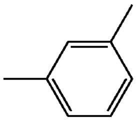 | CH | CH | N | —Ph |
| Compound No. | $Ar_2$ | $R_1$ | $R_2$ | Ra | Rb |
|---|---|---|---|---|---|
| 445 | —Ph | — | — | — | — |
| 446 | —Ph | — | — | — | — |
| 447 | —Ph | — | — | — | — |
| 448 | — | — | — | — | — |
| 449 | —Ph | — | — | — | — |
| 450 | 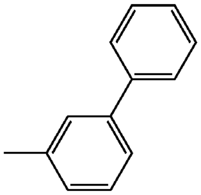 | —Ph (3) | — | — | — |
| 451 | —Ph | — | — | — | — |
| 452 | —Ph | — | — | — | — |
Formula (J2)
| Compound No. | X | $L_1$ | $L_2$ | $Y_1$ | $Y_2$ | $Y_3$ | $Ar_1$ |
|---|---|---|---|---|---|---|---|
| 453 | O | — | 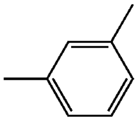 | N | N | N | —Ph |

-continued
Formula (J2)
| | | | | | | | |
|---|---|---|---|---|---|---|---|
| 454 | O | 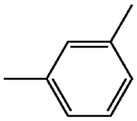 | — | N | N | N | —Ph |
| 455 | O | 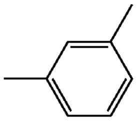 | 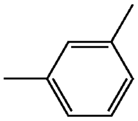 | N | N | N | —Ph |
| 456 | O | 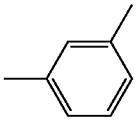 | — | N | N | C—Ph | —Ph |
| 457 | S | 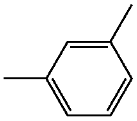 | 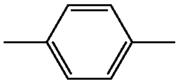 | N | N | N | —Ph |
| 458 | S | — | — | N | N | N | —Ph |
| 459 | O | 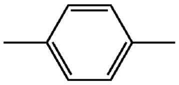 | 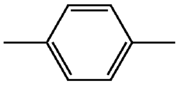 | N | N | N | —Ph |
| 460 | O | 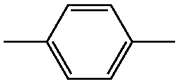 | — | N | N | N | —Ph |
| 461 | O | — | 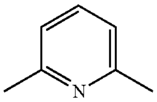 | N | CH | N | —Ph |
| 462 | O | 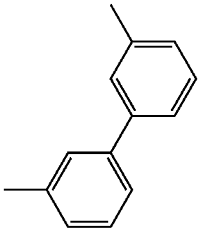 | — | N | N | CH | —Ph |
| 463 | O | 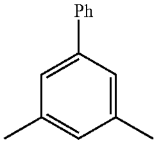 | — | N | N | N | —Ph |
| 464 | O | — | — | N | N | N | —Ph |
| 465 | O | 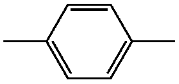 | — | N | N | N | 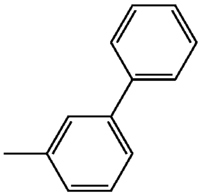 |

-continued
Formula (J2)
| | | | | | | | |
|---|---|---|---|---|---|---|---|
| 466 | O | 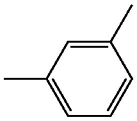 | 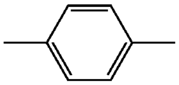 | N | N | N | —Ph |
| 467 | O | — | — | CH | N | N | — |
| 468 | O | — | — | N | C—Ph | N | — |
| 469 | O | — | — | N | N | N | —Ph |
| 470 | O | 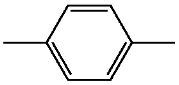 | — | N | N | N | —Ph |
| 471 | O | — | — | N | N | N | —Ph |
| 472 | O | — | — | N | CH | N | —Ph |
| 473 | S | — | 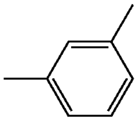 | N | N | N | —Ph |
| 474 | O | — | — | N | N | N | —tBu |
| 475 | S | — | — | N | N | N | —Ph |
| 476 | S | —$CH_2$— | — | N | N | N | 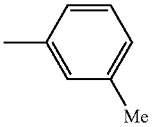 |
| 477 | O | 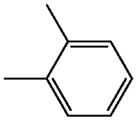 | — | N | N | N | —Ph |
| 478 | O | — | — | N | N | N | 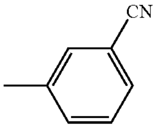 |
| 479 | S | 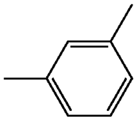 | —$(CH_2)_2$— | N | N | N | —Ph |
| 480 | O | — | — | N | N | N | —Ph |
| 481 | O | — | — | N | N | N | 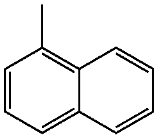 |
| 482 | S | — | — | N | N | N | —iPr |
| 483 | O | 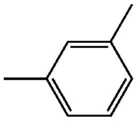 | — | N | N | N | —Ph |
| 484 | O | — | — | N | N | N | —Ph |

-continued
Formula (J2)
| Compound No. | $Ar_2$ | $R_1$ | $R_2$ | Ra | Rb |
|---|---|---|---|---|---|
| 453 | —Ph | — | — | — | — |
| 454 | —Ph | — | — | — | — |
| 455 | —Ph | — | — | — | — |
| 456 | — | — | — | — | — |
| 457 | —Ph | —Ph (3) | — | — | — |
| 458 | —Ph | — | — | — | — |
| 459 | —Ph | — | — | — | — |
| 460 | —Ph | — | — | — | — |
| 461 | —Ph | — | — | — | — |
| 462 | —Ph | — | — | — | — |
| 463 | —Ph | — | — | — | — |
| 464 | —Ph | — | — | — | — |
| 465 | 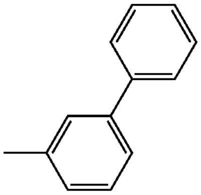 | —Ph (3) | — | — | — |
| 466 | —Ph | — | — | — | — |
| 467 | —Ph | — | — | — | — |
| 468 | — | — | — | — | — |
| 469 | —Ph | — | — | —Ph (4) | — |
| 470 | —Ph | — | — | — | —Ph (5) |
| 471 | 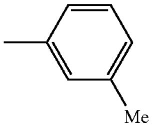 | — | — | — | — |
| 472 | —Ph | — | — | — | — |
| 473 | —Ph | — | — | — | — |
| 474 | —tBu | — | — | — | — |
| 475 | 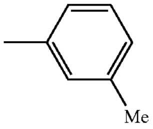 | — | — | — | — |
| 476 | —Ph | — | — | — | — |
| 477 | —Ph | — | — | — | — |
| 478 | 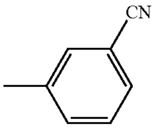 | — | — | — | — |
| 479 | —Ph | — | — | — | — |
| 480 | —Ph | — | —F (6) | — | — |
| 481 | 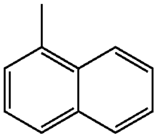 | — | — | — | — |
| 482 | —iPr | — | — | — | — |
| 483 | —Ph | — | — | — | — |
| 484 | —Ph | — | — | — | —Ph (5) |

Formula (J3)
| Compound No. | X | $L_1$ | $L_2$ | $Y_1$ | $Y_2$ | $Y_3$ | $Ar_1$ |
|---|---|---|---|---|---|---|---|
| 486 | O | — | 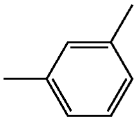 | N | N | N | —Ph |
| 487 | O | — | — | N | N | N | —Ph |
| 488 | S | — | — | N | N | CH | —Ph |
| 489 | S | 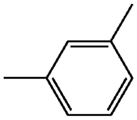 | — | N | C—Ph | N | —Ph |
| 490 | O | — | — | N | N | N | —Ph |
| 491 | S | 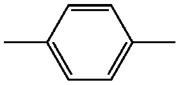 | — | N | N | N | 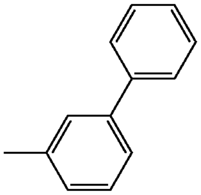 |
| 492 | O | 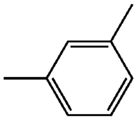 | 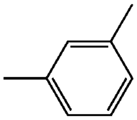 | N | CH | N | —Ph |
| 493 | O | — | 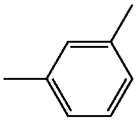 | CH | CH | N | —Ph |
| Compound No. | $Ar_2$ | $R_1$ | $R_2$ | Ra | Rb |
|---|---|---|---|---|---|
| 486 | —Ph | — | — | — | — |
| 487 | —Ph | — | — | — | — |
| 488 | —Ph | — | — | — | — |
| 489 | — | — | — | — | — |
| 490 | —Ph | — | — | — | — |
| 491 | 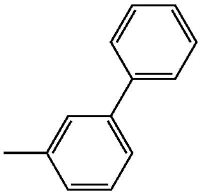 | —Ph(3) | — | — | — |
| 492 | —Ph | — | — | — | — |
| 493 | —Ph | — | — | — | — |

Formula (J4)
| Compound No. | X | $L_1$ | $L_2$ | $Y_1$ | $Y_2$ | $Y_3$ | $Ar_1$ |
|---|---|---|---|---|---|---|---|
| 494 | O | — | 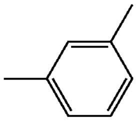 | N | N | N | —Ph |
| 495 | O | 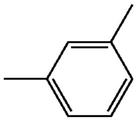 | — | N | N | N | —Ph |
| 496 | O | 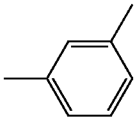 | 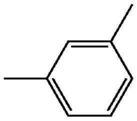 | N | N | N | —Ph |
| 497 | O | 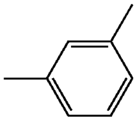 | — | N | N | C—Ph | —Ph |
| 498 | S | 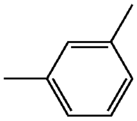 | 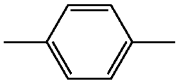 | N | N | N | —Ph |
| 499 | S | — | — | N | N | N | —Ph |
| 500 | O | 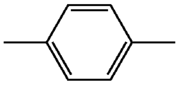 | 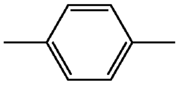 | N | N | N | —Ph |
| 501 | O | 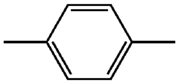 | — | N | N | N | —Ph |
| 502 | 0 | — | 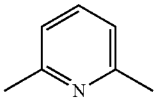 | N | CH | N | —Ph |
| 503 | O | 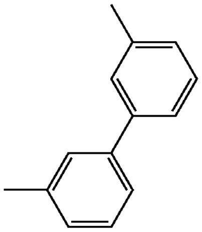 | — | N | N | N | —Ph |
| 504 | O | 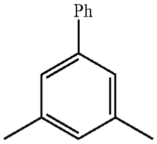 | — | N | N | N | —Ph |
| 505 | O | — | — | N | N | N | —Ph |

-continued
Formula (J4)
| | | | | | | | |
|---|---|---|---|---|---|---|---|
| 506 | O | 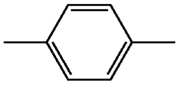 | — | N | N | N | 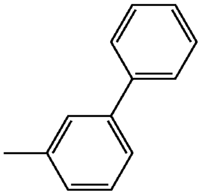 |
| 507 | O | 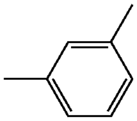 | 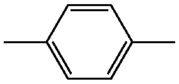 | N | N | N | —Ph |
| 508 | O | — | — | CH | N | N | — |
| 509 | O | — | — | N | C—Ph | N | — |
| 510 | O | — | — | N | N | N | —Ph |
| 511 | O | 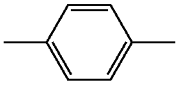 | — | N | N | N | —Ph |
| 512 | O | — | — | N | N | N | —Ph |
| 513 | O | — | — | N | CH | N | —Ph |
| 514 | S | — | 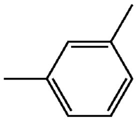 | N | N | N | —Ph |
| 515 | O | — | — | N | N | N | —tBu |
| 516 | S | — | — | N | N | N | —Ph |
| 517 | S | —$CH_2$— | — | N | N | N | 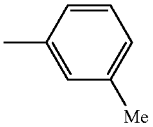 |
| 518 | O | 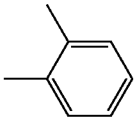 | — | N | N | N | —Ph |
| 519 | O | — | — | N | N | N | 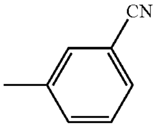 |
| 520 | S | 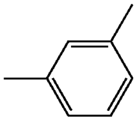 | —$(CH_2)_2$— | N | N | N | —Ph |
| 521 | O | — | — | N | N | N | —Ph |
| 522 | O | — | — | N | N | N | 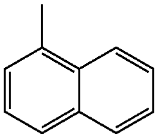 |
| 523 | S | — | — | N | N | N | —iPr |

-continued
Formula (J4)
| | | | | | | | |
|---|---|---|---|---|---|---|---|
| 524 | O | 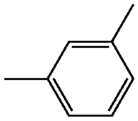 | — | N | N | N | —Ph |
| 525 | O | — | — | N | N | N | —Ph |
| 526 | O | — | 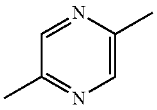 | N | N | N | —Ph |
| Compound No. | $Ar_2$ | $R_1$ | $R_2$ | Ra | Rb |
|---|---|---|---|---|---|
| 494 | —Ph | — | — | — | — |
| 495 | —Ph | — | — | — | — |
| 496 | —Ph | — | — | — | — |
| 497 | — | — | — | — | — |
| 498 | —Ph | —Ph (3) | — | — | — |
| 499 | —Ph | — | — | — | — |
| 500 | —Ph | — | — | — | — |
| 501 | —Ph | — | — | — | — |
| 502 | —Ph | — | — | — | — |
| 503 | —Ph | — | — | — | — |
| 504 | —Ph | — | — | — | — |
| 505 | —Ph | — | — | — | — |
| 506 | 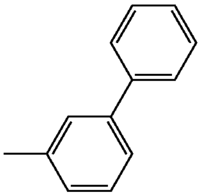 | —Ph (3) | — | — | — |
| 507 | —Ph | — | — | — | — |
| 508 | —Ph | — | — | — | — |
| 509 | — | — | — | — | — |
| 510 | —Ph | — | — | —Ph (2) | — |
| 511 | —Ph | — | — | — | —Ph (5) |
| 512 | 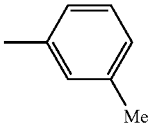 | — | — | — | — |
| 513 | —Ph | — | — | — | — |
| 514 | —Ph | — | — | — | — |
| 515 | —tBu | — | — | — | — |
| 516 | 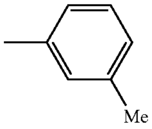 | — | — | — | — |
| 517 | —Ph | — | — | — | — |
| 518 | —Ph | — | — | — | — |
| 519 | 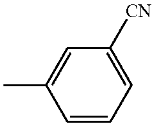 | — | — | — | — |
| 520 | —Ph | — | — | — | — |
| 521 | —Ph | — | —F (6) | — | — |

-continued
Formula (J4)
| | | | | | |
|---|---|---|---|---|---|
| 522 | 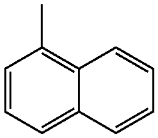 | — | — | — | — |
| 523 | —iPr | — | — | — | — |
| 524 | —Ph | — | — | — | — |
| 525 | —Ph | — | — | — | —Ph (5) |
| 526 | —Ph | — | — | — | — |
Formula (K1)
| Compound No. | X | $L_1$ | $L_2$ | $Y_1$ | $Y_2$ | $Y_3$ | $Ar_1$ |
|---|---|---|---|---|---|---|---|
| 527 | O | — | 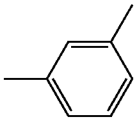 | N | N | N | —Ph |
| 528 | O | — | — | N | N | N | —Ph |
| 529 | S | — | — | N | N | CH | —Ph |
| 530 | S | 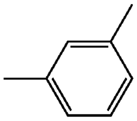 | — | N | C—Ph | N | —Ph |
| 531 | O | — | — | N | N | N | —Ph |
| 532 | S | 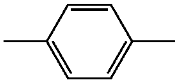 | — | N | N | N | 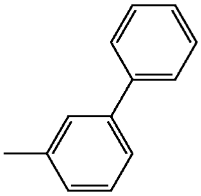 |
| 533 | O | 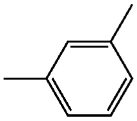 | 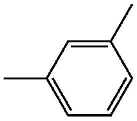 | N | CH | N | —Ph |
| 534 | S | — | 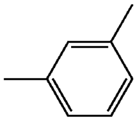 | CH | CH | N | —Ph |
| Compound No. | $Ar_2$ | $R_1$ | $R_2$ | Ra | Rb |
|---|---|---|---|---|---|
| 527 | —Ph | — | — | — | — |
| 528 | —Ph | — | — | — | — |
| 529 | —Ph | — | — | — | — |
| 530 | — | — | — | — | — |
| 531 | —Ph | — | — | — | —Ph (7) |

-continued
Formula (K1)
| | | | | | |
|---|---|---|---|---|---|
| 532 | 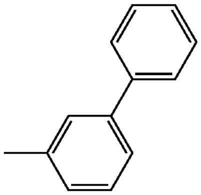 | —Ph (3) | — | — | — |
| 533 | —Ph | — | — | — | — |
| 534 | —Ph | — | — | —Ph (2) | — |
Formula (K2)
| Compound No. | X | $L_1$ | $L_2$ | $Y_1$ | $Y_2$ | $Y_3$ | $Ar_1$ |
|---|---|---|---|---|---|---|---|
| 535 | O | — | 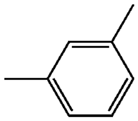 | N | N | N | —Ph |
| 536 | O | — | — | N | N | N | —Ph |
| 537 | S | — | — | N | N | CH | —Ph |
| 538 | S | 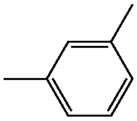 | — | N | C—Ph | N | —Ph |
| 539 | O | — | — | N | N | N | —Ph |
| 540 | S | 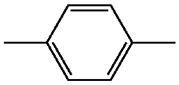 | — | N | N | N | 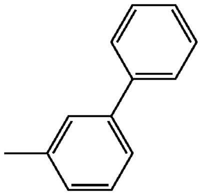 |
| 541 | O | 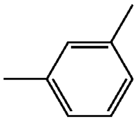 | 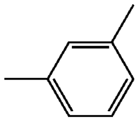 | N | CH | N | —Ph |
| 542 | S | — | 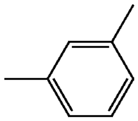 | CH | CH | N | —Ph |
| Compound No. | $Ar_2$ | $R_1$ | $R_2$ | Ra | Rb |
|---|---|---|---|---|---|
| 535 | —Ph | — | — | — | — |
| 536 | —Ph | — | — | — | — |
| 537 | —Ph | — | — | — | — |
| 538 | — | — | — | — | — |
| 539 | —Ph | — | — | — | —Ph (7) |

-continued
Formula (K2)
| | | | | | |
|---|---|---|---|---|---|
| 540 | 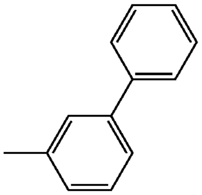 | —Ph (3) | — | — | — |
| 541 | —Ph | — | — | — | — |
| 542 | —Ph | — | — | —Ph (4) | — |
Formula (K3)
| Compound No. | X | $L_1$ | $L_2$ | $Y_1$ | $Y_2$ | $Y_3$ | $Ar_1$ |
|---|---|---|---|---|---|---|---|
| 543 | O | — | 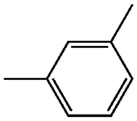 | N | N | N | —Ph |
| 544 | O | — | — | N | N | N | —Ph |
| 545 | S | — | — | N | N | CH | —Ph |
| 546 | S | 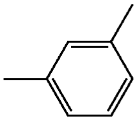 | — | N | C—Ph | N | —Ph |
| 547 | O | — | — | N | N | N | —Ph |
| 548 | S | 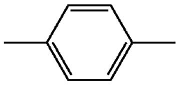 | — | N | N | N | 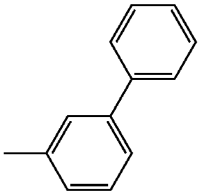 |
| 549 | O | 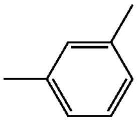 | 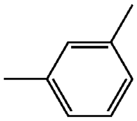 | N | CH | N | —Ph |
| 550 | S | — | 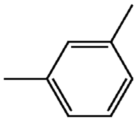 | CH | CH | N | —Ph |
| Compound No. | $Ar_2$ | $R_1$ | $R_2$ | Ra | Rb |
|---|---|---|---|---|---|
| 543 | —Ph | — | — | — | — |
| 544 | —Ph | — | — | — | — |
| 545 | —Ph | — | — | — | — |
| 546 | — | — | — | — | — |
| 547 | —Ph | — | — | — | —Ph (7) |

-continued
Formula (K3)
| | | | | | |
|---|---|---|---|---|---|
| 548 | 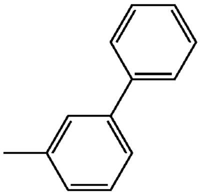 | —Ph (3) | — | — | — |
| 549 | —Ph | — | — | — | — |
| 550 | —Ph | — | — | —Ph (2) | — |
Formula (K4)
| Compound No. | X | $L_1$ | $L_2$ | $Y_1$ | $Y_2$ | $Y_3$ | $Ar_1$ |
|---|---|---|---|---|---|---|---|
| 551 | O | — | 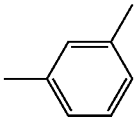 | N | N | N | —Ph |
| 552 | O | — | — | N | N | N | —Ph |
| 553 | S | — | — | N | N | CH | —Ph |
| 554 | S | 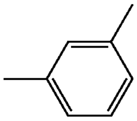 | — | N | C—Ph | N | —Ph |
| 555 | O | — | — | N | N | N | —Ph |
| 556 | S | 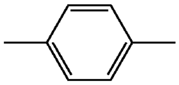 | — | N | N | N | 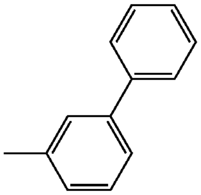 |
| 557 | O | 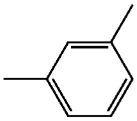 | 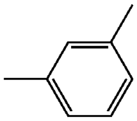 | N | CH | N | —Ph |
| 558 | S | — | 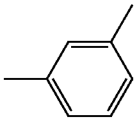 | CH | CH | N | —Ph |
| Compound No. | $Ar_2$ | $R_1$ | $R_2$ | Ra | Rb |
|---|---|---|---|---|---|
| 551 | —Ph | — | — | — | — |
| 552 | —Ph | — | — | — | — |
| 553 | —Ph | — | — | — | — |
| 554 | — | — | — | — | — |
| 555 | —Ph | — | — | — | —Ph (5) |

-continued
Formula (K4)
| | | | | | |
|---|---|---|---|---|---|
| 556 | 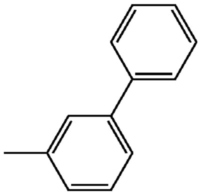 | —Ph (3) | — | — | — |
| 557 | —Ph | — | — | — | — |
| 558 | —Ph | — | — | —Ph (2) | — |
Formula (L1)
| Compound No. | X | $L_1$ | $L_2$ | $Y_1$ | $Y_2$ | $Y_3$ | $Ar_1$ |
|---|---|---|---|---|---|---|---|
| 559 | O | — | 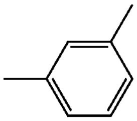 | N | N | N | —Ph |
| 560 | O | — | — | N | N | N | —Ph |
| 561 | S | — | — | N | N | CH | —Ph |
| 562 | S | 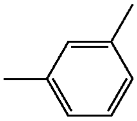 | — | N | C—Ph | N | —Ph |
| 563 | O | — | — | N | N | N | —Ph |
| 564 | S | 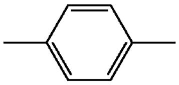 | — | N | N | N | 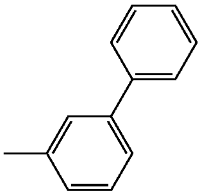 |
| 565 | O | 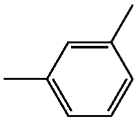 | 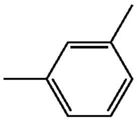 | N | CH | N | —Ph |
| 566 | S | — | 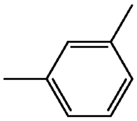 | CH | CH | N | —Ph |
| Compound No. | $Ar_2$ | $R_1$ | $R_2$ | Ra | Rb |
|---|---|---|---|---|---|
| 559 | —Ph | — | — | — | — |
| 560 | —Ph | — | — | — | — |
| 561 | —Ph | — | — | — | — |
| 562 | — | — | — | — | — |
| 563 | —Ph | — | — | — | —Ph (7) |

-continued
Formula (L1)
| | | | | | |
|---|---|---|---|---|---|
| 564 | 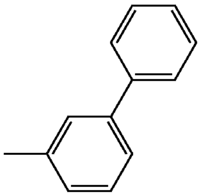 | —Ph (3) | — | — | — |
| 565 | —Ph | — | — | — | — |
| 566 | —Ph | — | — | —Ph (4) | — |
Formula (L2)
| Compound No. | X | $L_1$ | $L_2$ | $Y_1$ | $Y_2$ | $Y_3$ | $Ar_1$ |
|---|---|---|---|---|---|---|---|
| 567 | O | — | 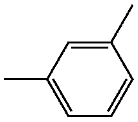 | N | N | N | —Ph |
| 568 | O | 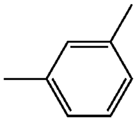 | — | N | N | N | —Ph |
| 569 | O | 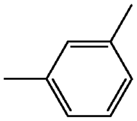 | 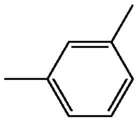 | N | N | N | —Ph |
| 570 | O | 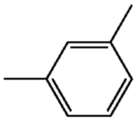 | — | N | C—Ph | N | —Ph |
| 571 | S | 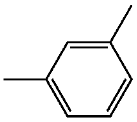 | 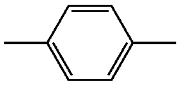 | N | N | N | —Ph |
| 572 | S | — | — | N | N | N | —Ph |
| 573 | O | 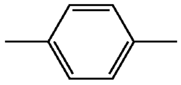 | 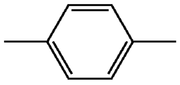 | N | N | N | —Ph |
| 574 | O | 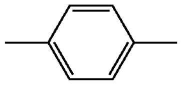 | — | N | N | N | —Ph |
| 575 | O | — | 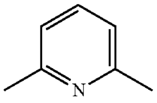 | N | N | N | —Ph |

-continued
| | | | Formula (L2) | | | | |
|---|---|---|---|---|---|---|---|
| 576 | O | 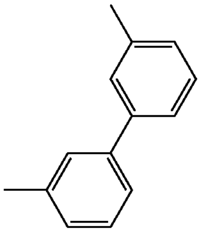 | — | N | N | N | —Ph |
| 577 | O | 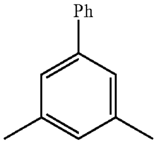 | — | N | N | N | —Ph |
| 578 | O | — | — | N | N | N | —Ph |
| 579 | O | 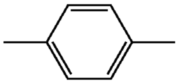 | — | N | N | N | 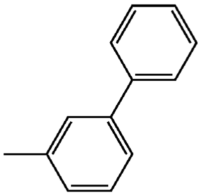 |
| 580 | O | 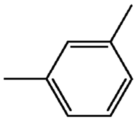 | 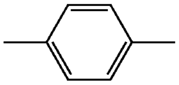 | N | N | N | —Ph |
| 581 | O | — | — | CH | N | N | — |
| 582 | O | — | — | N | C—Ph | N | — |
| 583 | O | — | — | N | N | N | —Ph |
| 584 | O | 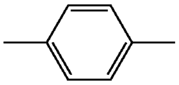 | — | N | N | N | —Ph |
| 585 | O | — | — | N | N | N | —Ph |
| 586 | O | — | — | N | CH | N | —Ph |
| 587 | S | — | 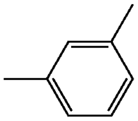 | N | N | N | —Ph |
| 588 | O | — | — | N | N | N | —tBu |
| 589 | S | — | — | N | N | N | —Ph |
| 590 | S | —$CH_2$— | — | N | N | N | 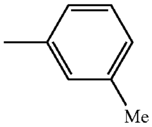 |
| 591 | O | 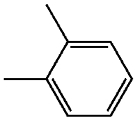 | — | N | N | N | —Ph |

-continued
| Formula (L2) | | | | | | | |
|---|---|---|---|---|---|---|---|
| 592 | O | — | — | N | N | N | 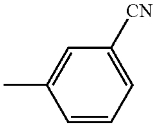 |
| 593 | S | 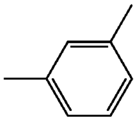 | —$(CH_2)_2$— | N | N | N | —Ph |
| 594 | O | — | — | N | N | N | —Ph |
| 595 | O | — | — | N | N | N | 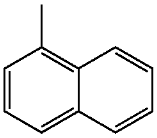 |
| 596 | S | — | — | N | N | N | —iPr |
| 597 | O | 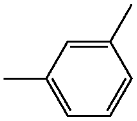 | — | N | N | N | —Ph |
| 598 | O | — | — | N | N | N | —Ph |
| 599 | O | — | 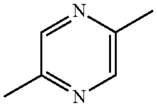 | N | N | N | —Ph |
| Compound No. | $Ar_2$ | $R_1$ | $R_2$ | Ra | Rb |
|---|---|---|---|---|---|
| 567 | —Ph | — | — | — | — |
| 568 | —Ph | — | — | — | — |
| 569 | —Ph | — | — | — | — |
| 570 | — | — | — | — | — |
| 571 | —Ph | —Ph (3) | — | — | — |
| 572 | —Ph | — | — | — | — |
| 573 | —Ph | — | — | — | — |
| 574 | —Ph | — | — | — | — |
| 575 | —Ph | — | — | — | — |
| 576 | —Ph | — | — | — | — |
| 577 | —Ph | — | — | — | — |
| 578 | —Ph | — | — | — | — |
| 579 | 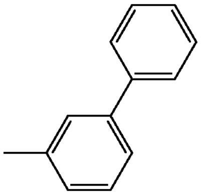 | —Ph (3) | — | — | — |
| 580 | —Ph | — | — | — | — |
| 581 | —Ph | — | — | — | — |
| 582 | — | — | — | — | — |
| 583 | —Ph | — | — | —Ph (4) | — |
| 584 | —Ph | — | — | — | —Ph (7) |
| 585 | 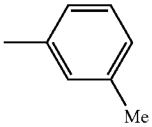 | — | — | — | — |

-continued
Formula (L2)
| | | | | | |
|---|---|---|---|---|---|
| 586 | —Ph | — | — | — | — |
| 587 | —Ph | — | — | — | — |
| 588 | —tBu | — | — | — | — |
| 589 | 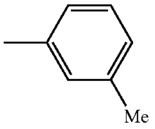 | — | — | — | — |
| 590 | —Ph | — | — | — | — |
| 591 | —Ph | — | — | — | — |
| 592 | 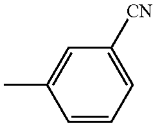 | — | — | — | — |
| 593 | —Ph | — | — | — | — |
| 594 | —Ph | — | —F (6) | — | — |
| 595 | 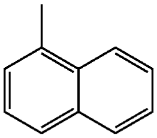 | — | — | — | — |
| 596 | —iPr | — | — | — | — |
| 597 | —Ph | — | — | — | — |
| 598 | —Ph | — | — | — | —Ph (7) |
| 599 | —Ph | — | — | — | — |
Formula (L3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 600 | O | — | 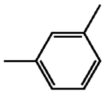 | N | N | N | —Ph | —Ph | — | — | — | — |
| 601 | O | — | — | N | N | N | —Ph | —Ph | — | — | — | — |
| 602 | S | — | — | N | N | CH | —Ph | —Ph | — | — | — | — |
| 603 | S | 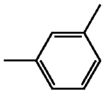 | — | N | C—Ph | N | —Ph | — | — | — | — | — |
| 604 | O | — | — | N | N | N | —Ph | —Ph | — | — | — | —Ph (7) |
| 605 | S | 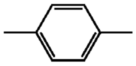 | — | N | N | N | 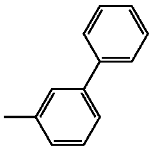 | 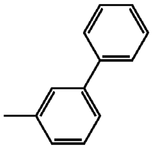 | —Ph (3) | — | — | — |
| 606 | O | 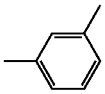 | 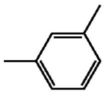 | N | CH | N | —Ph | —Ph | — | — | — | — |

-continued
| Formula (L3) | | | | | | | | | | | | |
|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 607 | S | — | 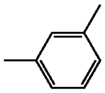 | CH | CH | N | —Ph | —Ph | — | — | —Ph (2) | — |
| Formula (L4) | | | | | | | | | | | | |
|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 608 | O | — | 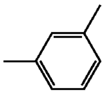 | N | N | N | —Ph | —Ph | — | — | — | — |
| 609 | O | 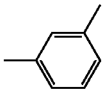 | — | N | N | N | —Ph | —Ph | — | — | — | — |
| 610 | O | 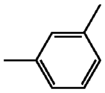 | 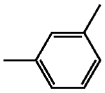 | N | N | N | —Ph | —Ph | — | — | — | — |
| 611 | O | 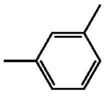 | — | N | C—Ph | N | —Ph | — | — | — | — | — |
| 612 | S | 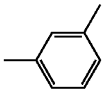 | 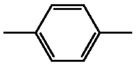 | N | N | N | —Ph | —Ph | —Ph (3) | — | — | — |
| 613 | S | — | — | N | N | N | —Ph | —Ph | — | — | — | — |
| 614 | O | 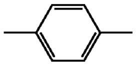 | 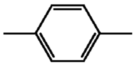 | N | N | N | —Ph | —Ph | — | — | — | — |
| 615 | O | 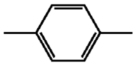 | — | N | N | N | —Ph | —Ph | — | — | — | — |
| 616 | O | — | 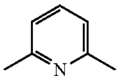 | N | CH | N | —Ph | —Ph | — | — | — | — |
| 617 | O | 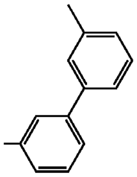 | — | N | N | CH | —Ph | —Ph | — | — | — | — |
| 618 | O | 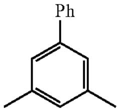 | — | N | N | N | —Ph | —Ph | — | — | — | — |
| 619 | O | — | — | N | N | N | —Ph | —Ph | — | — | — | — |

-continued
Formula (L4)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 620 | O | 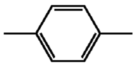 | — | N | N | N | 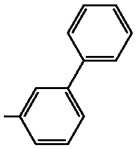 | 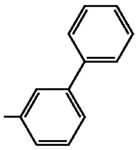 | —Ph (3) | — | — | — |
| 621 | O | 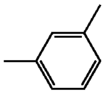 | 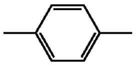 | N | N | N | —Ph | —Ph | — | — | — | — |
| 622 | O | — | — | CH | N | N | — | —Ph | — | — | — | — |
| 623 | O | — | — | N | C—Ph | N | — | — | — | — | — | — |
| 624 | O | — | — | N | N | N | —Ph | —Ph | — | — | —Ph (2) | — |
| 625 | O | 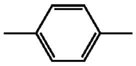 | — | N | N | N | —Ph | —Ph | — | — | — | —Ph (7) |
| 626 | O | — | — | N | N | N | —Ph | 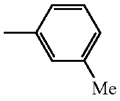 | — | — | — | — |
| 627 | O | — | — | N | CH | N | —Ph | —Ph | — | — | — | — |
| 628 | S | — | 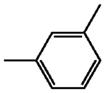 | N | N | N | —Ph | —Ph | — | — | — | — |
| 629 | O | — | — | N | N | N | —tBu | —tBu | — | — | — | — |
| 630 | S | — | — | N | N | N | —Ph | 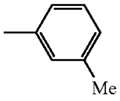 | — | — | — | — |
| 631 | S | $—CH_2—$ | — | N | N | N | 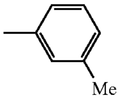 | —Ph | — | — | — | — |
| 632 | O | 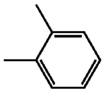 | — | N | N | N | —Ph | —Ph | — | — | — | — |
| 633 | O | — | — | N | N | N | 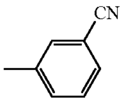 | 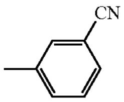 | — | — | — | — |
| 634 | S | 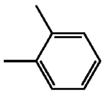 | $—(CH_2)_2—$ | N | N | N | —Ph | —Ph | — | — | — | — |
| 635 | O | — | — | N | N | N | —Ph | —Ph | — | —F (6) | — | — |
| 636 | O | — | — | N | N | N | 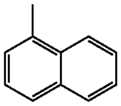 | 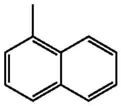 | — | — | — | — |
| 637 | S | — | — | N | N | N | —iPr | —iPr | — | — | — | — |

-continued
Formula (L4)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 638 | O | 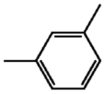 | — | N | N | N | —Ph | —Ph | — | — | — | — |
| 639 | O | — | — | N | N | N | —Ph | —Ph | — | — | — | —Ph (7) |
| 640 | O | — | 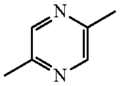 | N | N | N | —Ph | —Ph | — | — | — | — |
| 641 | O | — | 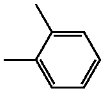 | N | N | N | —Ph | —Ph | — | — | — | — |
| 642 | O | — | 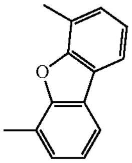 | N | N | N | —Ph | —Ph | — | — | — | — |
| 643 | S | — | 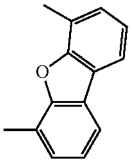 | N | CH | N | —Ph | —Ph | — | — | — | — |
| 644 | O | — | — | N | N | N | —Ph | —Ph | 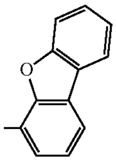 (3) | — | — | — |
Formula (M1)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 645 | O | — | 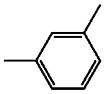 | N | N | N | —Ph | —Ph | — | — | — | — |
| 646 | O | — | — | N | N | N | —Ph | —Ph | — | — | — | — |
| 647 | S | — | — | N | N | CH | —Ph | —Ph | — | — | — | — |
| 648 | S | 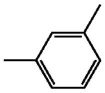 | — | N | C—Ph | N | —Ph | — | — | — | — | — |
| 649 | O | — | — | N | N | N | —Ph | —Ph | — | — | — | —Ph (7) |

-continued
| Formula (M1) | | | | | | | | | | | | |
|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 650 | S | 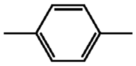 | — | N | N | N | 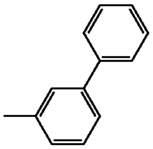 | 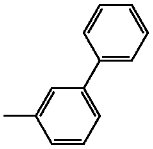 | —Ph (3) | — | — | — |
| 651 | O | 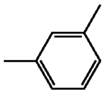 | 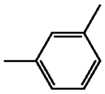 | N | CH | N | —Ph | —Ph | — | — | — | — |
| 652 | S | — | 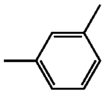 | CH | CH | N | —Ph | —Ph | — | — | —Ph (4) | — |
| Formula (M2) | | | | | | | | | | | | |
|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 653 | O | — | 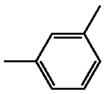 | N | N | N | —Ph | —Ph | — | — | — | — |
| 654 | O | — | — | N | N | N | —Ph | —Ph | — | — | — | — |
| 655 | S | — | — | N | N | CH | —Ph | —Ph | — | — | — | — |
| 656 | S | 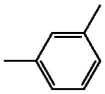 | — | N | C—Ph | N | —Ph | — | — | — | — | — |
| 657 | O | — | — | N | N | N | —Ph | —Ph | — | — | — | —Ph (5) |
| 658 | S | 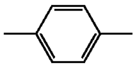 | — | N | N | N | 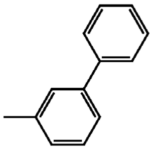 | 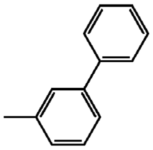 | —Ph (3) | — | — | — |
| 659 | O | 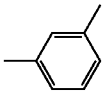 | 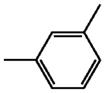 | N | CH | N | —Ph | —Ph | — | — | — | — |
| 660 | S | — | 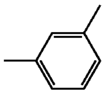 | CH | CH | N | —Ph | —Ph | — | — | —Ph (4) | — |

Formula (M3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 661 | O | — | 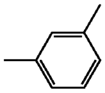 | N | N | N | —Ph | —Ph | — | — | — | — |
| 662 | O | — | — | N | N | N | —Ph | —Ph | — | — | — | — |
| 663 | S | — | — | N | N | CH | —Ph | —Ph | — | — | — | — |
| 664 | S | 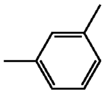 | — | N | C—Ph | N | —Ph | — | — | — | — | — |
| 665 | O | — | — | N | N | N | —Ph | —Ph | — | — | — | —Ph (7) |
| 666 | S | 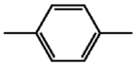 | — | N | N | N | 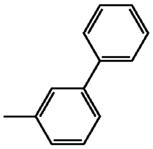 | 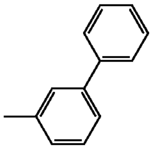 | —Ph (3) | — | — | — |
| 667 | O | 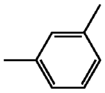 | 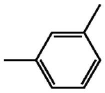 | N | CH | N | —Ph | —Ph | — | — | — | — |
| 668 | S | — | 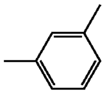 | CH | CH | N | —Ph | —Ph | — | — | —Ph (2) | — |
Formula (N1))
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 669 | O | — | 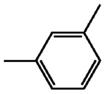 | N | N | N | —Ph | —Ph | — | — | — | — |
| 670 | O | — | — | N | N | N | —Ph | —Ph | — | — | — | — |
| 671 | S | — | — | N | N | CH | —Ph | —Ph | — | — | — | — |
| 672 | S | 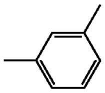 | — | N | C—Ph | N | —Ph | — | — | — | — | — |
| 673 | O | — | — | N | N | N | —Ph | —Ph | — | — | — | —Ph (5) |
| 674 | S | 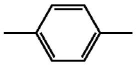 | — | N | N | N | 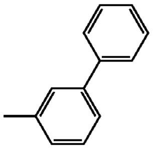 | 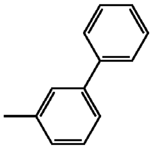 | —Ph (3) | — | — | — |
| 675 | 0 | 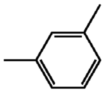 | 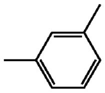 | N | CH | N | —Ph | —Ph | — | — | — | — |

-continued
Formula (N1))
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 676 | S | — | 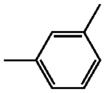 | CH | CH | N | —Ph | —Ph | — | — | —Ph (4) | — |
Formula (N2)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 677 | O | — | 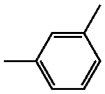 | N | N | N | —Ph | —Ph | — | — | — | — |
| 678 | O | — | — | N | N | N | —Ph | —Ph | — | — | — | — |
| 679 | S | — | — | N | N | CH | —Ph | —Ph | — | — | — | — |
| 680 | S | 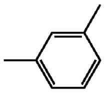 | — | N | C—Ph | N | —Ph | — | — | — | — | — |
| 681 | O | — | — | N | N | N | —Ph | —Ph | — | — | — | —Ph (7) |
| 682 | S | 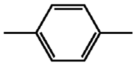 | — | N | N | N | 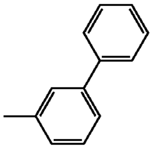 | 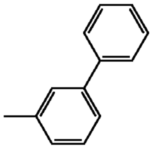 | —Ph (3) | — | — | — |
| 683 | O | 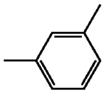 | 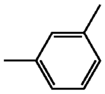 | N | CH | N | —Ph | —Ph | — | — | — | — |
| 684 | S | — | 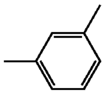 | CH | CH | N | —Ph | —Ph | — | — | —Ph (4) | — |
Formula (N3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 685 | O | — | 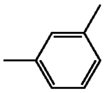 | N | N | N | —Ph | —Ph | — | — | — | — |
| 686 | O | 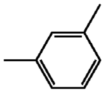 | — | N | N | N | —Ph | —Ph | — | — | — | — |

-continued
Formula (N3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 687 | O | 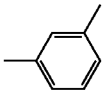 | 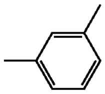 | N | N | N | —Ph | —Ph | — | — | — | — |
| 688 | O | 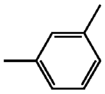 | — | N | C—Ph | N | —Ph | — | — | — | — | — |
| 689 | S | 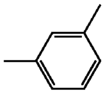 | 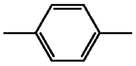 | N | N | N | —Ph | —Ph | —Ph (3) | — | — | — |
| 690 | S | — | — | N | N | N | —Ph | —Ph | — | — | — | — |
| 691 | O | 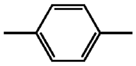 | 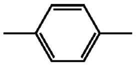 | N | N | N | —Ph | —Ph | — | — | — | — |
| 692 | O | 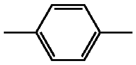 | — | N | N | N | —Ph | —Ph | — | — | — | — |
| 693 | O | — | 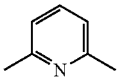 | N | CH | N | —Ph | —Ph | — | — | — | — |
| 694 | O | 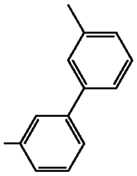 | — | N | N | CH | —Ph | —Ph | — | — | — | — |
| 695 | O | 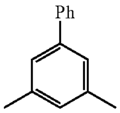 | — | N | N | N | —Ph | —Ph | — | — | — | — |
| 696 | O | — | — | N | N | N | —Ph | —Ph | — | — | — | — |
| 697 | O | 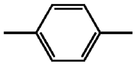 | — | N | N | N | 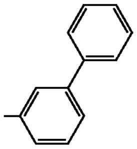 | 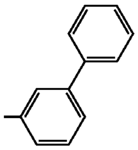 | —Ph (3) | — | — | — |
| 698 | O | 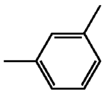 | 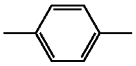 | N | N | N | —Ph | —Ph | — | — | — | — |
| 699 | O | — | — | CH | N | N | — | —Ph | — | — | — | — |
| 700 | O | — | — | N | C—Ph | N | — | — | — | — | — | — |
| 701 | O | — | — | N | N | N | —Ph | —Ph | — | — | — | —Ph (7) |
| 702 | O | 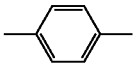 | — | N | N | N | —Ph | —Ph | — | — | — | —Ph (5) |

-continued
Formula (N3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 703 | O | — | — | N | N | N | —Ph | 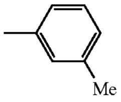 | — | — | — | — |
| 704 | O | — | — | N | CH | N | —Ph | —Ph | — | — | — | — |
| 705 | S | — | 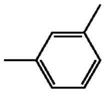 | N | N | N | —Ph | —Ph | — | — | — | — |
| 706 | O | — | — | N | N | N | —tBu | —tBu | — | — | — | — |
| 707 | S | — | — | N | N | N | —Ph | 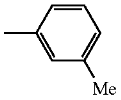 | — | — | — | — |
| 708 | S | $—CH_2—$ | — | N | N | N | 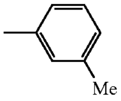 | —Ph | — | — | — | — |
| 709 | O | 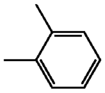 | — | N | N | N | —Ph | —Ph | — | — | — | — |
| 710 | O | — | — | N | N | N | 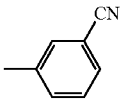 | 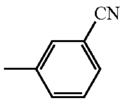 | — | — | — | — |
| 711 | S | 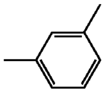 | $—(CH_2)_2—$ | N | N | N | —Ph | —Ph | — | — | — | — |
| 712 | O | — | — | N | N | N | —Ph | —Ph | — | —F (6) | — | — |
| 713 | O | — | — | N | N | N | 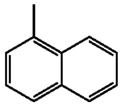 | 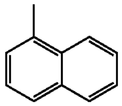 | — | — | — | — |
| 714 | S | — | — | N | N | N | —iPr | —iPr | — | — | — | — |
| 715 | O | 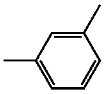 | — | N | N | N | —Ph | —Ph | — | — | — | — |
| 716 | O | — | — | N | N | N | —Ph | —Ph | — | — | — | —Ph (5) |
| 717 | O | — | 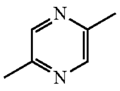 | N | N | N | —Ph | —Ph | — | — | — | — |
| 718 | O | — | 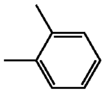 | N | N | N | —Ph | —Ph | — | — | — | — |

-continued
Formula (N3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 719 | O | — | 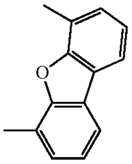 | N | N | N | —Ph | —Ph | — | — | — | — |
| 720 | S | — | 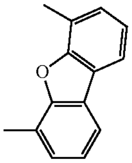 | N | CH | N | —Ph | —Ph | — | — | — | — |
| 721 | O | — | — | N | N | N | —Ph | —Ph | 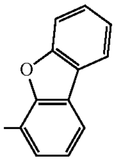 | — | — | — |
Formula (O1)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 722 | O | — | 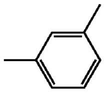 | N | N | N | —Ph | —Ph | — | — | — | — |
| 723 | O | — | — | N | N | N | —Ph | —Ph | — | — | — | — |
| 724 | S | — | — | N | N | CH | —Ph | —Ph | — | — | — | — |
| 725 | S | 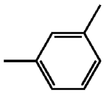 | — | N | C—Ph | N | —Ph | — | — | — | — | — |
| 726 | O | — | — | N | N | N | —Ph | —Ph | — | — | — | —Ph (7) |
| 727 | S | 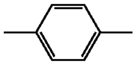 | — | N | N | N | 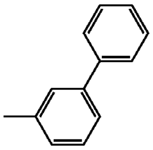 | 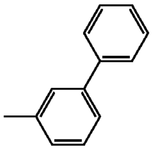 | —Ph (3) | — | — | — |
| 728 | O | 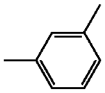 | 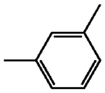 | N | CH | N | —Ph | —Ph | — | — | — | — |
| 729 | S | — | 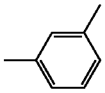 | CH | CH | N | —Ph | —Ph | — | — | —Ph (4) | — |

| Formula (O2) | | | | | | | | | | | |
|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 730 | O | — | 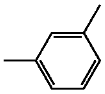 | N | N | N | —Ph | —Ph | — | — | — | — |
| 731 | O | — | — | N | N | N | —Ph | —Ph | — | — | — | — |
| 732 | S | — | — | N | N | CH | —Ph | —Ph | — | — | — | — |
| 733 | S | 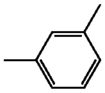 | — | N | C—Ph | N | —Ph | — | — | — | — | — |
| 734 | O | — | — | N | N | N | —Ph | —Ph | —nBu (3) | — | — | —Ph (7) |
| 735 | S | 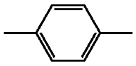 | — | N | N | N | 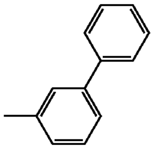 | 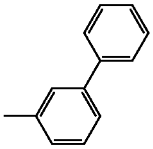 | —Ph (3) | — | — | — |
| 736 | O | 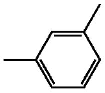 | 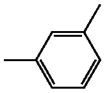 | N | CH | N | —Ph | —Ph | — | — | — | — |
| 737 | S | — | 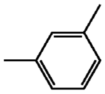 | CH | CH | N | —Ph | —Ph | — | — | —Ph (4) | — |
| Formula (O3) | | | | | | | | | | | | |
|---|---|---|---|---|---|---|---|---|---|---|---|---|
| Compound No. | X | $L_1$ | $L_2$ | $Y_1$ | $Y_2$ | $Y_3$ | $Ar_1$ | $Ar_2$ | $R_1$ | $R_2$ | Ra | Rb |
| 738 | O | — | 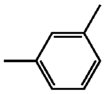 | N | N | N | —Ph | —Ph | — | — | — | — |
| 739 | O | — | — | N | N | N | —Ph | —Ph | — | — | — | — |
| 740 | S | — | — | N | N | CH | —Ph | —Ph | — | — | — | — |
| 741 | S | 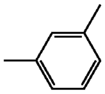 | — | N | C—Ph | N | —Ph | — | — | — | — | — |
| 742 | O | — | — | N | N | N | —Ph | —Ph | — | — | — | —Ph (5) |
| 743 | S | 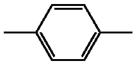 | — | N | N | N | 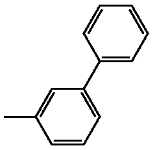 | 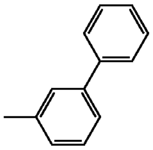 | —Ph (3) | — | — | — |
| 744 | O | 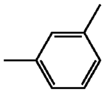 | 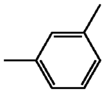 | N | CH | N | —Ph | —Ph | — | — | — | — |

-continued
Formula (O3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 745 | S | — | 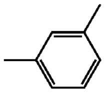 | CH | CH | N | —Ph | —Ph | — | — | —Ph (2) | — |
Formula (P1)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 746 | O | — | 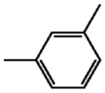 | N | N | N | —Ph | —Ph | — | — | — | — |
| 747 | O | — | — | N | N | N | —Ph | —Ph | — | — | — | — |
| 748 | S | — | — | N | N | CH | —Ph | —Ph | — | — | — | — |
| 749 | S | 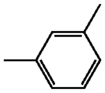 | — | N | C—Ph | N | —Ph | — | — | — | — | — |
| 750 | O | — | 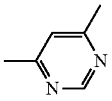 | N | N | N | —Ph | —Ph | — | — | — | —Ph (7) |
| 751 | S | 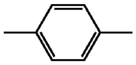 | — | N | N | N | 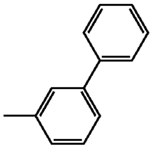 | 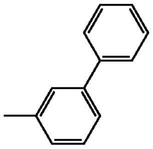 | —Ph (3) | — | — | — |
| 752 | O | 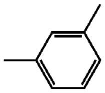 | 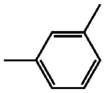 | N | CH | N | —Ph | —Ph | — | — | — | — |
| 753 | S | — | 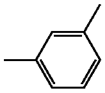 | CH | CH | N | —Ph | —Ph | — | — | —Ph (2) | — |
Formula (P2)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 754 | O | — | 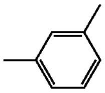 | N | N | N | —Ph | —Ph | — | — | — | — |
| 755 | O | 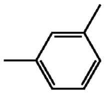 | — | N | N | N | —Ph | —Ph | — | — | — | — |

-continued
Formula (P2)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 756 | O | 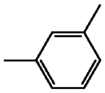 | 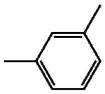 | N | N | N | —Ph | —Ph | — | — | — | — |
| 757 | O | 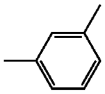 | — | N | C—Ph | N | —Ph | — | — | — | — | — |
| 758 | S | 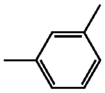 | 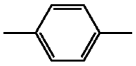 | N | N | N | —Ph | —Ph | —Ph (3) | — | — | — |
| 759 | S | — | — | N | N | N | —Ph | —Ph | — | — | — | — |
| 760 | O | 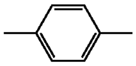 | 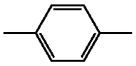 | N | N | N | —Ph | —Ph | — | — | — | — |
| 761 | O | 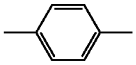 | — | N | N | N | —Ph | —Ph | — | — | — | — |
| 762 | O | — | 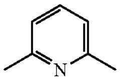 | N | CH | N | —Ph | —Ph | — | — | — | — |
| 763 | O | 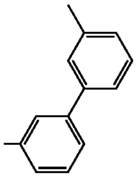 | — | N | N | CH | —Ph | —Ph | — | — | — | — |
| 764 | O | 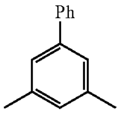 | — | N | N | N | —Ph | —Ph | — | — | — | — |
| 765 | O | — | — | N | N | N | —Ph | —Ph | — | — | — | — |
| 766 | O | 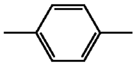 | — | N | N | N | 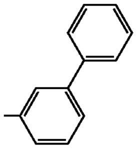 | 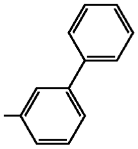 | —Ph (3) | — | — | — |
| 767 | O | 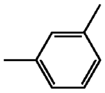 | 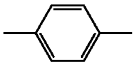 | N | N | N | —Ph | —Ph | — | — | — | — |
| 768 | O | — | — | CH | N | N | — | —Ph | — | — | — | — |
| 769 | O | — | — | N | C—Ph | N | — | — | — | — | — | — |
| 770 | O | — | — | N | N | N | —Ph | —Ph | — | — | — | —Ph (7) |
| 771 | O | 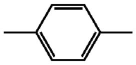 | — | N | N | N | —Ph | —Ph | — | — | — | —Ph (5) |
| 772 | O | — | — | N | N | N | —Ph | 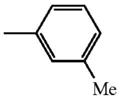 | — | — | — | — |

-continued
Formula (P2)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 773 | O | — | — | N | CH | N | —Ph | —Ph | — | — | — | — |
| 774 | S | — | 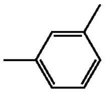 | N | N | N | —Ph | —Ph | — | — | — | — |
| 775 | O | — | — | N | N | N | —tBu | —tBu | — | — | — | — |
| 776 | S | — | — | N | N | N | —Ph | 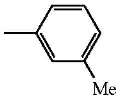 | — | — | — | — |
| 777 | S | $—CH_2—$ | — | N | N | N | 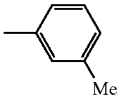 | —Ph | — | — | — | — |
| 778 | O | 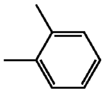 | — | N | N | N | —Ph | —Ph | — | — | — | — |
| 779 | O | — | — | N | N | N | 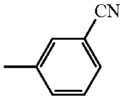 | 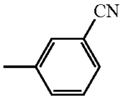 | — | — | — | — |
| 780 | S | 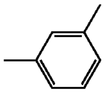 | $—(CH_2)_2—$ | N | N | N | —Ph | —Ph | — | — | — | — |
| 781 | O | — | — | N | N | N | —Ph | —Ph | — | —F (6) | — | — |
| 782 | O | — | — | N | N | N | 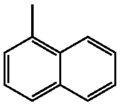 | 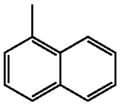 | — | — | — | — |
| 783 | S | — | — | N | N | N | —iPr | —iPr | — | — | — | — |
| 784 | O | 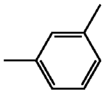 | — | N | N | N | —Ph | —Ph | — | — | — | — |
| 785 | O | — | — | N | N | N | —Ph | —Ph | — | — | — | —Ph (5) |
| 786 | O | — | 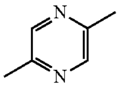 | N | N | N | —Ph | —Ph | — | — | — | — |
| 787 | O | — | 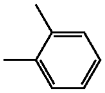 | N | N | N | —Ph | —Ph | — | — | — | — |
| 788 | O | — | 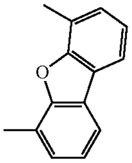 | N | N | N | —Ph | —Ph | — | — | — | — |

-continued
Formula (P2)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 789 | S | — | 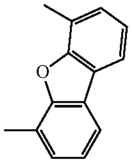 | N | CH | N | —Ph | —Ph | — | — | — | — |
| 790 | O | — | — | N | N | N | —Ph | —Ph | 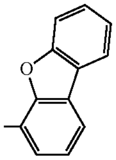 | — | — | — |
Formula (P3)
| Compound No. | X | $L_1$ | $L_2$ | $Y_1$ | $Y_2$ | $Y_3$ | $Ar_1$ | $Ar_2$ | $R_1$ | $R_2$ | Ra | Rb |
|---|---|---|---|---|---|---|---|---|---|---|---|---|
| 791 | O | — | 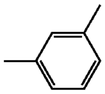 | N | N | N | —Ph | —Ph | — | — | — | — |
| 792 | O | — | — | N | N | N | —Ph | —Ph | — | — | — | — |
| 793 | S | — | — | N | N | CH | —Ph | —Ph | — | — | — | — |
| 794 | S | 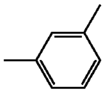 | — | N | C—Ph | N | —Ph | — | — | — | — | — |
| 795 | O | — | — | N | N | N | —Ph | —Ph | — | — | — | —Ph (7) |
| 796 | S | 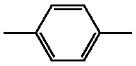 | — | N | N | N | 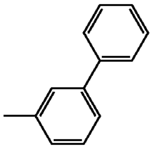 | 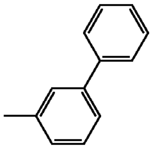 | —Ph (3) | — | — | — |
| 797 | O | 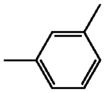 | 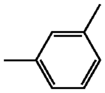 | N | CH | N | —Ph | —Ph | — | — | — | — |
| 798 | S | — | 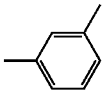 | CH | CH | N | —Ph | —Ph | — | — | —Ph (2) | — |

Exemplary compound 799

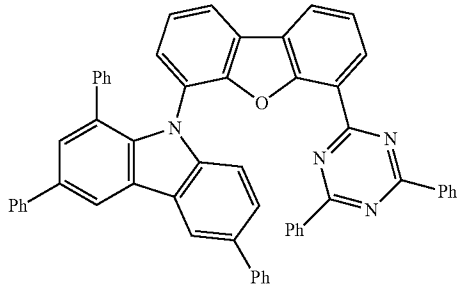

Exemplary compound 800

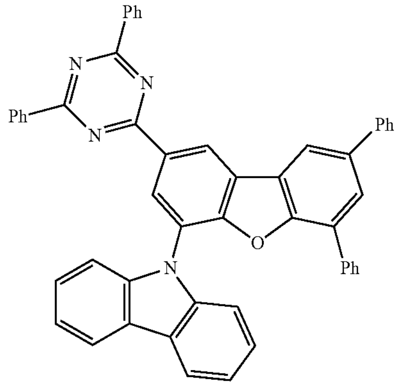

Exemplary compound 801

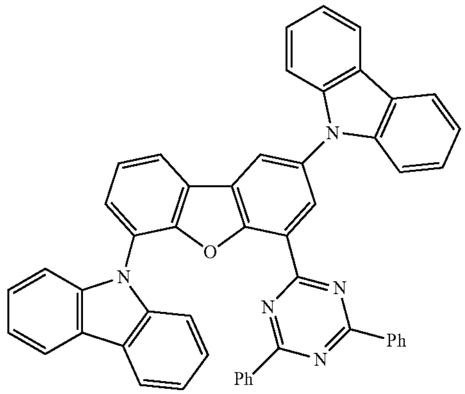

Exemplary compound 802

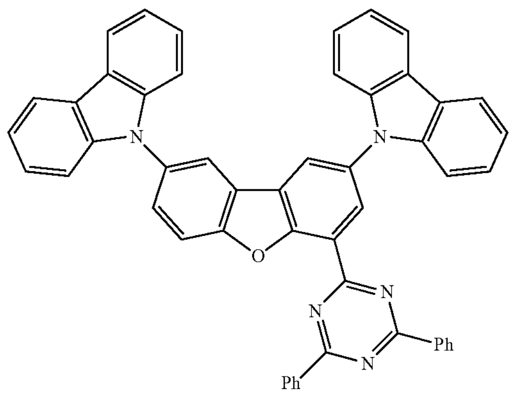

A heterocyclic derivative of the present invention preferably has a molecular weight of 800 or less from the viewpoint of making easy sublimation. More preferably, it has a molecular weight of 720 or less.

A compound of the present invention may be synthesized by using known synthetic methods. Examples of the synthetic methods are: a cross-coupling reaction using Pd for forming a carbon-carbon bond described in J. Org. Chem., 42, 1821 (1977), J. Am Chem. Soc., 101, 4992 (1977), Chem. Rev., 95, 2457 (1995), J. Med. Org. Chem., 53, 918 (1988); a cross-coupling reaction using Pd for forming a carbon-nitrogen bond described in Angew. Chem. Int. Ed., 1998, 37, 2046; and a carbon-nitrogen bond forming reaction using Cu described in Angew. Chem. Int. Ed., 2003, 42, 5400.

A synthesis of Exemplary compound 619 is described in the following as a specific synthetic example.

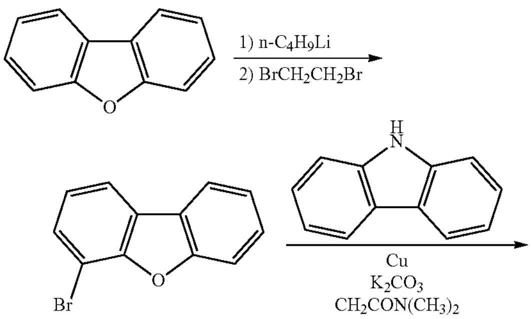

Intermediate 1

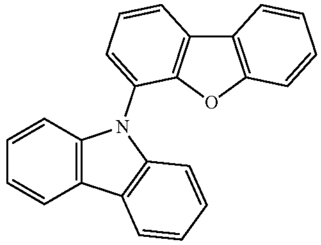

Intermediate 2

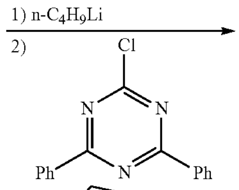

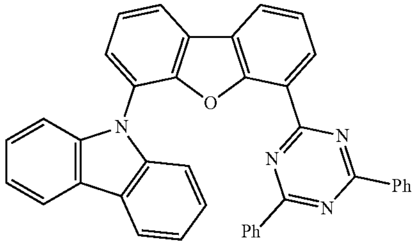

Exemplary compound 619

Synthesis of Intermediate 1

33.6 mg (200 mmol) of dibenzofuran was dissolved in 700 ml of THF under a nitrogen atmosphere. To this was added 350 ml of n-butyl lithium (1.6 mol/l hexane solution) at −70° C. or less. After completion of addition, the mixture was stirred at −70° C. or less for 1 hour. Then, the reaction mixture was heated to 0° C. and it was stirred for 1 hour. The reaction mixture was cooled again to −70° C. or less, and 45 g (300 ml) of 1,2-dibromoethane was added dropwise. After completion of drop, the reaction mixture was stirred for 12 hours. Then, water was added to the reaction mixture, and the reaction product was extracted with ethyl acetate. The organic layer was washed with water, and the solvent was removed under a reduced pressure. The produced residue was recrystallized with hexane to obtain 37.1 g of an intermediate 1. The yield was 75%. The structure of the compound was confirmed with NMR and mass spectrum.

Synthesis of Intermediate 2

24.7 g (100 mmol) of the intermediate 1 was dissolved in 200 ml of N,N-dimethyl acetamide under a nitrogen atmosphere. To this were added 17.6 g (105 mmol) of carbazole, 14.3 g (150 mmol) of copper powder, and 27.6 g (200 mmol) of potassium carbonate. Then the mixture was stirred at 170° C. for 12 hours. After cooling the reaction solution, it was poured into 500 ml of water. The precipitated solid was filtered. The filtered solid was dissolved in ethyl acetate, and an insoluble matter was removed with filtration. The solvent was removed from the filtrate under a reduced pressure. The obtained solid was recrystallized with methanol to obtain 33.3 g of an intermediate 2. The yield was 80%. The structure of the compound was confirmed with NMR and mass spectrum.

Synthesis of Exemplary Compound 619

16.7 g (50 mmol) of the intermediate 2 was dissolved in 300 ml of THF under a nitrogen atmosphere. To this was added 90 ml of n-butyl lithium (1.6 mol/l hexane solution) at −70° C. or less. After completion of addition, the mixture was stirred at −70° C. or less for 1 hour. Then, the reaction mixture was heated to 0° C. and it was stirred for 1 hour. The reaction mixture was cooled again to −70° C. or less, and to this was added a solution of 14.7 g (55 mmol) of 1-chloro-3,5-diphenyltriazine dissolved in 80 ml of THF. After completion of addition, the reaction mixture was stirred at room temperature for 6 hours. Then, water was added to the reaction mixture, and the precipitated product was filtered. The raw product was purified with silica gel chromatography then recrystallized with methanol. Further, the product was recrystallized with acetonitrile to obtain 25.4 g of an exemplary compound 619. The yield was 90%. The structure of the compound was confirmed with NMR and mass spectrum.

The other compounds of the present invention may be synthesized in the same method.

<<Constitution Layers of Organic EL Element>>

Representative element constitutions used for an organic EL element of the present invention are as follows, however, the present invention is not limited to these.

(1) Anode/light emitting layer/cathode (2) Anode/light emitting layer/electron transport layer/cathode (3) Anode/hole transport layer/light emitting layer/cathode (4) Anode/hole transport layer/light emitting layer/electron transport layer/cathode (5) Anode/hole transport layer/light emitting layer/electron transport layer/electron injection layer/cathode (6) Anode/hole injection layer/hole transport layer/light emitting layer/electron transport layer/cathode (7) Anode/hole injection layer/hole transport layer/(electron blocking layer/) light emitting layer/(hole blocking layer/) electron transport layer/electron injection layer/cathode Among these, the embodiment (7) is preferably used. However, the present invention is not limited to this.

The light emitting layer of the present invention is composed of one or a plurality of layers. When a plurality of layers are employed, it may be placed a non-light emitting intermediate layer between the light emitting layers.

According to necessity, it may be provided with a hole blocking layer (it is also called as a hole barrier layer) or an electron injection layer (it is also called as a cathode buffer layer) between the light emitting layer and the cathode. Further, it may be provided with an electron blocking layer (it is also called as an electron barrier layer) or an hole injection layer (it is also called as an anode buffer layer) between the light emitting layer and the anode.

An electron transport layer according to the present invention is a layer having a function of transporting an electron. An electron transport layer includes an electron injection layer, and a hole blocking layer in a broad sense. Further, an electron transport layer unit may be composed of plural layers.

A hole transport layer according to the present invention is a layer having a function of transporting a hole. A hole transport layer includes a hole injection layer, and an electron blocking layer in a broad sense. Further, a hole transport layer unit may be composed of plural layers.

In the representative element constitutions as described above, the layers eliminating an anode and a cathode are also called as “organic layers”.

(Tandem Structure)

An organic EL element of the present invention may be so-called a tandem structure element in which plural light emitting units each containing at least one light emitting are laminated.

A representative example of an element constitution having a tandem structure is as follows.

Anode/first light emitting unit/second light emitting unit/third light emitting unit cathode; and Anode, first light emitting unit intermediate layer/second light emitting unit/intermediate layer/third light emitting unit/cathode.

Here, the above-described first light emitting unit, second light emitting unit, and third light emitting unit may be the same or different. It may be possible that two light emitting units are the same and the remaining one light emitting unit is different.

In addition, the third light emitting unit may not be provided. Otherwise, a further light emitting unit or a further intermediate layer may be provided between the third light emitting unit and the electrode.

The plural light emitting units each may be laminated directly or they may be laminated through an intermediate layer. Examples of an intermediate layer are: an intermediate electrode, an intermediate conductive layer, a charge generating layer, an electron extraction layer, a connecting layer, and an intermediate insulating layer. Known composing materials may be used as long as it can form a layer which has a function of supplying an electron to an adjacent layer to the anode, and a hole to an adjacent layer to the cathode.

Examples of a material used in an intermediate layer are: conductive inorganic compounds such as ITO (indium tin oxide), IZO (indium zinc oxide), $ZnO_2$, TiN, ZrN, HfN, $TiO_X$, $VO_X$, CuI, InN, GaN, $CuAlO_2$, $CuGaO_2$, $SrCu_2O_2$, $LaB_6$, $RuO_2$, and Al; a two-layer film such as $Au/Bi_2O_3$; a multi-layer film such as $SnO_2/Ag/SnO_2$, ZnO/Ag/ZnO, $Bi_2O_3/Au/Bi_2O_3$, $TiO_2/TiN/TiO_2$, and $TiO_2/ZrN/TiO_2$; fullerene such as $C_{60}$; and a conductive organic layer such as oligothiophene, metal phthalocyanine, metal-free phthalocyanine, metal porphyrin, and metal-free porphyrin. The present invention is not limited to them.

Examples of a preferable constitution in the light emitting unit are the constitutions of the above-described (1) to (7) from which an anode and a cathode are removed. However, the present invention is not limited to them.

Examples of a tandem type organic EL element are described in: U.S. Pat. Nos. 6,337,492, 7,420,203, 7,473,923, 6,872,472, 6,107,734, 6,337,492, WO 2005/009087, JP-A 2006-228712, JP-A 2006-24791, JP-A 2006-49393, JP-A 2006-49394. JP-A 2006-49396, JP-A 2011-96679, JP-A 2005-340187, JP Patent 4711424, JP Patent 3496681, JP Patent 3884564, JP Patent 4213169, JP-A 2010-192719, JP-A 2009-076929, JP-A 2008-078414. JP-A 2007-059848, JP-A 2003-272860, JP-A 2003-045676, and WO 2005/094130. The constitutions of the elements and the composing materials are described in these documents, however, the present invention is not limited to them.

Each layer that constitutes an organic EL element of the present invention will be described in the following.

<<Light Emitting Layer>>

A light emitting layer according to the present invention is a layer which provide a place of emitting light via an exciton produce by recombination of electrons and holes injected from an electrode or an adjacent layer. The light emitting portion may be either within the light emitting layer or at an interface between the light emitting layer and an adjacent layer thereof. The constitution of the light emitting layer according to the present invention is not particularly limited as long as it satisfies the requirements of the present invention.

A total thickness of the light emitting layer is not particularly limited. However, in view of layer homogeneity, required voltage during light emission, and stability of the emitted light color against a drive electric current, the total layer thickness is preferably adjusted to be in the range of 2 nm to 5 μm, more preferably, it is in the range of 2 to 500 nm, and still most preferably, it is in the range of 5 to 200 nm.

Each light emitting layer is preferably adjusted to be in the range of 2 nm to 1 μm, more preferably, it is in the range of 2 to 200 nm, and still most preferably, it is in the range of 3 to 150 nm.

It is preferable that the light emitting layer of the present invention incorporates a light emitting dopant (it may be simply called as a dopant) and a host compound (it may be called as a light emitting host, or simply called as a host).

(1) Light Emitting Dopant

A light emitting dopant according to the present invention will be described.

As a light emitting dopant, it is preferable to employ: a fluorescence emitting dopant (also referred to as a fluorescent dopant and a fluorescent compound) and a phosphorescence emitting dopant (also referred to as a phosphorescent dopant and a phosphorescent emitting compound). In the present invention, it is preferable that at least one light emitting layer contains a phosphorescence emitting dopant.

A concentration of a light emitting compound in a light emitting layer may be arbitrarily decided based on the specific compound employed and the required conditions of the device. A concentration of a light emitting compound may be uniform in a thickness direction of the light emitting layer, or it may have any concentration distribution.

It may be used plural light emitting compounds of the present invention. It may be used a combination of fluorescent compounds each having a different structure, or a combination of a fluorescence emitting compound and a phosphorescence emitting compound. Any required emission color will be obtained by this.

Figure 4:
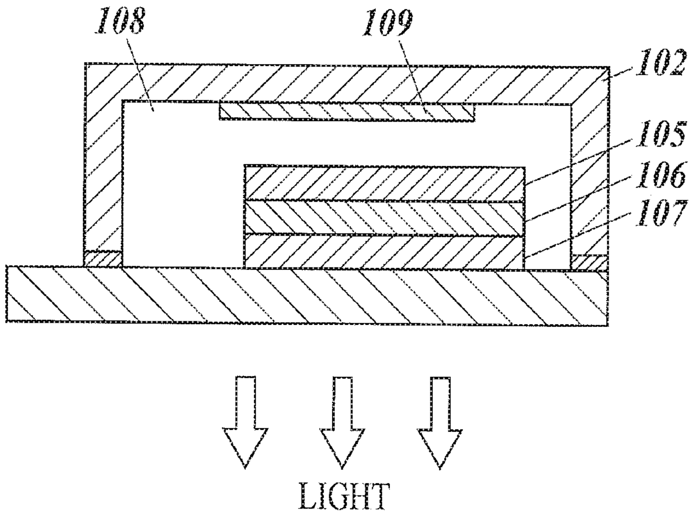
FIG. 4 is a schematic perspective drawing illustrating an example of a lighting device which uses an organic EL element of the present invention.

Color of light emitted by an organic EL element or a compound of the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via Spectroradiometer CS-1000 (produced by Konica Minolta, Inc.) are applied to the CIE chromaticity coordinate, whereby the color is specified.

In the present invention, it is preferable that the organic EL element of the present invention exhibits white emission by incorporating one or plural light emitting layers containing plural light emitting dopants having different emission colors.

The combination of light emitting dopants producing white is not specifically limited. It may be cited, for example, combinations of: blue and orange; and blue, green and red.

It is preferable that "white" in the organic EL element of the present invention exhibits chromaticity in the CIE 1931 Color Specification System at 1,000 cd/$m^2$ in the region of $x=0.39\pm0.09$ and $y=0.38\pm0.08$, when measurement is done to 2-degree viewing angle front luminance via the aforesaid method.

(1.1) Phosphorescence Emitting Dopant

A phosphorescence emitting dopant according to the present invention will be described. Hereafter, it may be called as "a phosphorescence dopant".

The phosphorescence emitting dopant is a compound which is observed emission from an excited triplet state thereof. Specifically, it is a compound which emits phosphorescence at a room temperature (25° C.) and exhibits a phosphorescence quantum yield of at least 0.01 at 25° C. The phosphorescence quantum yield is preferably at least 0.1.

The phosphorescence quantum yield will be determined via a method described in page 398 of Bunko II of Dai 4 Han Jikken Kagaku Koza 7 (Spectroscopy II of 4th Edition Lecture of Experimental Chemistry 7) (1992, published by Maruzen Co. Ltd.). The phosphorescence quantum yield in a solution will be determined using appropriate solvents. However, it is only necessary for the phosphorescent dopant of the present invention to exhibit the above phosphorescence quantum yield (0.01 or more) using any of the appropriate solvents.

Two kinds of principles regarding emission of a phosphorescent dopant are cited. One is an energy transfer-type, wherein carriers recombine on a host compound on which the carriers are transferred to produce an excited state of the host compound, and then via transfer of this energy to a phosphorescent dopant, emission from the phosphorescence-emitting dopant is realized. The other is a carrier trap-type, wherein a phosphorescence-emitting dopant serves as a carrier trap and then carriers recombine on the phosphorescent dopant to generate emission from the phosphorescent dopant. In each case, the excited state energy level of the phosphorescent dopant is required to be lower than that of the host compound.

A phosphorescence dopant may be suitably selected and employed from the known materials used for a light emitting layer for an organic EL element.

Examples of a known phosphorescence dopant are compounds described in the following publications.

Nature 395, 151 (1998), Appl. Phys. Lett. 78, 1622 (2001), Adv. Mater. 19, 739 (2007). Chem. Mater. 17, 3532 (2005), Adv. Mater. 17, 1059 (2005), WO 2009/100991, WO 2008/101842, WO 2003/040257, US 2006/835469, US 2006/0202194, US 2007/0087321, US 2005/0244673, Inorg. Chem. 40, 1704 (2001), Chem. Mater. 16, 2480 (2004), Adv. Mater. 16, 2003 (2004), Angew. Chem. Int. Ed. 2006, 45, 7800, Appl. Phys. Lett. 86, 153505 (2005), Chem. Lett. 34, 592 (2005). Chem. Commun. 2906 (2005), Inorg. Chem. 42, 1248 (2003), WO 2009/050290, WO 2002/015645, WO 2009/000673, US 2002/0034656, U.S. Pat. No. 7,332,232, US 2009/0108737, US 2009/0039776, U.S. Pat. Nos. 6,921,915, 6,687,266, US 2007/0190359, US 2006/0008670, US 2009/0165846, US 2008/0015355, U.S. Pat. No. 7,250,226. U.S. Pat. No. 7,396,598, US 2006/0263635, US 2003/0138657, US 2003/0152802, U.S. Pat. No. 7,090,928, Angew. Chem. Int. Ed. 47, 1 (2008), Chem. Mater. 18, 5119 (2006), Inorg. Chem. 46, 4308 (2007), Organometallics 23, 3745 (2004), Appl. Phys. Lett. 74, 1361 (1999), WO 2002/002714, WO 2006/009024, WO 2006/056418, WO 2005/019373, WO 2005/123873. WO 2005/123873, WO 2007/004380, WO 2006/082742, US 2006/0251923, US 2005/0260441, U.S. Pat. Nos. 7,393,599, 7,534,505, 7,445,855, US 2007/0190359, US 2008/0297033, U.S. Pat. No. 7,338,722, US 2002/0134984, and U.S. Pat. No. 7,279,704, US 2006/098120, US 2006/103874, WO 2005/076380, WO 2010/032663, WO 2008/140115, WO 2007/052431, WO 2011/134013, WO 2011/157339, WO 2010/086089, WO 2009/113646, WO 2012/020327, WO 2011/051404, WO 2011/004639, WO 2011/073149. JP-A 2012-069737, JP Application No. 2011-181303. JP-A 2009-114086. JP-A 2003-81988, JP-A 2002-302671 and JP-A 2002-363552.

Among them, preferable phosphorescence emitting dopants are organic metal complexes containing Ir as a center metal. More preferable are complexes containing at least one coordination mode selected from a metal-carbon bond, a metal-nitrogen bond, a metal-oxygen bond and a metal-sulfur bond.

(1.2) Fluorescence Emitting Dopant

A fluorescence emitting dopant according to the present invention will be described. Hereafter, it may be called as “a fluorescence dopant”.

A fluorescence emitting dopant according to the present invention is a compound which is observed emission from an excited singlet state thereof. The compound is not limited as long as emission from an excited singlet state is observed.

As specific known fluorescence emitting dopants usable in the present invention, listed are compounds such as: an anthracene derivative, a pyrene derivative, a chrysene derivative, a fluoranthene derivative, a perylene derivative, a fluorene derivative, an arylacetylene derivative, a styrylarylene derivative, a styrylamine derivative, an arylamine derivative, a boron complex, a coumarin derivative, a pyran derivative, a cyanine derivative, a croconium derivative, a squarylium derivative, an oxobenzanthracene derivative, a fluorescein derivative, a rhodamine derivative, a pyrylium derivative, a perylene derivative, a polythiophene derivative, and a rare earth complex compound.

In recent years, it was developed a light emitting dopant utilizing delayed fluorescence. It may use this dopant.

Specific examples of a light emitting dopant utilizing delayed fluorescence are compounds described in: WO 2011/156793, JP-A 2011-213643, and JP-A 2010-93181. However, the present invention is not limited to them.

(2) Host Compound

A host compound according to the present invention is a compound which mainly plays a role of injecting or transporting a charge in a light emitting layer. In an organic EL element, an emission from the host compound itself is substantially not observed.

Preferably, it is a compound exhibiting a phosphorescent emission yield of less than 0.1 at a room temperature (25° C.), more preferably a compound exhibiting a phosphorescent emission yield of less than 0.01. Among the compounds incorporated in the light emitting layer, a mass ratio of the host compound in the light emitting layer is preferably at least 20%.

It is preferable that the excited energy level of the host compound is higher than the excited energy level of the dopant contained in the same layer.

Host compounds may be used singly or may be used in combination of two or more compounds. By using a plurality of host compounds, it is possible to adjust transfer of charge, thereby it is possible to achieve an organic EL element of high efficiency.

A host compound used in a light emitting layer of the present invention is not specifically limited. A known compound previously used in an organic EL element may be used. It may be a compound having a low molecular weight, or a polymer having a high molecular weight. Further, it may be a compound having a reactive group such as a vinyl group or an epoxy group.

As a known host compound, preferably, it has a hole transporting ability or an electron transporting ability, as well as preventing elongation of an emission wavelength. In addition, from the viewpoint of stably driving an organic EL element at high temperature, it is preferable that a host compound has a high glass transition temperature (T) of 90° C. or more, more preferably, has a Tg of 120° C. or more.

Here, a glass transition temperature (Tg) is a value obtained using DSC (Differential Scanning Colorimetry) based on the method in conformity to JIS-K-7121.

As specific examples of a known host compound used in an organic EL element of the present invention, the compounds described in the following Documents are cited. However, the present invention is not to them.

Japanese patent application publication (JP-A) Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837; US Patent Application Publication (US) Nos. 2003/0175553, 2006/0280965, 2005/0112407, 2009/0017330, 2009/0030202, 2005/0238919; WO 2001/039234, WO 2009/02126, WO 2008/056746, WO 2004/093207, WO 2005/089025, WO 2007/063796, WO 2007/063754, WO 2004/107822, WO 2005/030900, WO 2006/114966, WO 2009/086028, WO 2009/003898, WO 2012/023947, JP-A 2008-074939, JP-A 2007-254297, and EP 2034538.

<<Electron Transport Layer>>

An electron transport layer of the present invention is composed of a material having a function of transferring an electron. It is only required to have a function of transporting an injected electron from a cathode to a light emitting layer.

A total layer thickness of the electron transport layer is not specifically limited, however, it is generally in the range of 2 nm to 5 μm, and preferably, it is in the range of 2 to 500 nm, and more preferably, it is in the range of 5 to 200 nm.

In an organic EL element, it is known that there occurs interference between the light directly taken from the light emitting layer and the light reflected at the electrode located at the opposite side of the electrode from which the light is taken out at the moment of taking out the light which is produced in the light emitting layer. When the light is reflected at the cathode, it is possible to use effectively this interference effect by suitably adjusting the total thickness of the electron transport layer in the range of 5 nm to 1 μm.

On the other hand, the voltage will be increased when the layer thickness of the electron transport layer is made thick. Therefore, especially when the layer thickness is large, it is preferable that the electron mobility in the electron transport layer is $1\times10^{-5}$ $cm^2/Vs$ or more.

As a material used for an electron transport layer (hereafter, it is called as an electron transport material), it is only required to have either a property of ejection or transport of electrons, or a barrier to holes. Any of the conventionally known compounds may be selected and they may be employed.

Cited examples thereof include: a nitrogen-containing aromatic heterocyclic derivative (a carbazole derivative, an azacarbazole derivative (a compound in which one or more carbon atoms constituting the carbazole ring are substitute with nitrogen atoms), a pyridine derivative, a pyrimidine derivative, a pyrazine derivative, a pyridazine derivative, a triazine derivative, a quinoline derivative, a quinoxaline derivative, a phenanthroline derivative, an azatriphenylene derivative, an oxazole derivative, a thiazole derivative, an oxadiazole derivative, a thiadiazole derivative, a triazole derivative, a benzimidazole derivative, a benzoxazole derivative, and a benzothiazole derivative); a dibenzofuran derivative, a dibenzothiophene derivative, a silole derivative; and an aromatic hydrocarbon ring derivative (a naphthalene derivative, an anthracene derivative and a triphenylene derivative).

Further, metal complexes having a ligand of a 8-quinolinol structure or dibnenzoquinolinol structure such as tris(8-quinolinol)aluminum ($Alq_3$), tris(5,7-dichloro-8-quinolinol) aluminum, tris(5,7-dibromo-8-quinolinol)aluminum, tris(2-methyl-8-quinolinol)aluminum, tris(5-methyl-8-quinolinol) aluminum and bis(8-quinolinol)zinc (Znq); and metal complexes in which a central metal of the aforesaid metal complexes is substituted by In, Mg, Cu, Ca, Sn, Ga or Pb, may be also utilized as an electron transport material.

Further, a metal-free or metal phthalocyanine, or a compound whose terminal is substituted by an alkyl group or a sulfonic acid group, may be preferably utilized as an electron transport material. A distyryl pyrazine derivative, which is exemplified as a material for a light emitting layer, may be used as an electron transport material. Further, in the same manner as used for a hole injection layer and a hole transport layer, an inorganic semiconductor such as an n-type Si and an n-type SiC may be also utilized as an electron transport material.

It may be used a polymer material introduced these compounds in the polymer side-chain or a polymer material having any one of these substance in a polymer main chain.

In an electron transport layer according to the present invention, it is possible to employ an electron transport layer of a higher n property (electron rich) which is doped with impurities as a guest material. As examples of a dope material, listed are those described in each of JP-A Nos. 4-297076, 10-270172, 2000-196140, 2001-102175, as well as in J. Appl. Phys., 95, 5773 (2004).

Although the present invention is not limited thereto, preferable examples of a known electron transport material used in an organic EL element of the present invention are compounds described in the following publications.

U.S. Pat. Nos. 6,528,187, 7,230,107, US 2005/0025993, US 2004/0036077, US 2009/0115316, US 2009/0101870, US 2009/0179554, WO 2003/060956, WO 2008/132085, Appl. Phys. Lett. 75, 4 (1999), Appl. Phys. Lett. 79, 449 (2001), Appl. Phys. Lett. 81, 162 (2002), Appl. Phys. Lett. 81, 162 (2002), Appl. Phys. Lett. 79, 156 (2001), U.S. Pat. No. 7,964,293, US 2009/030202, WO 2004/080975, WO 2004/063159, WO 2005/085387, WO 2006/067931, WO 2007/086552, WO 2008/114690, WO 2009/069442, WO 2009/066779, WO 2009/054253, WO 2011/086935, WO 2010/150593, WO 2010/047707, EP 2311826, JP-A 2010-251675, JP-A 2009-209133, JP-A 2009-124114, JP-A 2008-277810, JP-A 2006-156445. JP-A 2005-340122. JP-A 2003-45662, JP-A 2003-31367, JP-A 2003-282270, and WO 2012/115034.

Examples of a preferable electron transport material are: a pyridine derivative, a pyrimidine derivative, a pyrazine derivative, a triazine derivative, a dibenzofuran derivative, a dibenzothiophene derivative, a carbazole derivative, an azacarbazole derivative, and a benzimidazole derivative.

An electron transport material may be used singly, or may be used in combination of plural kinds of compounds.

<<Hole Blocking Layer>>

A hole blocking layer is a layer provided with a function of an electron transport layer in a broad meaning. Preferably, it contains a material having a function of transporting an electron, and having very small ability of transporting a hole. It will improve the recombination probability of an electron and a hole by blocking a hole while transporting an electron.

Further, a composition of an electron transport layer described above may be appropriately utilized as a hole blocking layer of the present invention when needed.

A hole blocking layer placed in an organic EL element of the present invention is preferably arranged at a location in the light emitting layer adjacent to the cathode side.

A thickness of a hole blocking layer according to the present invention is preferably in the range of 3 to 100 nm, and more preferably, in the range of 5 to 30 nm.

With respect to a material used for a hole blocking layer, the material used in the aforesaid electron transport layer is suitably used, and further, the material used as the aforesaid host compound is also suitably used for a hole blocking layer.

<<Electron Injection Layer>>

An electron injection layer (it is also called as "a cathode buffer layer") according to the present invention is a layer which is arranged between a cathode and a light emitting layer to decrease an operating voltage and to improve an emission luminance. An example of an electron injection layer is detailed in volume 2, chapter 2 "Electrode materials" (pp. 123-166) of "Organic EL Elements and Industrialization Front thereof (Nov. 30, 1998, published by N.T.S. Co. Ltd.)".

In the present invention, an electron injection layer is provided according to necessity, and as described above, it is placed between a cathode and a light emitting layer, or between a cathode and an electron transport layer.

An electron injection layer is preferably a very thin layer. The layer thickness thereof is preferably in the range of 0.1 to 5 nm depending on the materials used.

An election injection layer is detailed in JP-A Nos. 6-325871, 9-17574, and 10-74586. Examples of a material preferably used in an election injection layer include: a metal such as strontium and aluminum; an alkaline metal compound such as lithium fluoride, sodium fluoride, or potassium fluoride; an alkaline earth metal compound such as magnesium fluoride; a metal oxide such as aluminum oxide; and a metal complex such as lithium 8-hydroxyquinolate (Liq). It is possible to use the aforesaid electron transport materials.

The above-described materials may be used singly or plural kinds may be used together in an election injection layer.

<<Hole Transport Layer>>

In the present invention, a hole transport layer contains a material having a function of transporting a hole. A hole transport layer is only required to have a function of transporting a hole injected from an anode to a light emitting layer.

The total layer thickness of a hole transport layer of the present invention is not specifically limited, however, it is generally in the range of 5 nm to 5 μm, preferably in the range of 2 to 500 nm, and more preferably in the range of 5 nm to 200 nm.

A material used in a hole transport layer (hereafter, it is called as a hole transport material) is only required to have any one of properties of injecting and transporting a hole, and a barrier property to an electron. A hole transport material may be suitably selected from the conventionally known compounds.

Examples of a hole transport material include:

a porphyrin derivative, a phthalocyanine derivative, an oxazole derivative, an oxadiazole derivative, a triazole derivative, an imidazole derivative, a pyrazoline derivative, a pyrazolone derivative, a phenylenediamine derivative, a hydrazone derivative, a stilbene derivative, a polyarylalkane derivative, a triarylamine derivative, a carbazole derivative, an indolocarbazole derivative, an isoindole derivative, an acene derivative of anthracene or naphthalene, a fluorene derivative, a fluorenone derivative, polyvinyl carbazole, a polymer or an oligomer containing an aromatic amine in a side chain or a main chain, polysilane, and a conductive polymer or an oligomer (e.g., PEDOT:PSS, an aniline type copolymer, polyaniline and polythiophene).

Examples of a triarylamine derivative include: a benzidine type represented by α-NPD, a star burst type represented by MTDATA, a compound having fluorenone or anthracene in a triarylamine bonding core.

A hexaazatriphenylene derivative described in JP-A Nos. 2003-519432 and 2006-135145 may be also used as a hole transport material.

In addition, it is possible to employ an electron transport layer of a higher p property which is doped with impurities. As its example, listed are those described in each of JP-A Nos. 4-297076, 2000-196140, and 2001-102175, as well as in J. Appl. Phys., 95, 5773 (2004).

Further, it is possible to employ so-called p-type hole transport materials, and inorganic compounds such as p-type Si and p-type SiC, as described in JP-A No. 11-251067, and J. Huang et al. reference (Applied Physics Letters 80 (2002), p. 139). Moreover, an orthometal compounds having Ir or Pt as a center metal represented by $Ir(ppy)_3$ are also preferably used.

Although the above-described compounds may be used as a hole transport material, preferably used are: a triarylamine derivative, a carbazole derivative, an indolocarbazole derivative, an azatriphenylene derivative, an organic metal complex, a polymer or an oligomer incorporated an aromatic amine in a main chain or in a side chain.

Specific examples of a known hole transport material used in an organic EL element of the present invention are compounds in the aforesaid publications and in the following publications. However, the present invention is not limited to them.

Examples of a publication are: Appl. Phys. Lett. 69, 2160(1996), J. Lumin. 72-74, 985(1997), Appl. Phys. Lett. 78, 673(2001), Appl. Phys. Lett. 90, 183503(2007), Appl. Phys. Let 51,913(1987), Synth. Met. 87, 171(1997). Synth. Met. 91, 209(1997), Synth. Met. 111, 421(2000), SID Symposium Digest, 37, 923(2006), J. Mater. Chem. 3, 319 (1993), Adv. Mater. 6, 677(1994), Chem. Mater. 15, 3148 (2003), US 2003/0162053, US 2002/0158242, US 2006/0240279, US 2008/0220265, U.S. Pat. No. 5,061,569, WO 2007/002683, WO 2009/018009, EP 650955, US 2008/0124572, US 2007/0278938, US 2008/0106190, US 2008/0018221, WO 2012/115034, JP-A 2003-519432, JP-A 2006-135145, and U.S. patent application Ser. No. 13/585,981.

A hole transport material may be used singly or may be used in combination of plural kinds of compounds.

<<Electron Blocking Layer>>

An electron blocking layer is a layer provided with a function of a hole transport layer in a broad meaning. Preferably, it contains a material having a function of transporting a hole, and having very small ability of transporting an electron. It will improve the recombination probability of an electron and a hole by blocking an electron while transporting a hole.

Further, a composition of a hole transport layer described above may be appropriately utilized as an electron blocking layer of an organic EL element when needed.

An electron blocking layer placed in an organic EL element is preferably arranged at a location in the light emitting layer adjacent to the anode side.

A thickness of an electron blocking layer is preferably in the range of 3 to 100 nm, and more preferably, it is in the range of 5 to 30 nm.

With respect to a material used for an electron blocking layer, the material used in the aforesaid hole transport layer is suitably used, and further, the material used as the aforesaid host compound is also suitably used for an electron blocking layer.

<<Hole Injection Layer>>

A hole injection layer (it is also called as "an anode buffer layer") is a layer which is arranged between an anode and a light emitting layer to decrease an operating voltage and to improve an emission luminance. An example of a hole injection layer is detailed in volume 2, chapter 2 "Electrode materials" (pp. 123-166) of "Organic EL Elements and Industrialization Front thereof (Nov. 30, 1998, published by N.T.S. Co. Ltd.)".

A hole injection layer of the present invention is provided according to necessity, and as described above, it is placed between an anode and a light emitting layer, or between an anode and a hole transport layer.

A hole injection layer is also detailed in JP-A Nos. 9-45479, 9-260062 and 8-288069. As materials used in the hole injection layer, it is cited the same materials used in the aforesaid hole transport layer.

Among them, preferable materials are: a phthalocyanine derivative represented by copper phthalocyanine; a hexaazatriphenylene derivative described in JP-A Nos. 2003-519432 and 2006-135145, a metal oxide represented by vanadium oxide; a conductive polymer such as amorphous carbon, polyaniline (or called as emeraldine) and polythiophene; an orthometalated complex represented by tris(2-phenylpyridine) iridium complex; and a triarylamine derivative.

The above-described materials used in a hole injection layer may be used singly or plural kinds may be used in combination with.

<<Ingredient>>

The above-described organic layer of the present invention may further contain other ingredient.

Examples of an ingredient are: halogen elements such as bromine, iodine and chlorine, and a halide compound; and a compound, a complex and a salt of an alkali metal, an alkaline earth metal and a transition metal such as Pd, Ca and Na.

Although a content of an ingredient may be arbitrarily decided, preferably, it is 1,000 ppm or less based on the total mass of the layer containing the ingredient, more preferably, it is 500 ppm or less, and still more preferably, it is 50 ppm or less.

In order to improve a transporting property of an electron or a hole, or to facilitate energy transport of an exciton, the content of the ingredient is not necessarily within these range, and other range of content may be used.

<<Forming Method of Organic Layers>>

It will be described forming methods of organic layers according to the present invention (hole injection layer, hole transport layer, light emitting layer, hole blocking layer, electron transport layer, and electron injection layer).

Forming methods of organic layers according to the present invention are not specifically limited. They may be formed by using a known method such as a vacuum vapor deposition method and a wet method (it may be called as a wet process).

Examples of a wet process include: a spin coating method, a cast method, an inkjet method, a printing method, a die coating method, a blade coating method, a roll coating method, a spray coating method, a curtain coating method, and a LB method (Langmuir Blodgett method). From the viewpoint of getting a uniform thin layer with high productivity, preferable are method highly appropriate to a roll-to-roll method such as a die coating method, a roll coating method, an inkjet method, and a spray coating method.

Examples of a liquid medium to dissolve or to disperse a material for organic layers according to the present invention include: ketones such as methyl ethyl ketone and cyclohexanone; aliphatic esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decalin, and dodecane; organic solvents such as DMF and DMSO.

These will be dispersed with a dispersion method such as an ultrasonic dispersion method, a high shearing dispersion method and a media dispersion method.

A different film forming method may be applied to every organic layer. When a vapor deposition method is adopted for forming each layer, the vapor deposition conditions may be changed depending on the compounds used. Generally, the following ranges are suitably selected for the conditions, heating temperature of boat: 50 to 450° C., level of vacuum: $1\times10^{6}$ to $1\times10^{-2}$ Pa, vapor deposition rate: 0.01 to 50 nm/sec, temperature of substrate: −50 to 300° C., and layer thickness: 0.1 nm to 5 μm, preferably 5 to 200 nm.

Formation of organic layers of the present invention is preferably continuously carried out from a hole injection layer to a cathode with one time vacuuming. It may be taken out on the way, and a different layer forming method may be employed. In that case, the operation is preferably done under a dry inert gas atmosphere.

<<Anode>>

As an anode of an organic EL element, a metal having a large work function (4 eV or more, preferably, 4.5 eV or more), an alloy, and a conductive compound and a mixture thereof are utilized as an electrode substance.

Specific examples of an electrode substance are: metals such as Au, and an alloy thereof; transparent conductive materials such as CuI, indium tin oxide (ITO), $SnO_2$, and ZnO. Further, a material such as IDIXO ($In_2O_3$—ZnO), which may form an amorphous and transparent electrode, may also be used.

As for an anode, these electrode substances may be made into a thin layer by a method such as a vapor deposition method or a sputtering method; followed by making a pattern of a desired form by a photolithography method. Otherwise, when the requirement of pattern precision is not so severe (about 100 μm or more), a pattern may be formed through a mask of a desired form at the time of layer formation with a vapor deposition method or a sputtering method using the above-described material.

Alternatively, when a coatable substance such as an organic conductive compound is employed, it is possible to employ a wet film forming method such as a printing method or a coating method. When emitted light is taken out from the anode, the transmittance is preferably set to be 10% or more. A sheet resistance of the anode is preferably a few hundred Ω/□ or less.

Further, although a layer thickness of the anode depends on a material, it is generally selected in the range of 10 nm to 1 μm, and preferably in the range of 10 to 200 nm.

<<Cathode>>

As a cathode, a metal having a small work function (4 eV or less) (it is called as an electron injective metal), an alloy, a conductive compound and a mixture thereof are utilized as an electrode substance. Specific examples of the aforesaid electrode substance includes: sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, aluminum, and a rare earth metal. Among them, with respect to an electron injection property and durability against oxidation, preferable are: a mixture of election injecting metal with a second metal which is stable metal having a work function larger than the electron injecting metal. Examples thereof are: a magnesium/silver mixture, a magnesium/aluminum mixture, a magnesium/indium mixture, an aluminum/aluminum oxide ($Al_2O_3$) mixture, a lithium/aluminum mixture and aluminum.

A cathode may be made by using these electrode substances with a method such as a vapor deposition method or a sputtering method to form a thin film. A sheet resistance of the cathode is preferably a few hundred Ω/□ or less. A layer thickness of the cathode is generally selected in the range of 10 nm to 5 μm, and preferably in the range of 50 to 200 nm.

In order to transmit emitted light, it is preferable that one of an anode and a cathode of an organic EL element is transparent or translucent for achieving an improved luminescence.

Further, after forming a layer of the aforesaid metal having a thickness of 1 to 20 nm on the cathode, it is possible to prepare a transparent or translucent cathode by providing with a conductive transparent material described in the description for the anode thereon. By applying this process, it is possible to produce an element in which both an anode and a cathode are transparent.

<<Support Substrate>>

A support substrate which may be used for an organic EL element of the present invention is not specifically limited with respect to types such as glass and plastics. Hereafter, the support substrate may be also called as substrate body, substrate, substrate substance, or support. They may be transparent or opaque. However, a transparent support substrate is preferable when the emitting light is taken from the side of the support substrate. Support substrates preferably utilized includes such as glass, quartz and transparent resin film. A specifically preferable support substrate is a resin film capable of providing an organic EL element with a flexible property.

Examples of a resin film include: polyesters such as polyethylene terephthalate (PET) and polyethylene naphthalate (PEN), polyethylene, polypropylene, cellophane, cellulose esters and their derivatives such as cellulose diacetate, cellulose triacetate (TAC), cellulose acetate butyrate, cellulose acetate propionate (CAP), cellulose acetate phthalate, and cellulose nitrate, polyvinylidene chloride, polyvinyl alcohol, polyethylene vinyl alcohol, syndiotactic polystyrene, polycarbonate, norbornene resin, polymethyl pentene, polyether ketone, polyimide, polyether sulfone (PES), polyphenylene sulfide, polysulfones, polyether imide, polyether ketone imide, polyamide, fluororesin, Nylon, polymethyl methacrylate, acrylic resin, polyallylates and cycloolefin resins such as ARTON (trade name, made by JSR Co. Ltd.) and APEL (trade name, made by Mitsui Chemicals, Inc.).

On the surface of a resin film, it may be formed a film incorporating an inorganic or an organic compound or a hybrid film incorporating both compounds. Barrier films are preferred with a water vapor permeability of 0.01 g/($m^2$·24 h) or less (at 25±0.5° C. and 90±2% RH) determined based on JIS K 7129-1992. Further, high barrier films are preferred to have an oxygen permeability of $1\times10^{-3}$ ml/($m^2$·24 h·atm) or less determined based on JIS K 7126-1987, and a water vapor permeability of $1\times10^{-5}$ g/($m^2$·24 h) or less.

As materials that form a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited. Examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel films, opaque resin substrates, and ceramic substrates.

An external taking out quantum efficiency of light emitted by the organic EL element of the present invention is preferably 1% or more at a room temperature, but is more preferably 5% or more.

External taking out quantum efficiency (%)=(Number of photons emitted by the organic EL element to the exterior/Number of electrons fed to organic EL element)×100.

Further, it may be used simultaneously a color hue improving filter such as a color filter, or it may be used simultaneously a color conversion filter which convert emitted light color from the organic EL element to multicolor by employing fluorescent materials.

<<Sealing>>

As sealing means employed in the present invention, listed may be, for example, a method in which sealing members, electrodes, and a supporting substrate are subjected to adhesion via adhesives. The sealing members may be arranged to cover the display region of an organic EL element, and may be a concave plate or a flat plate. Neither transparency nor electrical insulation is limited.

Specifically listed are glass plates, polymer plate-films, metal plate-films. Specifically, it is possible to list, as glass plates, soda-lime glass, barium-strontium containing glass, lead glass, aluminosilicate glass, borosilicate glass, barium borosilicate glass, and quartz. Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to achieve a thin organic EL element, it is preferable to employ a polymer film or a metal film. Further, it is preferable that the polymer film has an oxygen permeability of $1\times10^{-3}$ ml/($m^2$·24 h·atm) or less determined by the method based on JIS K 7126-1987, and a water vapor permeability of $1\times10^{-3}$ g/($m^2$·24 h) or less (at 25±0.5° C., and 90±2% RH) determined by the method based on JIS K 7129-1992.

Conversion of the sealing member into concave is carried out by employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type UV curable epoxy resin adhesives.

In addition, since an organic EL element is occasionally deteriorated via a thermal process, preferred are those which enable adhesion and curing between a room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials that form the aforesaid film may be those which exhibit functions to retard penetration of moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

It is preferable to inject a gas phase and a liquid phase material of inert gases such as nitrogen or argon, and inactive liquids such as fluorinated hydrocarbon or silicone oil into the space between the space formed with the sealing member and the display region of the organic EL element. Further, it is possible to form vacuum in the space. Still further, it is possible to enclose hygroscopic compounds in the interior of the space.

Examples of a hygroscopic compound include: metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides. For sulfate salts, metal halides and perchlorates, suitably used are anhydrous salts.

<<Protective Film and Protective Plate>>

On the aforesaid sealing film which interposes the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, therefore it is preferable to arrange the protective film or the protective plate described above. Usable materials for these include glass plates, polymer plate-films, and metal plate-films which are similar to those employed for the aforesaid sealing. However, from the viewpoint of reducing weight and thickness, it is preferable to employ a polymer film.

<<Improving Method of Light Extraction>>

It is generally known that an organic EL element emits light in the interior of the layer exhibiting the refractive index (being about 1.6 to 2.1) which is greater than that of air, whereby only about 15% to 20% of light generated in the light emitting layer is extracted. This is due to the fact that light incident to an interface (being an interlace of a transparent substrate to air) at an angle of 6 which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example: a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between any layers of a substrate, and a transparent electrode layer and a light emitting layer (including between the substrate and the outside space).

By combining these means, the present invention enables the production of elements which exhibit higher luminance or excel in durability.

When a low refractive index medium having a thickness, greater than the wavelength of light is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5 to 1.7, the refractive index of the low refractive index layer is preferably approximately 1.5 or less. More preferably, it is 1.35 or less.

Further, thickness of the low refractive index medium is preferably at least two times of the wavelength in the medium. The reason is that, when the thickness of the low refractive index medium reaches nearly the wavelength of light so that electromagnetic waves escaped via evanescent enter into the substrate, effects of the low refractive index layer are lowered.

The method in which the interface which results in total reflection or a diffraction grating is introduced in any of the media is characterized in that light extraction efficiency is significantly enhanced. The above method works as follows. By utilizing properties of the diffraction grating capable of changing the light direction to the specific direction different from diffraction via so-called Bragg diffraction such as primary diffraction or secondary diffraction of the diffraction grating, of light emitted from the light entitling layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

A position to introduce a diffraction grating may be between any layers or in a medium (in a transparent substrate or a transparent electrode). However, a position near the organic light emitting layer, where light is generated, is preferable. In this case, the cycle of the diffraction grating is preferably from about ½ to 3 times of the wavelength of light in the medium. The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 to 100 μm. When it is less than the lower limit, coloration occurs due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, A shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

Applications

It is possible to employ the organic EL element of the present invention as display devices, displays, and various types of light emitting sources.

Examples of light emitting sources include: lighting apparatuses (home lighting and car lighting), clocks, backlights for liquid crystals, sign advertisements, signals, light sources of light memory media, light sources of electrophotographic copiers, light sources of light communication processors, and light sources of light sensors. The present invention is not limited to them. It is especially effectively employed as a backlight of a liquid crystal display device and a lighting source.

If needed, the organic EL element of the present, invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

<<Display Device>>

Hereafter, one example of a display device provided with an organic EL element of the present invention will be explained with reference to figures.

FIG. 1 is a schematic perspective drawing to show an example of a display device constituted of an organic EL element of the present invention. It displays image information by emission of an organic EL element. An example is a mobile phone.

As illustrated in FIG. 1, a display 1 is constituted of a display section A having plural number of pixels and a control section B which performs image scanning of the display section A based on image information.

The control section B, which is electrically connected to the display section A, sends a scanning signal and an image data signal to plural number of pixels based on image information from the outside and pixels of each scanning line successively emit depending on the image data signal by a scanning signal to perform image scanning, whereby image information is displayed on the display section A.

Figure 2:
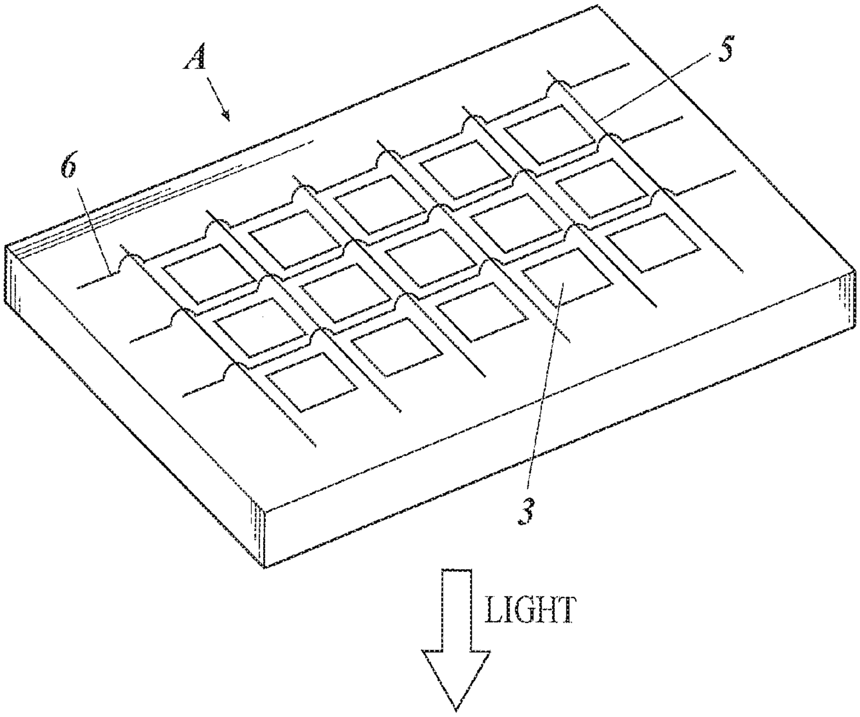
FIG. 2 is a schematic perspective drawing illustrating an example of a constitution of a display section A in FIG. 1

FIG. 2 is a schematic drawing of the display section A illustrated in FIG. 1.

The display section A is provided with a wiring part, which contains plural scanning lines 5 and data lines 6, and plural pixels 3 on a substrate.

Primary members of the display section A will be explained in the following.

In FIG. 2, it is illustrated the case that light emitted by a pixel 3 is taken out along a white arrow (downward). Scanning lines 5 and plural data lines 6 in a wiring part each are composed of a conductive material, and the scanning lines 5 and the data lines 6 are perpendicular in a grid form and are connected to the pixels 3 at the right-angled crossing points (details are not shown in the drawing).

The pixel 3 receives an image data from the data line 6 when a scanning signal is applied from the scanning line 5 and emits according to the received image data.

A full-color display device is achieved by appropriately arranging pixels each having an emission color in a red region, in a green region, and in a blue region, being placed side by side on the same substrate.

<<Lighting Device>>

It will be described one of the embodiments of a lighting device provided with an organic EL element of the present invention.

The non-light emitting surface of the organic EL element of the present invention was covered with a glass case, and a 300 μm thick glass substrate was employed as a sealing substrate. An epoxy based light curable type adhesive (LUXTRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIG. 3 and FIG. 4 was formed.

Figure 3:
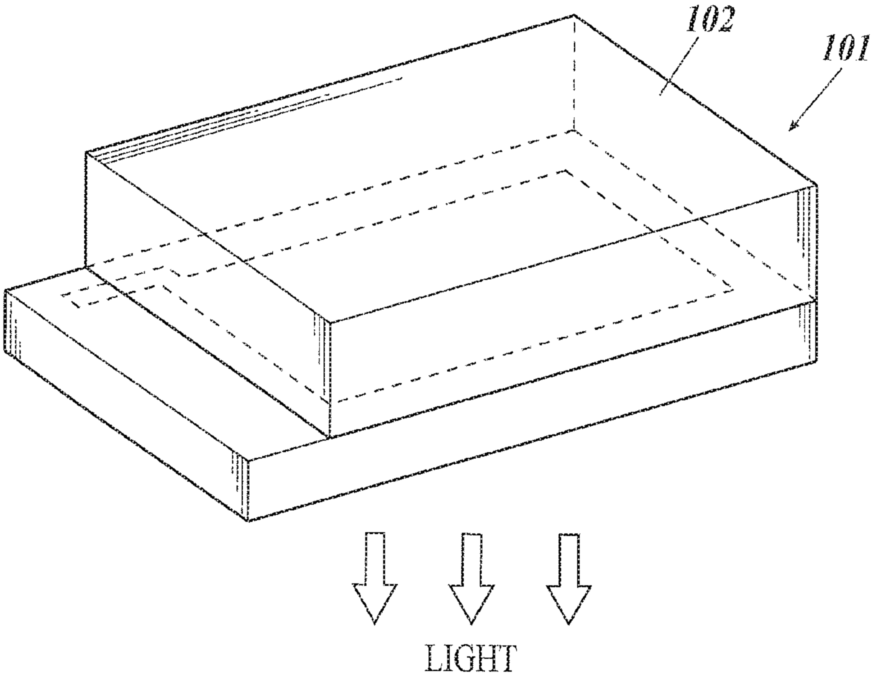
FIG. 3 is a schematic perspective drawing illustrating an example of a lighting device which uses an organic EL element of the present invention.

FIG. 3 is a schematic view of a lighting device. An organic EL element 101 of the present invention is covered with a glass cover 102 (incidentally, sealing by the glass cover was carried out in a globe box under nitrogen ambience (under air ambience of high purity nitrogen gas at a purity of at least 99.999%) so that the organic EL Element 101 was not brought into contact with atmosphere.

FIG. 4 is a cross-sectional view of a lighting device. In FIG. 4, 105 represents a cathode, 106 represents an organic EL layer, and 107 represents a glass substrate fitted with a transparent electrode. Further, the interior of glass cover 102 is filled with nitrogen gas 108 and a water catching agent 109 is provided.

EXAMPLES

Hereafter, the present invention will be described specifically by referring to examples, however, the present invention is not limited to them. In examples, the indication of “part” or “%” is used. Unless particularly mentioned, it represents “volume %”.

Compounds Used in Examples

Comparative compound 1

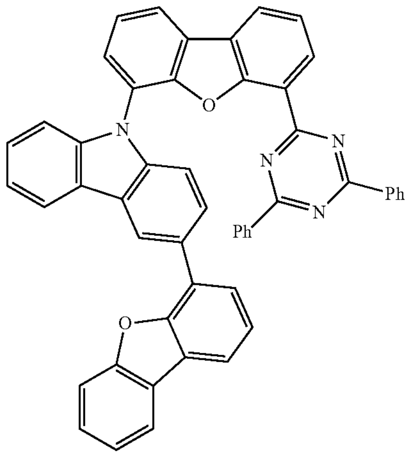

Comparative compound 2

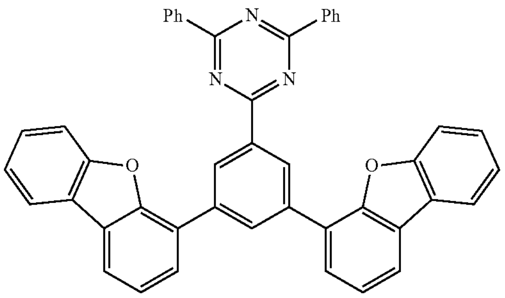

Comparative compound 3

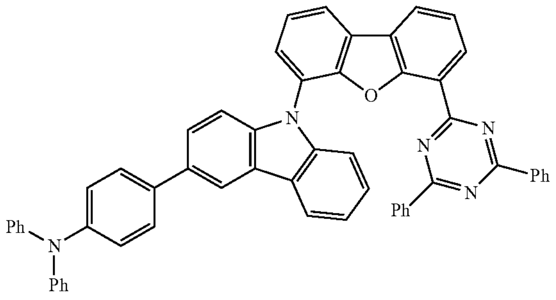

Comparative compound 4

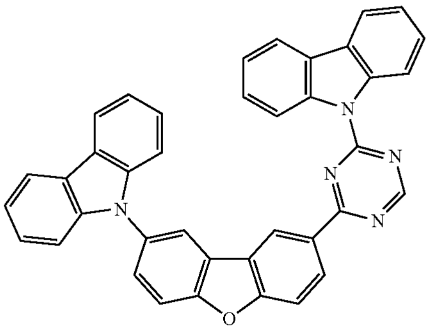

ET-1

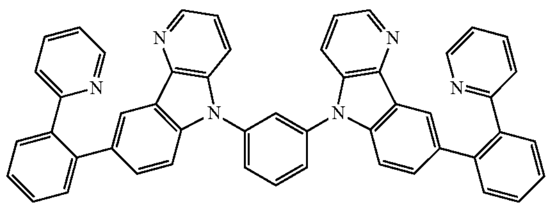

ET-2

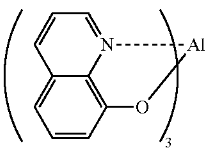

-continued
ET-3
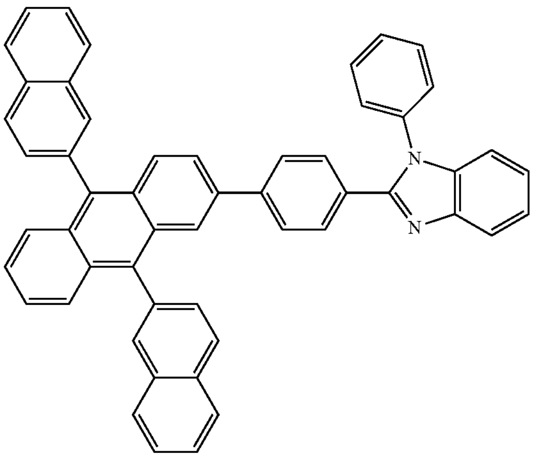
ET-4
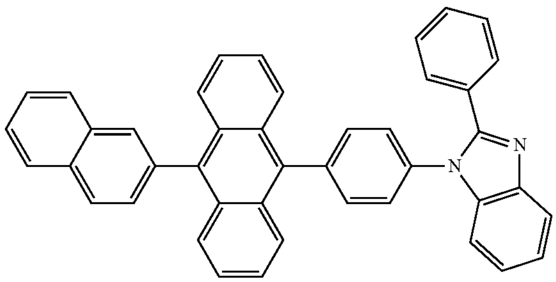
HI-1
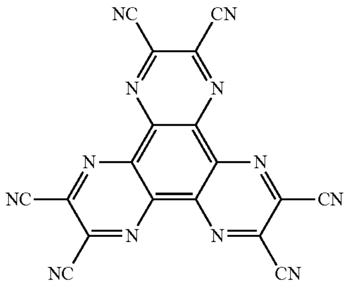
HI-2
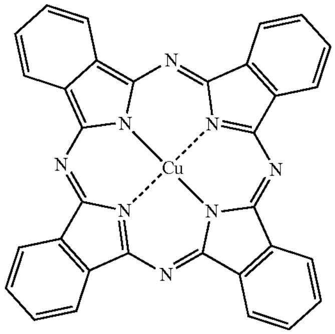
HB-1
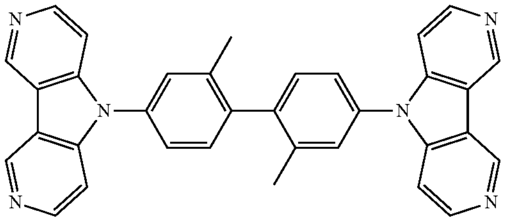
HB-2
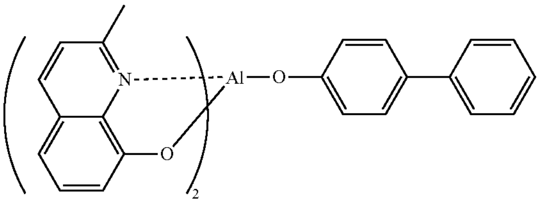
HB-3
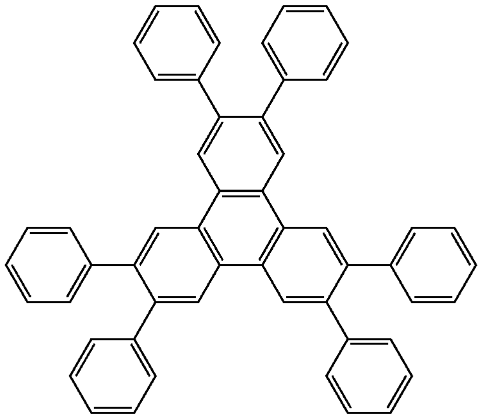
GD-1
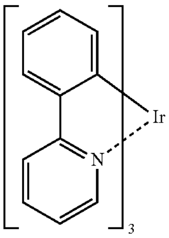

-continued
GD-2
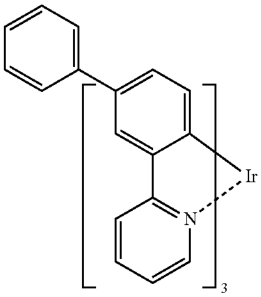
GD-3
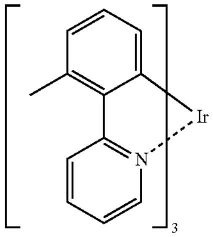
GD-4
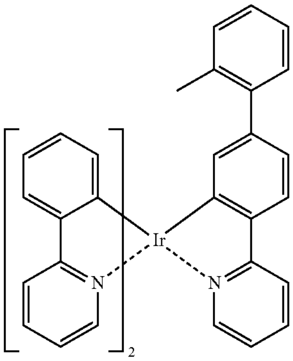
RD-1
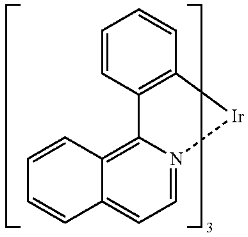
BD-1
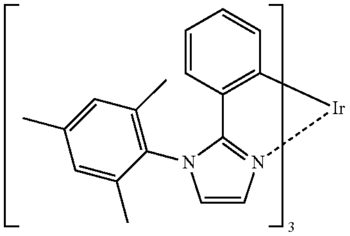
HT-1
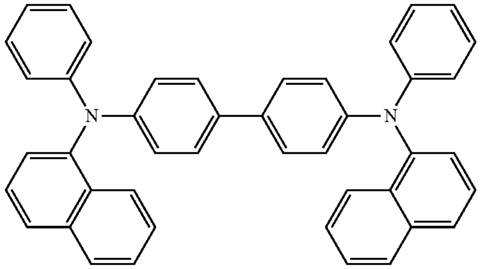
HT-2
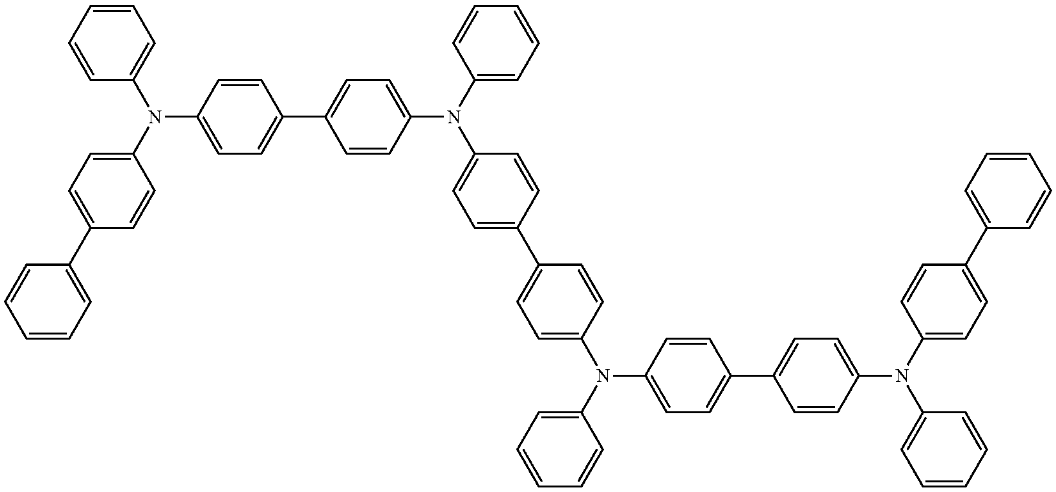

-continued

HT-3

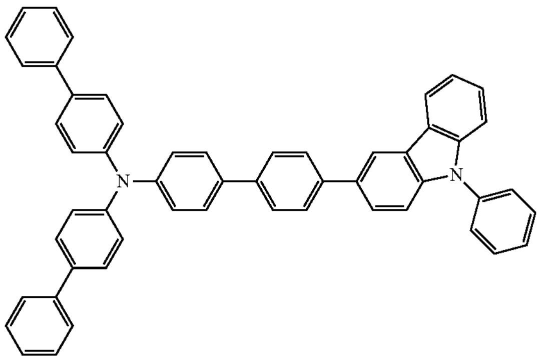

HT-4

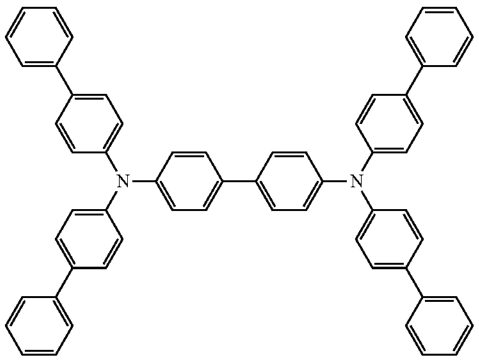

Example 1

<<Preparation of Organic EL Element>>

(1) Preparation of Organic EL Element 101

An anode was prepared by making patterning to a glass substrate of 50 mm×50 mm having a thickness of 0.7 mm on which ITO (indium tin oxide) was formed with a thickness of 150 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes. The resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-1 was heated via application of electric current and deposition was made onto the ITO transparent electrode at a deposition rate of 0.1 nm/second, whereby it was produced a hole injection layer having a thickness of 15 nm.

Subsequently, HT-1 was deposited onto the hole injection layer at a deposition rate of 0.1 nm/second, whereby it was produced a hole transport layer having a thickness of 30 nm.

Subsequently, the resistance heating boats each respectively containing the comparative compound 1 as a comparative host compound and GD-1 were heated via application of electric current and co-deposition was made onto the hole transport layer at a deposition rate of 0.1 nm/second and 0.010 nm/second, whereby it was produced a light emitting layer having a thickness of 40 nm.

Subsequently, HB-1 was deposited at a deposition rate of 0.1 nm/second, whereby it was produced a first electron transport layer having a thickness of 5 nm.

Further, ET-1 was deposited thereon at a deposition rate of 0.1 nm/second, whereby it was produced a second electron transport layer having a thickness of 45 nm.

Subsequently, 0.5 nm thick lithium fluoride was vapor deposited, and then, 100 nm thick aluminum was vapor deposited to form a cathode, whereby an organic EL element 101 was prepared.

After preparation of the organic EL element, the non-light emitting surface of the prepared organic EL element 101 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd,) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution illustrated in FIG. 3 and FIG. 4 was formed. This was used as a sample for evaluation.

<<Preparation of Organic EL Elements 102 to 111>>

Organic EL elements 102 to 111 were prepared in the same manner as preparation of the organic EL element 101 except that the host compound was changed as indicated in Table 1. After preparation, the lighting devices having the constitution as illustrated in FIG. 3 and FIG. 4 were prepared. They were used for samples.

<<Evaluation of Organic EL Elements 101 to 111>>

The prepared samples were subjected to the evaluations as described below. The evaluation results are listed in Table 1.

(1) External Taking Out Quantum Efficiency

Each organic EL element was allowed to emit light with a constant electric current of 2.5 mA/cm.sup.2 at room temperature (at about 23° C.). The external taking out quantum efficiency (η) was determined by measuring the luminance (L0) (cd/$m^2$) measured immediately after starting to emit light.

Here, the measurement of luminance was done with a spectroradiometer CS-2000 (produced by Konica Minolta Inc.). The external taking out quantum efficiency was represented by a relative value when the external quantum efficiency of the organic EL element 101 was set to be 100.

When the value is larger, it indicates that the light emitting efficiency is better.

(2) Half Lifetime

Evaluation of half Lifetime was done according to the following measuring method.

The prepared organic EL element was driven with a constant electric current to give an initial luminance of 4,000 cd/$m^2$.

The time required for decease in one half of the initial luminance was determined, and it was used as a scale for a half lifetime. The emission lifetime was represented as a relative value when the emission lifetime of the organic EL element 101 was set to be 100.

When the value is larger, it indicates that the durability is better compared with the comparative sample.

(3) Evaluation of High-Temperature Storage Stability

The prepared organic EL element was placed in a thermostat oven under a high-temperature condition (about 50±5° C.). The evaluation of half lifetime in the same manner as described in (2) was carried out. The heat resistance was calculated by using the following scheme.

Heat resistance (%)=[(Half lifetime under a high-temperature condition)/(Half lifetime at room temperature)]×100

In Table 1, the heat resistance was represented as a relative value when the heat resistance of the organic EL element 101 was set to be 100. When the heat resistance is larger, it indicates that the resistance against temperature change is better compared with the comparative sample. That is, the larger the heat resistance, the excellent the high-temperature storage stability.

Subsequently, HT-2 was deposited onto the hole injection layer at a deposition rate of 0.1 nm/second, whereby it was produced a hole transport layer having a thickness of 30 nm.

Subsequently, the resistance heating boats each respectively containing the comparative compound 2 as a comparative host compound and GD-2 were heated via application of electric current and co-deposition was made onto the hole transport layer at a deposition rate of 0.1 nm/second and 0.010 nm/second, whereby it was produced a light emitting layer having a thickness of 30 nm.

Subsequently, HB-2 was deposited at a deposition rate of 0.1 nm/second, whereby it was produced a first electron transport layer having a thickness of 5 nm.

Further. ET-2 was deposited thereon at a deposition rate of 0.1 nm/second, whereby it was produced a second electron transport layer having a thickness of 45 nm.

TABLE 1

| Organic EL element No. | Host compound | External taking out quantum efficiency (Relative value) | Half lifetime (Relative value) | High-temperature storage stability (Relative value) | Remarks |
|---|---|---|---|---|---|
| 101 | Comparative compound 1 | 100 | 100 | 100 | Comparative example |
| 102 | 1 | 106 | 135 | 133 | Present invention |
| 103 | 44 | 120 | 107 | 121 | Present invention |
| 104 | 262 | 110 | 147 | 108 | Present invention |
| 105 | 604 | 111 | 112 | 119 | Present invention |
| 106 | 221 | 132 | 195 | 201 | Present invention |
| 107 | 223 | 135 | 209 | 198 | Present invention |
| 108 | 232 | 146 | 208 | 189 | Present invention |
| 109 | 241 | 141 | 192 | 197 | Present invention |
| 110 | 251 | 141 | 207 | 204 | Present invention |
| 111 | 257 | 135 | 195 | 210 | Present invention |

From the results in Table 1, it is clear that the organic EL elements 102 to 111 of the present invention are excellent in external taking out quantum efficiency, half lifetime, and high-temperature storage stability compared with the comparative organic EL element 101.

Example 2

<<Preparation of Organic EL Element>>

(1) Preparation of Organic EL Element 201

An anode was prepared by making patterning to a glass substrate of 50 mm×50 mm having a thickness of 0.7 mm on which ITO (indium tin oxide) was formed with a thickness of 150 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes. The resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-2 was heated via application of electric current and deposition was made onto the ITO transparent electrode at a deposition rate of 0.1 nm/second, whereby it was produced a hole injection layer having a thickness of 10 nm.

Subsequently, 0.5 nm thick lithium fluoride was vapor deposited, and then, 100 nm thick aluminum was vapor deposited to form a cathode, whereby an organic EL element 201 was prepared.

After preparation of the organic EL element, the non-light emitting surface of the prepared organic EL element 201 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd,) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution as illustrated in FIG. 3 and FIG. 4 was formed. This was used as a sample for evaluation.

<<Preparation of Organic EL Elements 202 to 212>>

Organic EL elements 202 to 212 were prepared in the same manner as preparation of the organic EL element 201 except that the host compound was changed as indicated in Table 2. After preparation, the lighting devices having the constitution as illustrated in FIG. 3 and FIG. 4 were prepared. They were used for samples.

<<Evaluation of Organic EL Elements 201 to 212>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 201 were set to be 100.

The evaluation results are listed in Table 2.

TABLE 2

| Organic EL element No. | Host compound | External taking out quantum efficiency (Relative value) | Half lifetime (Relative value) | High-temperature storage stability (Relative value) | Remarks |
|---|---|---|---|---|---|
| 201 | Comparative compound 2 | 100 | 100 | 100 | Comparative example |
| 202 | 164 | 122 | 115 | 105 | Present invention |
| 203 | 366 | 103 | 107 | 129 | Present invention |
| 204 | 665 | 109 | 120 | 111 | Present invention |
| 205 | 797 | 112 | 122 | 109 | Present invention |
| 206 | 98 | 138 | 218 | 190 | Present invention |
| 207 | 102 | 140 | 210 | 201 | Present invention |
| 208 | 109 | 153 | 187 | 210 | Present invention |
| 209 | 116 | 154 | 200 | 188 | Present invention |
| 210 | 127 | 146 | 198 | 195 | Present invention |
| 211 | 130 | 149 | 200 | 185 | Present invention |
| 212 | 134 | 154 | 186 | 196 | Present invention |

From the results in Table 2, it is clear that the organic EL elements 202 to 212 of the present invention are excellent in external taking out quantum efficiency, half lifetime, and high-temperature storage stability compared with the comparative organic EL element 201.

Example 3

<<Preparation of Organic EL Element>>

(1) Preparation of Organic EL Element 301

An anode was prepared by making patterning to a glass substrate of 50 mm×50 mm having a thickness of 0.7 mm on which ITO (indium tin oxide) was formed with a thickness of 150 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes. The resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-2 was heated via application of electric current and deposition was made onto the ITO transparent electrode at a deposition rate of 0.1 nm/second, whereby it was produced a hole injection layer having a thickness of 20 nm.

Subsequently, HT-1 was deposited onto the hole injection layer at a deposition rate of 0.1 nm/second, whereby it was produced a hole transport layer having a thickness of 20 nm.

Subsequently, the resistance heating boats each respectively containing the comparative compound 3 as a comparative host compound and GD-3 were heated via application of electric current and co-deposition was made onto the hole transport layer at a deposition rate of 0.1 nm/second and 0.010 nm/second, whereby it was produced a light emitting layer having a thickness of 30 nm.

Subsequently, HB-3 was deposited at a deposition rate of 0.1 nm/second, whereby it was produced a first electron transport layer having a thickness of 10 nm.

Further, ET-2 was deposited thereon at a deposition rate of 0.1 nm/second, whereby it was produced a second electron transport layer having a thickness of 40 nm.

Subsequently, 0.5 nm thick lithium fluoride was vapor deposited, and then, 100 nm thick aluminum was vapor deposited to form a cathode, whereby an organic EL element 301 was prepared.

After preparation of the organic EL element, the non-light emitting surface of the prepared organic EL element 301 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd,) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution as illustrated in FIG. 3 and FIG. 4 was formed. This was used as a sample for evaluation.

<<Preparation of Organic EL Elements 302 to 312>>

Organic EL elements 302 to 312 were prepared in the same manner as preparation of the organic EL element 301 except that the host compound was changed as indicated in Table 3. After preparation, the lighting devices having the constitution as illustrated in FIG. 3 and FIG. 4 were prepared. They were used for samples.

<<Evaluation of Organic EL Elements 301 to 312>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 301 were set to be 100.

The evaluation results are listed in Table 3.

TABLE 3

| Organic EL element No. | Host compound | External taking out quantum efficiency (Relative value) | Half lifetime (Relative value) | High-temperature storage stability (Relative value) | Remarks |
|---|---|---|---|---|---|
| 301 | Comparative compound 3 | 100 | 100 | 100 | Comparative example |
| 302 | 90 | 101 | 150 | 106 | Present invention |
| 303 | 347 | 116 | 101 | 130 | Present invention |
| 304 | 451 | 107 | 115 | 111 | Present invention |
| 305 | 747 | 116 | 109 | 120 | Present invention |
| 306 | 179 | 142 | 201 | 196 | Present invention |
| 307 | 184 | 130 | 207 | 205 | Present invention |
| 308 | 187 | 131 | 230 | 199 | Present invention |
| 309 | 188 | 152 | 197 | 199 | Present invention |
| 310 | 198 | 139 | 207 | 204 | Present invention |
| 311 | 209 | 123 | 204 | 240 | Present invention |
| 312 | 212 | 148 | 199 | 201 | Present invention |

From the results in Table 3, it is clear that the organic EL elements 302 to 312 of the present invention are excellent in external taking out quantum efficiency, half lifetime, and high-temperature storage stability compared with the comparative organic EL element 301.

Example 4

<<Preparation of Organic EL Element>>

(1) Preparation of Organic EL Element 401

An anode was prepared by making patterning to a glass substrate of 50 mm×50 mm having a thickness of 0.7 mm on which ITO (indium tin oxide) was formed with a thickness of 120 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly (3,4-ethylenedioxythiophene)-polystyrene sulfonate (PEDOT/PSS, Baytron P A14083, made by Bayer AG) diluted with water by using a spin coating method at 3,000 rpm for 30 seconds to form a film, and then it was dried at 200° C. for one hour. A hole injection layer having a thickness of 20 nm was prepared.

Then, the resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-2 was heated via application of electric current and deposition was made onto the ITO transparent electrode at a deposition rate of 0.1 nm/second, whereby it was produced a hole transport layer having a thickness of 20 nm.

Subsequently, the resistance heating boats each respectively containing the comparative compound 4 as a comparative host compound and GD-1 were heated via application of electric current and co-deposition was made onto the hole transport layer at a deposition rate of 0.1 nm/second and 0.010 nm/second, whereby it was produced a light emitting layer having a thickness of 40 nm.

Subsequently, ET-1 was deposited at a deposition rate of 0.1 nm/second, whereby it was produced an electron transport layer having a thickness of 40 nm.

Subsequently, 0.5 nm thick lithium fluoride was vapor deposited, and then, 100 nm thick aluminum was vapor deposited to form a cathode, whereby an organic EL element 401 was prepared.

After preparation of the organic EL element, the non-light emitting surface of the prepared organic EL element 401 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution as illustrated in FIG. 3 and FIG. 4 was formed. This was used as a sample for evaluation.

<<Preparation of Organic EL Elements 402 to 412>>

Organic EL elements 402 to 412 were prepared in the same manner as preparation of the organic EL element 401 except that the host compound was changed as indicated in Table 4. After preparation, the lighting devices having the constitution as illustrated in FIG. 3 and FIG. 4 were prepared. They were used for samples.

<<Evaluation of Organic EL Elements 401 to 412>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 401 were set to be 100.

The evaluation results are listed in Table 4.

TABLE 4

| Organic EL element No. | Host compound | External taking out quantum efficiency (Relative value) | Half lifetime (Relative value) | High-temperature storage stability (Relative value) | Remarks |
|---|---|---|---|---|---|
| 401 | Comparative compound 4 | 100 | 100 | 100 | Comparative example |
| 402 | 148 | 103 | 110 | 120 | Present invention |
| 403 | 288 | 126 | 110 | 107 | Present invention |
| 404 | 565 | 115 | 122 | 104 | Present invention |
| 405 | 724 | 105 | 114 | 121 | Present invention |
| 406 | 52 | 144 | 192 | 190 | Present invention |
| 407 | 54 | 143 | 200 | 240 | Present invention |
| 408 | 56 | 155 | 209 | 208 | Present invention |
| 409 | 60 | 153 | 212 | 196 | Present invention |
| 410 | 73 | 150 | 209 | 207 | Present invention |
| 411 | 78 | 144 | 190 | 187 | Present invention |
| 412 | 84 | 135 | 237 | 211 | Present invention |

From the results in Table 4, it is clear that the organic EL elements 402 to 412 of the present invention are excellent in external taking out quantum efficiency, half lifetime, and high-temperature storage stability compared with the comparative organic EL element 401.

Example 5

<<Preparation of Organic EL Element>>

(1) Preparation of Organic EL Element 501

An anode was prepared by making patterning to a glass substrate of 50 mm×50 mm having a thickness of 0.7 mm on which ITO (indium tin oxide) was formed with a thickness of 120 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly (3,4-ethylenedioxythiophene)-polystyrene sulfonate (PEDOT/PSS, Baytron P AI4083, made by Bayer AG) diluted with water by using a spin coating method at 3,000 rpm for 30 seconds to form a film, and then it was dried at 200° C. for one hour. A hole injection layer having a thickness of 20 nm was prepared.

Then, the resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-4 was heated via application of electric current and deposition was made onto the ITO transparent electrode at a deposition rate of 0.1 nm/second, whereby it was produced a hole transport layer having a thickness of 20 nm.

Subsequently, the resistance heating boats each respectively containing the comparative compound 1 as a comparative host compound and GD-1 were heated via application of electric current and co-deposition was made onto the hole transport layer at a deposition rate of 0.1 nm/second and 0.010 nm/second, whereby it was produced a light emitting layer having a thickness of 40 nm.

Subsequently, HB-1 was deposited at a deposition rate of 0.1 nm/second, whereby it was produced a first electron transport layer having a thickness of 5 nm.

Further. ET-3 was deposited thereon at a deposition rate of 0.1 nm/second, whereby it was produced a second electron transport layer having a thickness of 30 nm.

Subsequently, 0.5 nm thick lithium fluoride was vapor deposited, and then, 100 nm thick aluminum was vapor deposited to form a cathode, whereby an organic EL element 501 was prepared.

After preparation of the organic EL element, the non-light emitting surface of the prepared organic EL element 501 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution as illustrated in FIG. 3 and FIG. 4 was formed. This was used as a sample for evaluation.

<<Preparation of Organic EL Elements 502 to 512>>

Organic EL elements 502 to 512 were prepared in the same manner as preparation of the organic EL element 501 except that the host compound was changed as indicated in Table 5. After preparation, the lighting devices having the constitution as illustrated in FIG. 3 and FIG. 4 were prepared. They were used for samples.

<<Evaluation of Organic EL Elements 501 to 512>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 501 were set to be 100.

The evaluation results are listed in Table 5.

TABLE 5

| Organic EL element No. | Host compound | External taking out quantum efficiency (Relative value) | Half lifetime (Relative value) | High-temperature storage stability (Relative value) | Remarks |
|---|---|---|---|---|---|
| 501 | Comparative compound 1 | 100 | 100 | 100 | Comparative example |
| 502 | 16 | 125 | 104 | 110 | Present invention |
| 503 | 151 | 118 | 129 | 119 | Present invention |
| 504 | 430 | 115 | 103 | 126 | Present invention |
| 505 | 740 | 112 | 116 | 120 | Present invention |
| 506 | 610 | 153 | 199 | 241 | Present invention |
| 507 | 613 | 161 | 245 | 190 | Present invention |
| 508 | 619 | 150 | 238 | 229 | Present invention |
| 509 | 629 | 134 | 192 | 185 | Present invention |
| 510 | 634 | 145 | 253 | 201 | Present invention |
| 511 | 639 | 165 | 199 | 267 | Present invention |
| 512 | 642 | 139 | 228 | 257 | Present invention |

From the results in Table 5, it is clear that the organic EL elements 502 to 512 of the present invention are excellent in external taking out quantum efficiency, half lifetime, and high-temperature storage stability compared with the comparative organic EL element 501.

Example 6

<<Preparation of Organic EL Element>>

(1) Preparation of Organic EL Element 601

An anode was prepared by making patterning to a glass substrate of 50 mm×50 mm having a thickness of 0.7 mm on which ITO (indium tin oxide) was formed with a thickness of 150 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes. The resulting transparent support substrate was fixed to a substrate holder of a commercial vacuum deposition apparatus.

The constituting materials for each layer were loaded in each resistance heating boat for vapor deposition in the vacuum deposition apparatus with an optimum amount. As a resistance heating boat for vapor deposition, it was used a resistance heating boat made of molybdenum or tungsten.

After reducing the pressure of a vacuum tank to $4\times10^{-4}$ Pa, the resistance heating boat containing HI-1 was heated via application of electric current and deposition was made onto the ITO transparent electrode at a deposition rate of 0.1 nm/second, whereby it was produced a hole injection layer having a thickness of 15 nm.

Subsequently, HT-3 was deposited onto the hole injection layer at a deposition rate of 0.1 nm/second, whereby it was produced a hole transport layer having a thickness of 30 nm.

Subsequently, the resistance heating boats each respectively containing the comparative compound 2 as a comparative host compound and GD-2 were heated via application of electric current and co-deposition was made onto the hole transport layer at a deposition rate of 0.1 nm/second and 0.010 nm/second, whereby it was produced a light emitting layer having a thickness of 40 nm.

Subsequently, ET-2 was deposited thereon at a deposition rate of 0.1 nm/second, whereby it was produced a second electron transport layer having a thickness of 40 nm.

Further, 0.5 nm thick lithium fluoride was vapor deposited thereon, and then, 100 nm thick aluminum was vapor deposited to form a cathode, whereby an organic EL element 601 was prepared.

After preparation of the organic EL element, the non-light emitting surface of the prepared organic EL element 601 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd,) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution illustrated in FIG. 3 and FIG. 4 was formed. This was used as a sample for evaluation.

<<Preparation of Organic EL Elements 602 to 611>>

Organic EL elements 602 to 611 were prepared in the same manner as preparation of the organic EL element 601 except that the host compound was changed as indicated in Table 6. After preparation, the lighting devices having the constitution as illustrated in FIG. 3 and FIG. 4 were prepared. They were used for samples.

<<Evaluation of Organic EL Elements 601 to 611>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 601 were set to be 100.

The evaluation results are listed in Table 6.

TABLE 6

| Organic EL element No. | Host compound | External taking out quantum efficiency (Relative value) | Half lifetime (Relative value) | High-temperature storage stability (Relative value) | Remarks |
|---|---|---|---|---|---|
| 601 | Comparative compound 2 | 100 | 100 | 100 | Comparative example |
| 602 | 33 | 115 | 108 | 105 | Present invention |
| 603 | 428 | 104 | 130 | 110 | Present invention |
| 604 | 551 | 124 | 110 | 113 | Present invention |
| 605 | 680 | 107 | 135 | 103 | Present invention |
| 606 | 496 | 151 | 230 | 209 | Present invention |
| 607 | 499 | 163 | 196 | 234 | Present invention |
| 608 | 503 | 161 | 201 | 206 | Present invention |
| 609 | 505 | 144 | 237 | 198 | Present invention |
| 610 | 516 | 149 | 213 | 222 | Present invention |
| 611 | 523 | 134 | 192 | 196 | Present invention |

From the results in Table 6, it is clear that the organic EL elements 602 to 611 of the present invention are excellent in external taking out quantum efficiency, half lifetime, and high-temperature storage stability compared with the comparative organic EL element 601.

Example 7

<<Preparation of Organic EL Element>>

(1) Preparation of Organic EL Element 701

An organic EL element 701 was prepared in the same manner as preparation of the organic EL element 601 except for the following changes: HT-3 was replaced with HT-2; the comparative compound 2 was replaced with the comparative compound 3; GD-2 was replaced with GD-4; and ET-2 was replaced with ET-3. After preparation of the organic EL element, the lighting device having the constitution illustrated in FIG. 3 and FIG. 4 was formed. This was used as a sample for evaluation.

<<Preparation of Organic EL elements 702 to 711>>

Organic EL elements 702 to 711 were prepared in the same manner as preparation of the organic EL element 701 except that the host compound was changed as indicated in Table 7. After preparation, the lighting devices having the constitution as illustrated in FIG. 3 and FIG. 4 were prepared. They were used for samples.

<<Evaluation of Organic EL elements 701 to 711>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 701 were set to be 100.

The evaluation results are listed in Table 7.

TABLE 7

| Organic EL element No. | Host compound | External taking out quantum efficiency (Relative value) | Half lifetime (Relative value) | High-temperature storage stability (Relative value) | Remarks |
|---|---|---|---|---|---|
| 701 | Comparative compound 3 | 100 | 100 | 100 | Comparative example |
| 702 | 174 | 120 | 110 | 120 | Present invention |
| 703 | 352 | 103 | 128 | 117 | Present invention |
| 704 | 544 | 124 | 104 | 120 | Present invention |
| 705 | 733 | 116 | 124 | 103 | Present invention |
| 706 | 571 | 157 | 207 | 199 | Present invention |
| 707 | 575 | 150 | 200 | 213 | Present invention |
| 708 | 578 | 138 | 230 | 212 | Present invention |
| 709 | 583 | 137 | 200 | 223 | Present invention |
| 710 | 593 | 141 | 235 | 192 | Present invention |
| 711 | 599 | 150 | 206 | 201 | Present invention |

From the results in Table 7, it is clear that the organic EL elements 702 to 711 of the present invention are excellent in external taking out quantum efficiency, half lifetime, and high-temperature storage stability compared with the comparative organic EL element 701.

Example 8

<<Preparation of Organic EL Element>>

(1) Preparation of Organic EL Element 801

An organic EL element 801 was prepared in the same manner as preparation of the organic EL element 201 described in Example 2 except for the following changes: HT-2 was replaced with HT-3; the comparative compound 2 was replaced with the comparative compound 4; GD-2 was replaced with GD-3; HB-2 was replaced with HB-3; and ET-2 was replaced with ET-3. After preparation of the organic EL element, the lighting device having the constitution illustrated in FIG. 3 and FIG. 4 was formed as in Example 1. This was used as a sample for evaluation.

<<Preparation of Organic EL Elements 802 to 811>>

Organic EL elements 802 to 811 were prepared in the same manner as preparation of the organic EL element 801 except that the host compound was changed as indicated in Table 8. After preparation, the lighting devices having the constitution as illustrated in FIG. 3 and FIG. 4 were prepared. They were used for samples.

<<Evaluation of Organic EL Elements 801 to 811>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 801 were set to be 100.

The evaluation results are listed in Table 8.

TABLE 8

| Organic EL element No. | Host compound | External taking out quantum efficiency (Relative value) | Half lifetime (Relative value) | High-temperature storage stability (Relative value) | Remarks |
|---|---|---|---|---|---|
| 801 | Comparative compound 4 | 100 | 100 | 100 | Comparative example |
| 802 | 22 | 126 | 108 | 105 | Present invention |
| 803 | 215 | 127 | 101 | 138 | Present invention |
| 804 | 409 | 109 | 109 | 133 | Present invention |
| 805 | 673 | 117 | 130 | 103 | Present invention |
| 806 | 453 | 149 | 209 | 223 | Present invention |
| 807 | 457 | 163 | 212 | 189 | Present invention |
| 808 | 464 | 155 | 200 | 207 | Present invention |
| 809 | 467 | 140 | 182 | 191 | Present invention |
| 810 | 474 | 136 | 195 | 192 | Present invention |
| 811 | 484 | 161 | 209 | 200 | Present invention |

From the results in Table 8, it is clear that the organic EL elements 802 to 811 of the present invention are excellent in external taking out quantum efficiency, half lifetime, and high-temperature storage stability compared with the comparative organic EL element 801.

Example 91

<<Preparation of Organic EL Element>>

(1) Preparation of Organic EL Element 901

An organic EL element 901 was prepared in the same manner as preparation of the organic EL element 201 described in Example 2 except for the following changes: HT-2 was replaced with HT-4; the comparative compound 2 was replaced with the comparative compound 1; GD-2 was replaced with GD-4; HB-2 was replaced with HB-3; and ET-2 was replaced with ET-4. After preparation of the organic EL element, the lighting device having the constitution illustrated in FIG. 3 and FIG. 4 was formed as in Example 1. This was used as a sample for evaluation.

<<Preparation of Organic EL Elements 902 to 911>>

Organic EL elements 902 to 911 were prepared in the same manner as preparation of the organic EL element 901 except that the host compound was changed as indicated in Table 9. After preparation, the lighting devices having the constitution as illustrated in FIG. 3 and FIG. 4 were prepared. They were used for samples.

<<Evaluation of Organic EL Elements 901 to 911>>

The prepared samples were subjected to the evaluations as described below.

With respect to external taking out quantum efficiency, half lifetime, and evaluation of high-temperature storage stability evaluations were made in the same ways as in Example 1. The evaluation results were represented as a relative value when the results of the organic EL element 901 were set to be 100.

The evaluation results are listed in Table 9.

TABLE 9

| Organic EL element No. | Host compound | External taking out quantum efficiency (Relative value) | Half lifetime (Relative value) | High-temperature storage stability (Relative value) | Remarks |
|---|---|---|---|---|---|
| 901 | Comparative compound 1 | 100 | 100 | 100 | Comparative example |
| 902 | 140 | 123 | 108 | 119 | Present invention |
| 903 | 341 | 120 | 133 | 101 | Present invention |
| 904 | 486 | 117 | 124 | 110 | Present invention |
| 905 | 541 | 114 | 130 | 103 | Present invention |
| 906 | 304 | 152 | 201 | 210 | Present invention |
| 907 | 307 | 148 | 233 | 198 | Present invention |
| 908 | 310 | 156 | 220 | 198 | Present invention |
| 909 | 326 | 133 | 200 | 210 | Present invention |
| 910 | 331 | 142 | 203 | 204 | Present invention |
| 911 | 335 | 146 | 206 | 206 | Present invention |

From the results in Table 9, it is clear that the organic EL elements 902 to 911 of the present invention are excellent in external taking out quantum efficiency, half lifetime, and high-temperature storage stability compared with the comparative organic EL element 901.

Example 10

<<Preparation of Organic EL Element>>

(1) Preparation of Organic EL Element 1001

An organic EL element 1001 was prepared in the same manner as preparation of the organic EL element 401 described in Example 4 except for the following changes: HT-2 was replaced with HT-3; the comparative compound 4 was replaced with the comparative compound 2; and ET-1 was replaced with ET-4. After preparation of the organic EL element, the lighting device having the constitution illustrated in FIG. 3 and FIG. 4 was formed as in Example 1. This was used as a sample for evaluation.

<<Preparation of Organic EL Elements 1002 to 1013>>

Organic EL elements 1002 to 1013 were prepared in the same manner as preparation of the organic EL element 1001 except that the host compound was changed as indicated in Table 10. After preparation, the lighting devices having the constitution as illustrated in FIG. 3 and FIG. 4 were prepared. They were used for samples.

<<Evaluation of Organic EL Elements 1001 to 1013>>

The prepared samples were subjected to the evaluations as described below.

With respect to external taking out quantum efficiency half lifetime, and evaluation of high-temperature storage stability, evaluations were made in the same ways as in Example 1. The evaluation results were represented as a relative value when the results of the organic EL element 1001 were set to be 100.

The evaluation results are listed in Table 10.

TABLE 10

| Organic EL element No. | Host compound | External taking out quantum efficiency (Relative value) | Half lifetime (Relative value) | High-temperature storage stability (Relative value) | Remarks |
|---|---|---|---|---|---|
| 1001 | Comparative compound 2 | 100 | 100 | 100 | Comparative example |
| 1002 | 152 | 118 | 122 | 126 | Present invention |
| 1003 | 268 | 103 | 124 | 122 | Present invention |
| 1004 | 297 | 106 | 120 | 124 | Present invention |
| 1005 | 533 | 120 | 140 | 101 | Present invention |
| 1006 | 369 | 149 | 211 | 218 | Present invention |
| 1007 | 371 | 127 | 188 | 175 | Present invention |
| 1008 | 379 | 131 | 245 | 201 | Present invention |
| 1009 | 383 | 139 | 180 | 187 | Present invention |
| 1010 | 388 | 146 | 199 | 200 | Present invention |
| 1011 | 398 | 153 | 234 | 204 | Present invention |
| 1012 | 402 | 151 | 208 | 226 | Present invention |
| 1013 | 404 | 140 | 201 | 203 | Present invention |

From the results in Table 10, it is clear that the organic EL elements 1002 to 1013 of the present invention are excellent in external taking out quantum efficiency; half lifetime, and high-temperature storage stability compared with the comparative organic EL element 1001.

Example 11

<<Preparation of Organic EL Element>>

(1) Preparation of Organic EL Element 1101

An organic EL element 1101 was prepared in the same manner as preparation of the organic EL element 501 described in Example 5 except for the following changes: HT-4 was replaced with HT-1; the comparative compound was replaced with the comparative compound 3; GD-1 was replaced with GD-4; and ET-3 was replaced with ET-2. After preparation of the organic EL element, the lighting device having the constitution illustrated in FIG. 3 and FIG. 4 was formed as in Example 1. This was used as a sample for evaluation.

<<Preparation of Organic EL Elements 1102 to 1112>>

Organic EL elements 1102 to 1112 were prepared in the same manner as preparation of the organic EL element 1101 except that the host compound was changed as indicated in Table 11. After preparation, the lighting devices having the constitution as illustrated in FIG. 3 and FIG. 4 were prepared. They were used for samples.

<<Evaluation of Organic EL Elements 1101 to 1112>>

The prepared samples were subjected to the evaluations as described below.

With respect to external taking out quantum efficiency half lifetime, and evaluation of high-temperature storage stability, evaluations were made in the same ways as in Example 1. The evaluation results were represented as a relative value when the results of the organic EL element 1101 were set to be 100.

The evaluation results are listed in Table 11.

TABLE 11

| Organic EL element No. | Host compound | External taking out quantum efficiency (Relative value) | Half lifetime (Relative value) | High-temperature storage stability (Relative value) | Remarks |
|---|---|---|---|---|---|
| 1101 | Comparative compound 3 | 100 | 100 | 100 | Comparative example |
| 1102 | 40 | 118 | 113 | 101 | Present invention |
| 1103 | 282 | 113 | 118 | 117 | Present invention |
| 1104 | 416 | 120 | 114 | 120 | Present invention |
| 1105 | 645 | 111 | 120 | 107 | Present invention |
| 1106 | 685 | 141 | 226 | 218 | Present invention |
| 1107 | 689 | 151 | 208 | 213 | Present invention |
| 1108 | 696 | 150 | 218 | 210 | Present invention |
| 1109 | 700 | 133 | 188 | 181 | Present invention |
| 1110 | 705 | 153 | 211 | 205 | Present invention |
| 1111 | 709 | 146 | 222 | 212 | Present invention |
| 1112 | 719 | 141 | 209 | 218 | Present invention |

From the results in Table 11, it is clear that the organic EL elements 1102 to 1112 of the present invention are excellent in external taking out quantum efficiency, half lifetime, and high-temperature storage stability compared with the comparative organic EL element 1101.

Example 12

<<Preparation of Organic EL Element>>

(1) Preparation of Organic EL Element 1201

An organic EL element 1201 was prepared in the same manner as preparation of the organic EL element 101 described in Example 1 except for the following changes: HT-1 was replaced with HT-4; the comparative compound 1 was replaced with the comparative compound 4; GD-1 was replaced with GD-3; HB-1 was replaced with HB-2; and ET-1 was replaced with ET-3. After preparation of the organic EL element, the lighting device having the constitution illustrated in FIG. 3 and FIG. 4 was formed as in Example 1. This was used as a sample for evaluation.

<<Preparation of Organic EL Elements 1202 to 1214>>

Organic EL elements 1202 to 1214 were prepared in the same manner as preparation of the organic EL element 1201 except that the host compound was changed as indicated in Table 12. After preparation, the lighting devices having the constitution as illustrated in FIG. 3 and FIG. 4 were prepared. They were used for samples.

<<Evaluation of Organic EL Elements 1201 to 1214>>

The prepared samples were subjected to the evaluations as described below.

With respect to external taking out quantum efficiency, half lifetime, and evaluation of high-temperature storage stability, evaluations were made in the same ways as in Example 1. The evaluation results were represented as a relative value when the results of the organic EL element 1201 were set to be 100.

The evaluation results are listed in Table 12.

TABLE 12

| Organic EL element No. | Host compound | External taking out quantum efficiency (Relative value) | Half lifetime (Relative value) | High-temperature storage stability (Relative value) | Remarks |
|---|---|---|---|---|---|
| 1201 | Comparative compound 4 | 100 | 100 | 100 | Comparative example |
| 1202 | 168 | 120 | 106 | 120 | Present invention |
| 1203 | 274 | 103 | 128 | 117 | Present invention |
| 1204 | 421 | 118 | 104 | 120 | Present invention |
| 1205 | 658 | 113 | 124 | 103 | Present invention |
| 1206 | 755 | 139 | 236 | 208 | Present invention |
| 1207 | 759 | 151 | 208 | 214 | Present invention |
| 1208 | 765 | 155 | 227 | 200 | Present invention |
| 1209 | 768 | 128 | 194 | 185 | Present invention |
| 1210 | 773 | 138 | 191 | 175 | Present invention |
| 1211 | 784 | 146 | 226 | 209 | Present invention |
| 1212 | 788 | 143 | 208 | 220 | Present invention |
| 1213 | 802 | 151 | 209 | 206 | Present invention |
| 1214 | 801 | 147 | 214 | 209 | Present invention |

From the results in Table 12, it is clear that the organic EL elements 1202 to 1214 of the present invention are excellent in external taking out quantum efficiency, half lifetime, and high-temperature storage stability compared with the comparative organic EL element 1101.

Example 13

<<Preparation of Full-Color Display Device>>

(1) Blue Color Emitting Element

<<Preparation of Organic EL Element 1301>>

An anode was prepared by making patterning to a glass substrate of 100 mm×100 mm×1.1 mm (NA45, produced by NH Techno Glass Corp.) on which ITO (indium tin oxide) was formed with a thickness of 100 nm. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

The resulting transparent support substrate was fixed to a substrate holder of a commercial vacuum deposition apparatus. Separately, 200 mg of HT-1 was placed in a molybdenum resistance heating boat, 200 mg of mCP (1,3-bis-N-carbazolylbenzene) as a host compound was placed in another molybdenum resistance heating boat, 200 mg of HB-2 was placed in another molybdenum resistance heating boat, 100 mg of BD-1 as a light emitting dopant was placed in another molybdenum resistance heating boat, and 200 mg of ET-2 was placed in another molybdenum resistance heating boat. The resulting boats were fitted in the vacuum deposition apparatus.

Subsequently, after reducing the pressure of a vacuum tank to $4\times10^{-4}$ Pa, the heating boat containing HT-1 was heated via application of electric current and deposition was made onto the transparent support substrate at a deposition rate of 0.1 nm/second, whereby it was produced a hole transport layer having a thickness of 40 nm.

Subsequently, the molybdenum resistance heating boats each respectively containing mCP (1,3-bis-N-carbazolylbenzene) and BD-1 were heated via application of electric current and co-deposition was made onto the hole transport layer at a deposition rate of 0.2 nm/second and 0.012 nm/second, whereby it was produced a light emitting layer having a thickness of 40 nm. The substrate temperature was made to be room temperature during the deposition process.

Further, the molybdenum resistance heating boat containing HB-2 was heated via application of electric current, and deposition was made onto the light emitting layer at a deposition rate of 0.1 nm/second, whereby it was produced a hole blocking layer having a thickness of 10 nm.

Further, the molybdenum resistance heating boat containing ET-2 was heated via application of electric current, and deposition was made onto the hole blocking layer at a deposition rate of 0.1 nm/second, whereby it was produced an electron transport layer having a thickness of 10 nm. The substrate temperature was made to be room temperature during the deposition process.

Subsequently, 0.5 nm thick lithium fluoride was vapor deposited, and then, 110 nm thick aluminum was vapor deposited to form a cathode, whereby an organic EL element 1301 was prepared.

After preparation of the organic EL element, the non-light emitting surface of the prepared organic EL element 1301 was covered with a glass cover under the atmosphere of high purity nitrogen gas of 99.999% or more. A glass substrate having a thickness of 300 μm was used as a sealing substrate. As a sealing material, an epoxy-based light curable adhesive (LUXTRACK LC0629B produced by Toagosei Co., Ltd,) was applied to the periphery of the glass cover. The resulting one was superimposed on the cathode side to be brought into close contact with the transparent support substrate. Curing and sealing were carried out via exposure of UV radiation onto the glass substrate side, whereby the lighting device having the constitution as illustrated in FIG. 3 and FIG. 4 was formed. This was used as a sample for evaluation.

(2) Green Color Emitting Element

The organic EL element in Example 5 was used as a green color emitting element.

(3) Red Color Emitting Element

<<Preparation of Organic EL Element 1302>>

An organic EL element 1302 that is a red color emitting element was prepared in the same manner as preparation of the organic EL element 1301 that is a blue color emitting element except that the light emitting dopant GD-1 was replaced with RD-1.

(4) Preparation of Display Device

The red color, green color and blue color emitting organic EL elements were arranged in a line on the same substrate. It was prepared a full-color display device with an active matrix mode and having the structure as illustrated in FIG. 1.

FIG. 2 is a schematic drawing illustrating only a display section A of the prepared display device.

As illustrated in FIG. 2, the display section A has: a wiring section containing plural scanning lines 5 and data lines 6, and plural pixels 3 (such as a pixel having an emission color of a red region, a pixel of a green region and a pixel of a blue region) arranged in parallel provided on the same substrate. The scanning lines 5 and data lines 6 in the wiring section, which are respectively composed of a conductive material, cross each other at a right angle in a grid form and are connected to the pixels 3 at the right-angled crossing points (details are not shown in the drawing).

The plural pixels 3 each are operated in an active matrix mode provided with a switching transistor and an operating transistor, both being an active element, and organic EL elements corresponding to each emission color. The plural pixels 3 receive an image data signal from the date line 6 when a scanning signal is applied from the scanning line 5 to emit based on the received image data. Each red, green and blue pixel 3 was suitably arranged in parallel in this manner, whereby a full-color display device was prepared.

It has been confirmed that the obtained full-color display device exhibited a full-color moving image having a high luminance, a high durability, and excellent in storage stability at high-temperature when it was driven.

INDUSTRIAL APPLICABILITY

An organic electroluminescent element of the present invention uses a novel aromatic heterocyclic derivative. This organic electroluminescent element is characterized in exhibiting high emission efficiency, long emission lifetime, and small change after usage at high-temperature. It is suitably used for a display device and a lighting device.

DESCRIPTION OF SYMBOLS

1: Display
3: Pixel
5: Scanning line
6: Data line
A: Display section
B: Control section
101: Organic EL element
102: Glass cover
105: Cathode
106: Organic EL layer
107: Glass substrate having a transparent electrode
108: Nitrogen gas
109: Water catching agent

The invention claimed is:

1. An organic electroluminescent element comprising a light emitting layer comprising an aromatic heterocyclic derivative having a structure represented by Formula (H2), wherein the aromatic heterocyclic derivative is contained in the light emitting layer as a host compound:

Formula (H2)

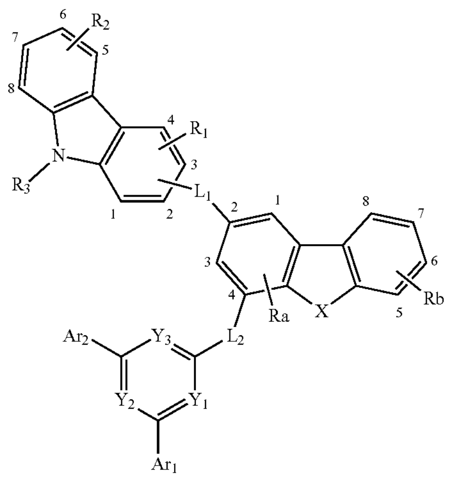

in Formula (H2), $Y_1$, $Y_2$ and $Y_3$ each independently represent:

CR' or a nitrogen atom, and at least two of $Y_1$, $Y_2$ and $Y_3$ represents a nitrogen atom;

R', $Ar_1$ and $Ar_2$ each represent:

a hydrogen atom, a substituted or unsubstituted alkyl group having 1 to 12 carbon atoms, or a substituted or unsubstituted aryl group having 6 to 30 ring forming carbon atoms, provided that not all of R', $Ar_1$ and $Ar_2$ represent hydrogen atoms at the same time;

X represents an oxygen atom or a sulfur atom;

Ra and Rb each independently represent a substituent;

$L_1$ represents:

a single bond, a substituted or unsubstituted alkylene group having 1 to 12 carbon atoms, a substituted or unsubstituted arylene group having 6 to 30 ring forming carbon atoms, or a divalent linking group composed of a combination thereof;

$L_2$ represents:

a single bond, a substituted or unsubstituted alkylene group having 1 to 12 carbon atoms, a substituted or unsubstituted arylene group having 6 to 30 ring forming carbon atoms, a substituted or unsubstituted heteroarylene group having 5 to 30 ring forming atoms, or a divalent linking group composed of a combination thereof;

$R_1$ and $R_2$ each independently represent:

a substituted or unsubstituted alkyl group having 1 to 12 carbon atoms, a cyano group, a halogen atom, or an unsubstituted or substituted aryl group having 6 to 30 ring forming carbon atoms, provided that the substituted aryl group has a substituent represented by Formulas (A-1) or (A-2);

$R_3$ represents:

a substituted or unsubstituted alkyl group having 1 to 12 carbon atoms, a substituted or unsubstituted aryl group having 6 to 30 ring forming carbon atoms, or a substituted or unsubstituted heteroaryl group having 5 to 30 ring forming atoms;

n1 represents an integer of 0 to 3, n2 represents an integer of 0 to 4, na2 represents an integer of 0 to 2, nb2 represents an integer of 0 to 4, when n1 to n2, na2 and nb2 each represent an integer of 2 or more, a plurality of $R_1$, $R_2$, Ra, and Rb may be the same or different, and adjacent Ra and Rb may be bonded together to form a ring structure, Formula (A-1)

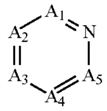

-continued

Formula (A-2)

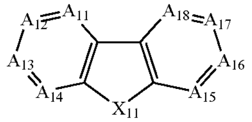

in Formulas (A-1) and (A-2), $A_1$ to $A_5$ and $A_{11}$ to $A_{18}$ each independently represent CRc or a nitrogen atom, and Rc represents a hydrogen atom, a substituent, or a bond, one of $A_1$ to $A_5$ and one of $A_{11}$ to $A_{18}$ represent CRc, and Rc represents a bond which is directly bonded to an aryl group having 6 to 30 ring forming carbon atoms and represented by $R_1$ and $R_2$, other Rc may be the same or different, and adjacent Rc may be bonded together to form a ring structure; and $X_{11}$ represents an oxygen atom or a sulfur atom.

2. The organic electroluminescent element of claim 1, wherein $L_1$ represents a single bond, a phenylene group, a biphenylene group, or an alkylene group having 2 carbon or fewer.

3. A display device provided with the organic electroluminescent element described in claim 2.

4. A lighting device provided with the organic electroluminescent element described in claim 2.

5. The organic electroluminescent element of claim 1, wherein $L_2$ represents a single bond, a phenylene group, a heteroarylene group, or an alkylene group having 2 carbon or fewer.

6. A display device provided with the organic electroluminescent element described in claim 5.

7. A lighting device provided with the organic electroluminescent element described in claim 5.

8. The organic electroluminescent element of claim 1, wherein the light emitting layer further contains another host compound having a different structure from the aforesaid aromatic heterocyclic derivative.

9. A display device provided with the organic electroluminescent element described in claim 8.

10. A lighting device provided with the organic electroluminescent element described in claim 8.

11. A display device provided with the organic electroluminescent element described in claim 1.

12. A lighting device provided with the organic electroluminescent element described in claim 1.

* * * * *